US006238668B1

(12) United States Patent
Danishefsky et al.

(10) Patent No.: US 6,238,668 B1
(45) Date of Patent: May 29, 2001

(54) COLON CANCER KH-1 AND N3 ANTIGENS

(75) Inventors: Samuel J. Danishefsky, Englewood; Prashant P. Deshpande, Plaindome, both of NJ (US); In Jong Kim, Seoul (KR); Philip Livingston, New York, NY (US); Hyun Jin Kim, New York, NY (US); Ragupathi Govindaswami, New York, NY (US); Tae Kyo Park, Taejon (KR)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/042,280

(22) Filed: Jan. 13, 1998

Related U.S. Application Data

(60) Provisional application No. 60/034,950, filed on Jan. 13, 1997.

(51) Int. Cl.[7] .................. A61K 39/00; A61K 39/385; A61K 45/00
(52) U.S. Cl. .................... 424/184.1; 424/193.1; 424/194.1; 424/130.1; 424/137.1; 424/138.1; 424/278.1; 424/283.1
(58) Field of Search .............................. 424/184.1, 193.1, 424/194.1, 130.1, 137.1, 138.1, 278.1, 283.1

(56) References Cited

U.S. PATENT DOCUMENTS 5,376,531   12/1994   Anderson et al. .................. 435/7.23
5,491,088 * 2/1996   Hellstrom et al. .

OTHER PUBLICATIONS

Ezzell (J. NIH Res, 7:46–49), 1995.*
Spitler (Cancer Biotherapy, 10:1–3), 1995.*
Boon (Adv. Can. Res., 58:177–210), 1992.*
Freshney (Culture of Animal Cells, A Manual of Basic Technique, Alan R. Liss, Inc., New York, p. 4), 1983.*
Dermer (Bio/Technology, 12:320), 1994.*
Deslande et al (J. Am. Chem. Soc., 120:1600–1614), 1998*
Tao and Levy (Nature, 362:765–758), 1993.*
Tokoyuni et al (Tetrahedron Lett., 31:2674–2676), 1990.*
Kaizu et al (JBC, 261:11254–11258), 1986.*
Kim et al (Cancer Res. (56:5985–5992), 1986.*
Nudelman et al. Novel Fucolipids of Human Adenocarcinoma: Characterization of the Major Le[y] Antigen of Human Adenocarcinoma as Trifucosylnonaosyl Le[y] Glycolipid (III[3]FucV[3]FucVI[2]FucnLc$_6$) J. Biol. Chem. 1986, 261, 11247–11253.
V. Bencomo et al., "Synthesis of glycopeptides having clusters of O–glycosylic disaccharide chains . . . ," Carbohydrate Research, 116, c9–c12, 1983 (Ex. 2).

M. Elofsson et al., "Preparation of Tn and Sialyl Tn Building Blocks . . . ," Tetrahedron, 53, 369–390, 1997 (Ex. 3).
M. Elofsson and J. Kihlberg, "Synthesis of Tn and Sialyl Tn building Blocks for Solid Phase Glycopeptide Synthesis," Tetrahedron Letters, 36, 7499–7502, 1995 (Ex. 4).
P. Fung et al., "Active Specific Immunotherapy of Murine Mammary . . . ," Cancer Research, 50, 4308–4314, 1990 (Ex. 5).
R. Gleiter et al., "Synthesis and Properties of Eight–and Ten–Membered Selenaradialenes," Tetrahedron Letters, 35, 8779–8782, 1994 (Ex. 6).
P. Grice et al., "Turning the Reactivity of Glycosides: Efficient One–pot Oligosaccharide Synthesis," Synlett, 781–784, 1995 (Ex. 7).
A. Kameyama et al., "Total Synthesis of Sailyl Lewis X *," Carbohydrate Research, 209 c1–c4, 1991 (Ex. 8).
H. Kondo et al., "In vitro action of human and porcine α–amylases . . . ," Carbohydrate Research, 204, 207–213, 1990 (Ex. 9).
H. Kunz et al., "Construction of Disaccharide N–Glycopeptides . . . ," Angew.Chem. Int. Ed. Engl., 24, 883–885, 1985 (Ex. 10).
H. Kunz et al., "Synthesis of O–Glycopeptides of the Tumor–Associated $T_n$ . . . ," Angew. Chem. Int. Ed. Engl., 25, 360–362, 1986 (Ex. 11).
B. Liebe and Horst Kunz, "Solid Phase Synthesis of a Tumor–Associated Sialyl–$T_n$ Antigen Glycopeptide . . . ," Agnew. Chem. Int.Ed. Engl. 33, 618–621, 1997 (Ex. 12).
H. Lönn, "Synthesis of a Tri– and a Hepta–saccharide . . . ," Carbohydrate Research, 139, 105–113, 1985 (Ex. 13).
K.C. Nicolaou et al., "Stereocontrolled Synthesis of Sialyl Le[x], . . . ," J. Chem. Soc., Chem. Commun., 870–872, 1991 (Ex. 14).
P. Schultheiss–Riemann et al., "O–Glycopeptide Synthesis . . . ," Angew. Chem. Int. Ed. Engl., 22, 62–63, 1983 (Ex. 15).

* cited by examiner

Primary Examiner—Susan Ungar
(74) Attorney, Agent, or Firm—Choate, Hall & Stewart; Karoline K.M. Shair

(57) ABSTRACT

The present invention provides processes for the preparation of the KH-1 and N3 antigens, as well as related analgoues thereof, which are useful as anticancer therapeutics. The present invention also provides various intermediates useful in the preparation of KH-1 and N3 and analogues thereof. Additionally, the invention provides various compositions comprising any of the analogues of KH-1 and N3 available through the methods of the invention and pharmaceutical carriers useful in the treatment of subjects suffering from various forms of epithelial cancer.

12 Claims, 23 Drawing Sheets

KH-1 Antigen (1) R =

Bioconjugatable analog (2) R =

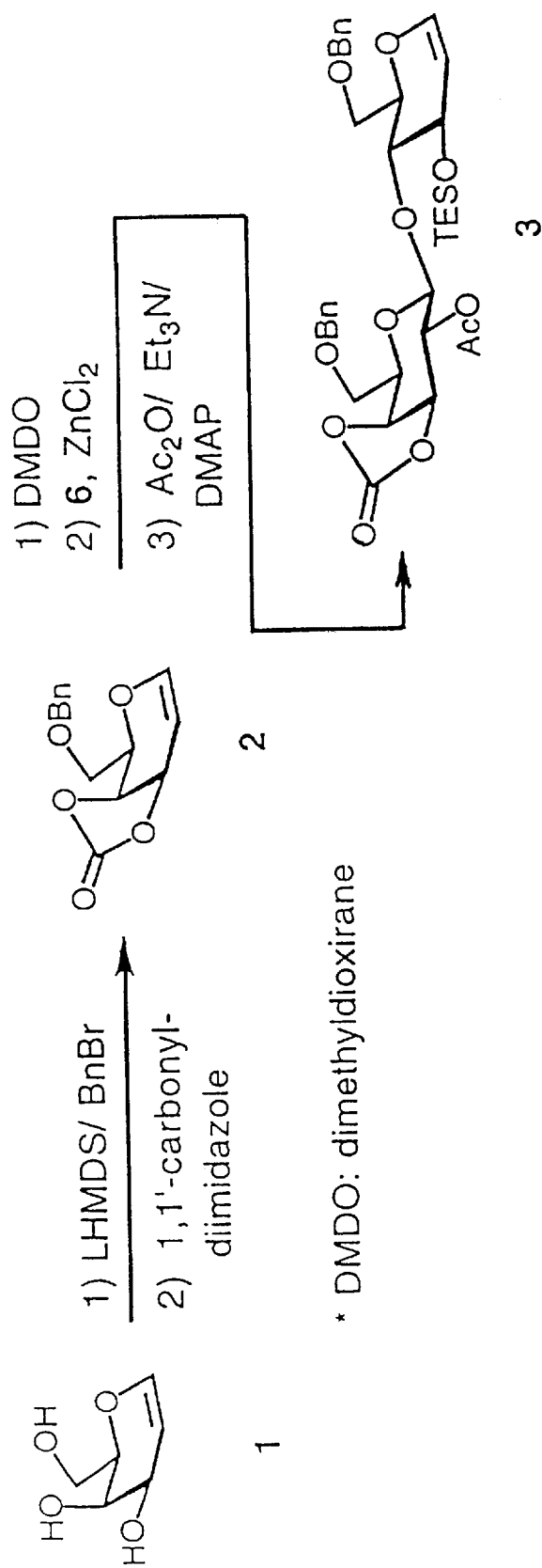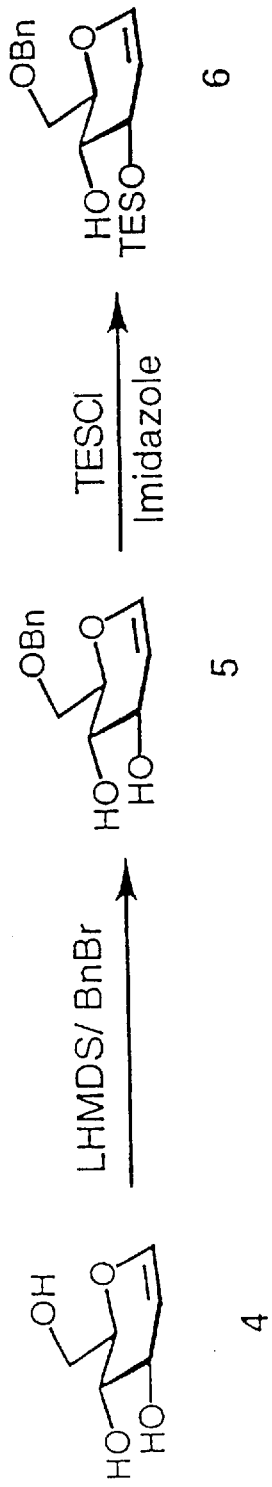
FIG. 5A
FIG. 5B
* DMDO: dimethyldioxirane

FIG. 6A
FIG. 6B
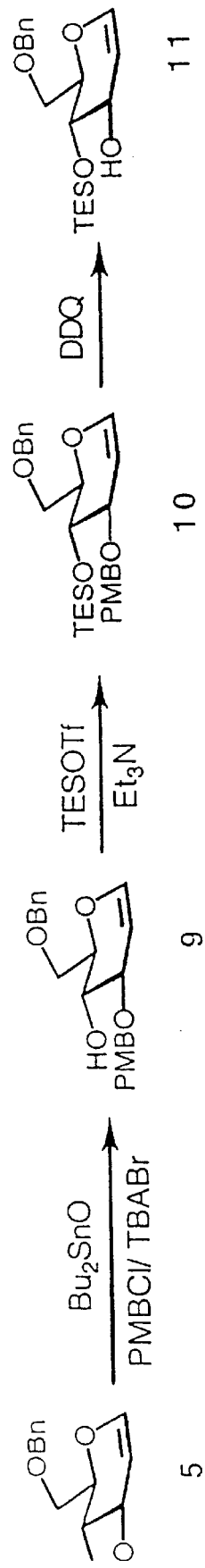
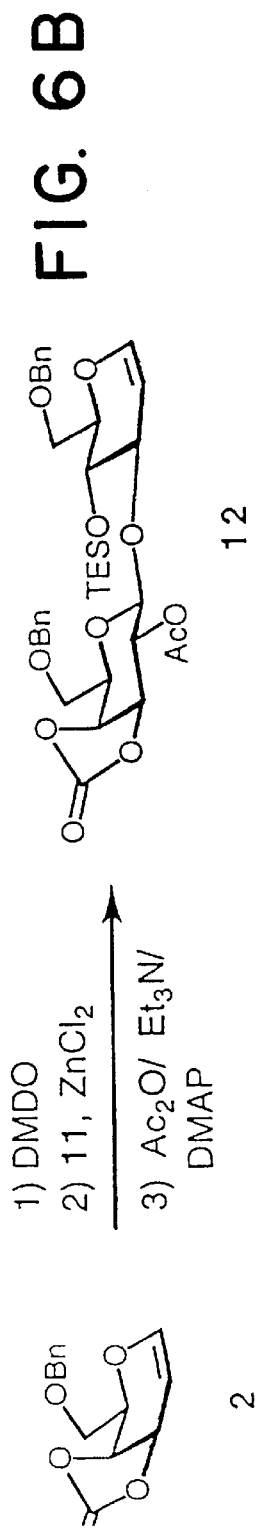

COLON CANCER KH-1 AND N3 ANTIGENS

This application claims benefit to U.S. Provisional Application Ser. No. 60/034,950, filed Jan. 13, 1997, now abandoned, the contents of which are hereby incorporated by reference into this application. Accordingly, the U.S. Government has certain rights in the invention.

This invention was made with government support under grants CA-28824-18, GM-15240-02, GM-16291-01, HL-25848-14 and AI-16943 from the National Institutes of Health. Additionally, the present invention was supported in part by a fellowship from the United States Army to Hyun Jin Kim (DAMD 17-97-1-7119).

Throughout this application, citations for various publications are provided. The disclosures of these publications are hereby incorporated in their entirety by reference into this application in order to more fully describe the state of the art to which this invention pertains.

FIELD OF THE INVENTION

The present invention is in the field of tumor-specific cell-surface antigens. In particular, the present invention relates to processes for the preparation of KH-1 and N3 antigens and analogues thereof which are useful as anticancer therapeutics. The present invention also provides novel compositions of matter which serve as intermediates for preparing the KH-1 and N3 antigens.

BACKGROUND OF THE INVENTION

The function of carbohydrates as structural materials and as energy storage units in biological systems is well recognized. By contrast, the role of carbohydrates as signaling molecules in the context of biological processes has only recently been appreciated. (M. L. Phillips, E. Nudelman, F. C. A. Gaeta, M. Perez, A. K. Singhal, S. Hakomori, J. C. Paulson, *Science,* 1990, 250, 1130; M. J. Polley, M. L. Phillips, E. Wagner, E. Nudelman, A. K. Singhal, S. Hakomori, J. C. Paulson, *Proc. Natl. Acad. Sci. USA,* 1991, 88, 6224; T. Taki, Y. Hirabayashi, H. Ishikawa, S. Kon, Y. Tanaka, M. Matsumoto, *J. Biol. Chem.,* 1986, 261, 3075; Y. Hirabayashi, A. Hyogo, T. Nakao, K. Tsuchiya, Y. Suzuki, M. Matsumoto, K. Kon, S. Ando, ibid., 1990, 265, 8144; O. Hindsgaul, T. Norberg, J. Le Pendu, R. U. Lemieux, *Carbohydr. Res.,* 1982, 109, 109; U. Spohr, R. U. Lemieux, ibid., 1988, 174, 211)

The elucidation of the scope of carbohydrate involvement in mediating cellular interaction is an important area of inquiry in contemporary biomedical research. The carbohydrate molecules, carrying detailed structural information, tend to exist as glycoconjugates (cf. glycoproteins and glycolipids) rather than as free entities. Given the complexities often associated with isolating the conjugates in homogeneous form and the difficulties in retrieving intact carbohydrates from these naturally occurring conjugates, the applicability of synthetic approaches is apparent. (For recent reviews of glycosylation see: Paulsen, H., Angew *Chem. Int. Ed. Engl.,* 1982, 21, 155; Schmidt, R. R., Angew. *Chem. Int. Ed. Engl.,* 1986, 25, 212; Schmidt, R. R., *Comprehensive Organic Synthesis, Vol.* 6, Chapter 1(2), Pergamon Press, Oxford, 1991; Schmidt, R. R., *Carbohydrates, Synthetic Methods and Applications in Medicinal Chemistry,* Part I, Chapter 4, VCH Publishers, Weinheim, New York, 1992. For the use of glycals as glycosyl donors in glycoside synthesis, see Lemieux, R. U., *Can. J. Chem.,* 1964, 42, 1417; Lemieux, R. U., Faser-Reid, B., *Can. J. Chem.,* 1965, 43:1460; Lemieux, R. U., Morgan, A. R., *Can. J. Chem.,* 1965, 43, 2190; Thiem, J., Karl, H., Schwentner, J., *Synthesis,* 1978, 696; Thiem. J. Ossowski, P., *Carbohydr. Chem.,* 1984, 3, 287; Thiem, J., Prahst, A., Wendt, T. *Liebigs Ann. Chem.,* 1986, 1044; Thiem, J., in *Trends in Synthetic Carbohydrate Chemistry,* Horton, D., Hawkins, L. D., McGarvey, G. L., eds., ACS Symposium Series #386, American Chemical Society, Washington, D.C., 1989, Chapter 8.)

The carbohydrate domains of the blood group substances contained in both glycoproteins and glycolipids are distributed in erythrocytes, epithelial cells and various secretions. The early focus on these systems centered on their central role in determining blood group specificities. (R. R. Race and R. Sanger, *Blood Groups in Man,* 6th ed., Blackwell, Oxford, 1975) However, it is recognized that such determinants are broadly implicated in cell adhesion and binding phenomena. (For example, see M. L. Phillips, E. Nudelman, F. C. A. Gaeta, M. Perez, A. K. Singhal, S. Hakomori, J. C. Paulson, *Science,* 1990, 250:1130.) Moreover, ensembles related to the blood group substances in conjugated form are encountered as markers for the onset of various tumors. (K. O. Lloyd, *Am. J. Clinical Path.,* 1987, 87, 129; K. O. Lloyd, *Cancer Biol.,* 1991, 2:421) Carbohydrate-based tumor antigenic factors might find applications at the diagnostic level, as resources in drug delivery or ideally in immunotherapy. (Toyokuni, T., Dean, B., Cai, S., Boivin, D., Hakomori, S., and Singhal, A. K., *J. Am. Chem Soc.,* 1994, 116, 395; Dranoff, G., Jaffee, E., Lazenby, A., Golumbek, P., Levitsky, H., Brose, K., Jackson, V., Hamada, H., Paardoll, D., Mulligan, R., *Proc. Natl. Acad. Sci. USA,* 1993, 90, 3539; Tao, M. H., Levy, R., *Nature,* 1993, 362, 755; Boon, T., *Int. J. Cancer,* 1993, 54, 177; Livingston, P. O., *Curr. Opin. Immunol.,* 1992, 4, 624; Hakomori, S., *Annu. Rev. Immunol.,* 1984, 2, 103; K. Shigeta, et al., *J. Biol. Chem.,* 1987, 262, 1358)

The use of synthetic carbohydrate conjugates to elicit antibodies was first demonstrated by Goebel and Avery in 1929. (Goebel, W. F., and Avery, O. T., *J. Exp. Med.,* 1929, 50, 521; Avery, O. T., and Goebel, W. F., *J. Exp. Med.,* 1929, 50, 533.) Carbohydrates were linked to carrier proteins via the benzenediazonium glycosides. Immunization of rabbits with the synthetic antigens generated polyclonal antibodies. Other workers (Allen, P. Z., and Goldstein, I. J., *Biochemistry,* 1967, 6, 029; Rude, E., and Delius, M. M., *Carbohvdr. Res.,* 1968, 8, 219; Himmelspach, K., et al., *Eur. J. Immunol.,* 1971, 1, 106; Fielder, R. J., et al., *J. Immunol.,* 1970, 105, 265) developed similar techniques for conjugation of carbohydrates to protein carriers. Most of them suffered by introducing an antigenic determinant in the linker itself, resulting in generation of polyclonal antibodies. Kabat (Arakatsu, Y., et al., *J. Immunol.,* 1966, 97, 858), and Gray (Gray, G. R., *Arch. Biochem. Bioshys.,* 1974, 163, 426) developed conjugation methods that relied on oxidative or reductive coupling, respectively, of free reducing oligosaccharides. The main disadvantage of these techniques, however, is that the integrity of the reducing end of the oligosaccharide was compromised. In 1975 Lemieux described the use an 8-carbomethoxy-1-octanol linker (Lemieux, R. U., et al., *J. Am. Chem. Soc.,* 1975, 97, 4076) which alleviated the problem of linker antigenicity and left the entire oligosaccharide intact. Equally effective in producing glycoconjugates was the allyl glycoside method described by Bernstein and Hall. (Bernstein, M. A., and Hall, L. D., *Carbohydr.*

Res., 1980, 78, C1.) In this technique the allyl glycoside of the deblocked sugar is ozonized followed by a reductive workup. The resultant aldehyde is then reductively coupled to a protein carrier with sodium cyanoborohydride.

In the mid-70's and early 80's Lemieux and his collaborators made contributions to antibody production stimulated by synthetic glycoconjugates (Lemieux, R. U., et al., *J. Am. Chem. Soc.,* 1975, 97, 4076) and to conformational issues (Lemieux, R. U., et al., *Can. J. Chem.,* 1979, 58, 631; Spohr, U., et al., *Can. J. Chem.,* 1985, 64, 2644; Vandonselaar, M., et al., *J. Biol. Chem.,* 1987, 262, 0848) important in the interactions of the blood group determinants (and analogues thereof) with the carbohydrate binding proteins known as lectins. More recently, workers at Bristol-Myers Squibb reported the X-ray crystal structure of the Lewis y epitope complexed with the antibody BR96. (Jeffrey, P. D., et al., *Nature Structural Biol.,* 1995, 2, 466.) Two main components appear to govern recognition between carbohydrates and most antibodies. The first is multiple hydrogen bonding between the sugar hydroxyls and the amino acid residues of Asp, Asn, Glu, Gln, and Arg. The second major interaction is stacking between the sugar-ring faces and aromatic side chains, which occurs most frequently with tryptophan. In the complex with BR96 the most significant interactions involve the latter; additional hydrogen bonding occurs between the sugar hydroxyls and the indole nitrogens. Most antibody binding sites can support about 6 linear carbohydrate residues in a groove or cavity shaped binding site.

Glycoconjugates may be used in direct immunotherapy or the monoclonal antibodies generated from vaccinations may be used to specifically target known chemotherapeutic agents to tumor sites. The immune response to carbohydrates is generally not strong, resulting mainly in production of IgM type antibodies. IgM antibodies are capable of complement fixation. Complement is a family of enzymes that can lyse cells to which antibodies are bound. The response to carbohydrate antigens normally does not enlist the use of T-cells which would aid in the body's rejection of the tumor. While the probability of complete tumor rejection as a result of vaccination with a conjugate is unlikely, such treatments will boost immune surveillance and recurrence of new tumor colonies can be reduced. (Dennis, J ., *Oxford Glycosystems Glyconews Second,* 1992; Lloyd, K. O., in *Specific Immuotherapy of Cancer with Vaccines,* 1993, New York Academy of Sciences, 50–58.) Toyokuni and Singhal have described a synthetic glycoconjugate (Toyokuni, T., et al., *J. Am. Chem. Soc.,* 1994, 116, 395) that stimulated a measurable IgG titer, a result which is significant since an IgG response is generally associated with enlistment of helper T cells.

The use of immunoconjugates has shown promise in the reduction of large tumor masses. The workers at Bristol-Myers Squibb (Trail, P. A., et al., *Science,* 1993, 261, 212) have described the attachment of the known chemotherapeutic drug doxorubicin to the antibody BR96. BR96 is an anti-Lewis y antibody which has been shown to bind to human breast, lung and colon carcinomas. Athymic mice that have had human cancers (L2987-lung, RCA-colon, and MCF7-breast carcinomas) xenografted subcutaneously were treated with the drug-antibody conjugate (BR96-DOX). The result was complete regression of the tumor mass in 78% of the mice treated. BR96 is efficiently-internalized by cellular lysosomes and endosomes following attachment to the cell surface. The change in pH upon internalization results in cleavage of the labile hydrazone thereby targeting the drug specifically to the desired site.

Many of the blood group determinant structures can also occur in normal tissues. Antigen expression in normal cells and cancer cells can have subtle distributional differences. In the case of Le y, which does appear in normal tissues, the expression of the determinant in tumor cells tends to be in the form of mucins which are secreted. Mucins are glycoproteins with a high content of the amino acids serine and threonine. It is through the hydroxyl functionality of these amino acids that Lewis y is linked. Thus, in terms of generating competent antibodies against tumor cells expressing the Le y antigen, it is important that the antibody recognize the mucin structure.

Structurally, the blood group determinants fall into two basic categories known as type I and type II. Type I is characterized by a backbone comprised of a galactose 1-3β linked to N-acetyl glucosamine while type II contains, instead, a 1-4β linkage between the same building blocks (cf. N-acetyl lactosamine). The position and extent of a-fucosylation of these backbone structures gives rise to the Lewis-type and H-type specificities. Thus, monofucosylation at the C4-hydroxyl of the N-acetyl glucosamine (Type I series) constitutes the Le a type, whereas fucosylation of the C3-hydroxyl of this sugar (Type II series) constitutes the Le x determinant. Additional fucosylation of Le a and Le x types at the C2' hydroxyl of the galactose sector specifies the Le b and Le y types, respectively. The Le y determinant is expressed in human colonic and liver adenocarcinomas. (Levery, S. B., et al., *Carbohydr. Res.,* 1986, 151, 311; Kim, Y. S., *J. Cellular Biochem. Suppl.,* 16G 1992, 96; Kaizu, T., et al., *J. Biol. Chem.,* 1986, 261, 11254; Levery, S. B., et al., *Carbohydr. Res.,* 1986, 151, 311; Hakomori, S., et al., *J. Biol. Chem.,* 1984, 259, 4672;Fukushi, Y., et al., ibid., 1984, 259, 4681; Fukushi, Y., et al., ibid., 1984, 259, 10511.)

The presence of an α-monofucosyl branch, solely at the C2'-hydroxyl in the galactose moiety in the backbone, constitutes the H-type specifity (Types I and II). Further permutation of the H-types by substitution of α-linked galactose or α-linked N-acetylgalactosamine at its C3'-hydroxyl group provides the molecular basis of the familiar serological blood group classifications A, B, and O. (Lowe, J. B., The Molecular Basis of Blood Diseases, Stamatoyannopoulos, et al., eds., W. B. Saunders Co., Philadelphia, Pa., 1994, 293.)

Several issues merit consideration in contemplating the synthesis of such blood group substances and their neoglycoconjugates. For purposes of synthetic economy it would be helpful to gain relief from elaborate protecting group manipulations common to traditional syntheses of complex branched carbohydrates. Another issue involves fashioning a determinant linked to a protein carrier. It is only in the context of such conjugates that the determinants are able to galvanize B-cell response and complement fixation. In crafting such constructs, it is beneficial to incorporate appropriate spacer units between the carbohydrate determinant and the carrier. (Stroud, M. R., et al., *Biochemistry,* 1994, 33, 0672; Yuen, C. T., et al., *J. Biochem.,* 1994, 269, 1595; Stroud, M. R., et al., *J. Biol. Chem.,* 1991, 266, 8439.)

The present invention provides new strategies and protocols for oligosaccharide synthesis. The object is to simplify such constructions such that relatively complex domains can be assembled with high stereo-specifity. Major advances in glycoconjugate synthesis require the attainment of a high degree of convergence and relief from the burdens associated with the manipulation of blocking groups. Another requirement is that of delivering the carbohydrate determinant with appropriate provision for conjugation to carrier proteins or lipids. (Bernstein, M. A., and Hall, L. D., *Carbohydr. Res.,* 1980, 78, Cl; Lemieux, R. U., *Chem. Soc. Rev.,* 1978, 7, 423; R. U. Lemieux, et al., *J. Am. Chem. Soc.,* 1975, 97, 4076.) This is a critical condition if the synthetically derived carbohydrates are to be incorporated into carriers suitable for biological application.

Antigens which are selective or ideally specific for cancer cells could prove useful in fostering active immunity. (Hakomori, S., *Cancer Res.*, 1985, 45, 2405–2414; Feizi, T., *Cancer Surveys*, 1985, 4, 245–269) Novel carbohydrate patterns are often presented by transformed cells as either cell surface glycoproteins or as membrane-anchored glycolipids. In principle, well chosen synthetic glycoconjugates which stimulate antibody production could confer active immunity against cancers which present equivalent structure types on their cell surfaces. (Dennis, J., Oxford GlycOsystems Glyconews Second, 1992; Lloyd, K. O., in *Specific Immunotherapy of Cancer with vaccines*, 1993, New York Academy of Sciences pp. 50–58) Chances for successful therapy improve with increasing restriction of the antigen to the target cell. A glycosphingolipid was isolated by Hakomori and collaborators from the breast cancer cell line MCF-7 and immunocharacterized by monoclonal antibody MBr1. (Bremer, E. G., et al., *J. Biol. Chem.*, 1984, 259, 14773–14777; Menard, S., et al., *Cancer Res.*, 1983, 43, 1295–1300).

The compounds prepared by processes described herein are antigens useful in adjuvant therapies as vaccines capable of inducing antibodies immunoreactive with epithelial carcinomas, for example, human colon, lung and ovarian tumors. Such adjuvant therapies have potential to reduce the rate of recurrence of cancer and increase survival rates after surgery. Clinical trials on 122 patents surgically treated for AJCC stage III melanoma who were treated with vaccines prepared from melanoma differentiation antigen GM2 (another tumor antigen which like MBr1 is a cell surface carbohydrate) demonstrated in patients (lacking the antibody prior to immunization) a highly significant increase in disease-free interval (P. O. Livingston, et al., *J. Clin Oncol.*, 12, 1036 (1994)).

The effectiveness of a vaccine derived from a tumor-associated antigens increases with the greater specificity of the carbohydrate domain of the antigen. One such antigen is the glycolipid KH-1, immunocharacterized by Hakomori et al. who have proposed its structure as 1. (Nudelman, E.; Levery, S. B.; Kaizu, T; Hakomori, S. -I., *J. Biol. Chem.*, 1986, 261, 11247. Kaizu, T.; Levery, S. B.; Nudelman, E; Stenkamp, R. E.; Hakomori, S. -I, *J. Biol. Chem.*, 1986, 261, 11254; Kim, S. Y.; Yuan, M.; Itzkowitz, S. H.: Sun, Q.; Kaizu, T.; Palekar, A; Trump, B. F.; Hakamori, S. -I, *Cancer Res.*, 1986, 46, 5985.)

This antigen has been claimed to be a highly specific marker for malignancy and pre-malignancies involving colonic adenocarcinoma. The nonasaccharide character of 1 (FIG. 1) is unique from a structural standpoint. The crystallographically derived presentation of the monoclonal antibody BR 96 bound to a Le$^y$ tetrasaccharide glycoside has been reported. (Jeffery, P. D.; Bajorath, J.; Chang, C. Y.; Dale, Y.; Hellstrom, I.; Hellstrom, E. K.; Sheriff, S., *Nature Structural Biology*, 1995, 2, 456.) The structure of the BR96:Ley complex suggested that this antibody might also have the capacity to recognize higher order fucosylated arrays.

Accordingly, the present invention relates to the total synthesis not only of 1 itself, but of congeners (cf. structure 2) which are suitable for conjugation to appropriate bioactive carrier systems.

SUMMARY OF THE INVENTION

Therefore, one object of the present invention is to provide processes for the preparation of the KH-1 and N3 antigens, as well as related analgoues thereof, useful as anticancer therapeutics.

Another object of the present invention is to provide various compounds useful as intermediates in the preparation of KH-1 and N3 and analogues thereof. A further object of the present invention is to provide methods of preparing such intermediates.

An additional object of the invention is to provide compositions comprising any of the analogues of KH-1 and N3 available through the preparative methods of the invention and pharmaceutical carriers useful in the treatment of subjects suffering from cancer. A further object of the invention is to provide methods of treatment of cancer using any of the analogues of KH-1 and N3 alone or conjugated to suitable carriers as disclosed herein available through the preparative methods of the invention, optionally in combination with pharmaceutical carriers.

BRIEF DESCRIPTION OF THE DRAWINGS

FIGS. 6(A), 6(B) and 6(C) provide a synthetic stratety for the Le a donor portion.

DETAILED DESCRIPTION OF THE INVENTION

Figure 1:
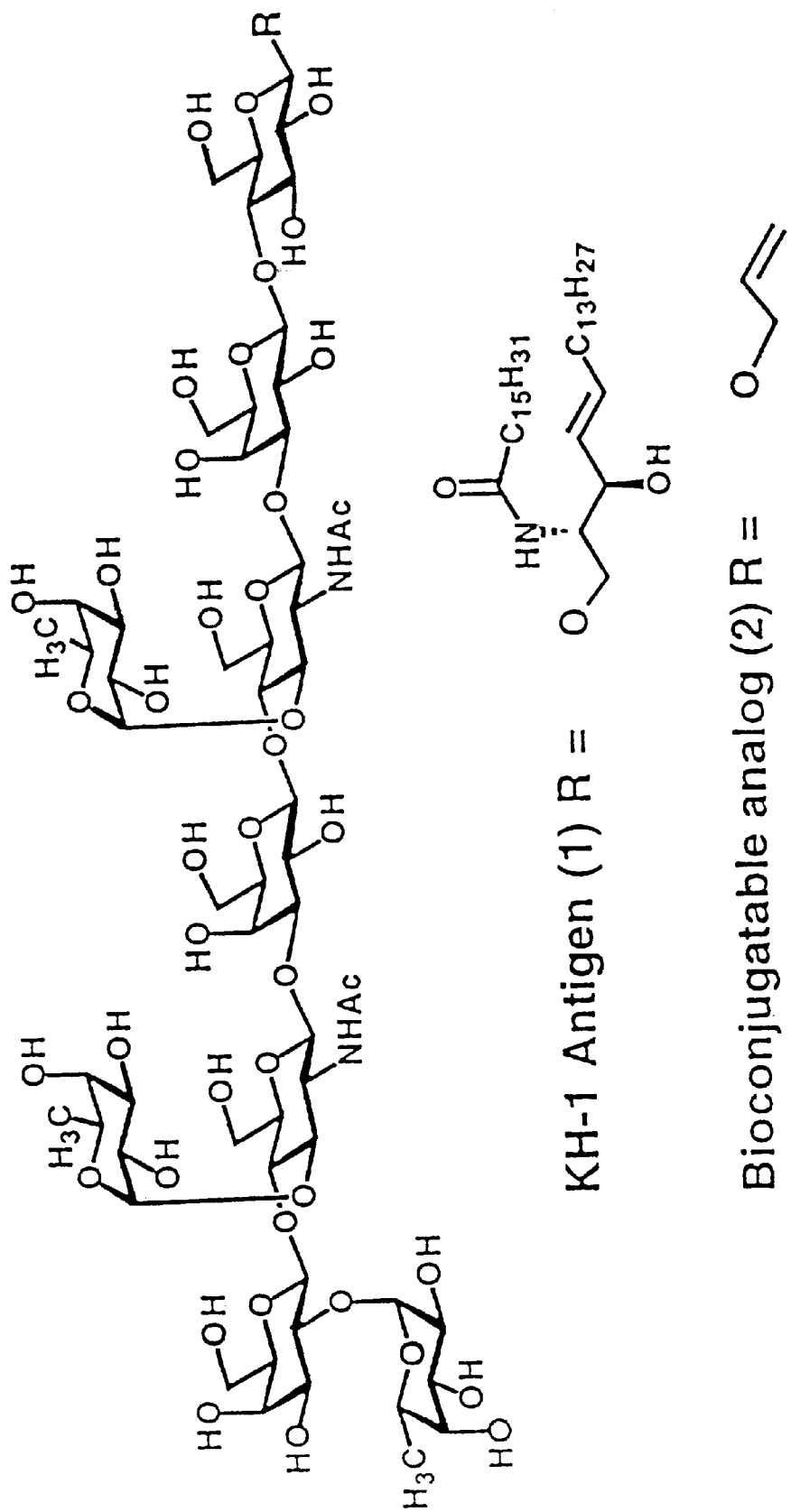
FIG. 1 show the structure of the cell surface antigen KH-1 ceramide and its bioconjugateable O-allyl ether form.
Figure 2A:
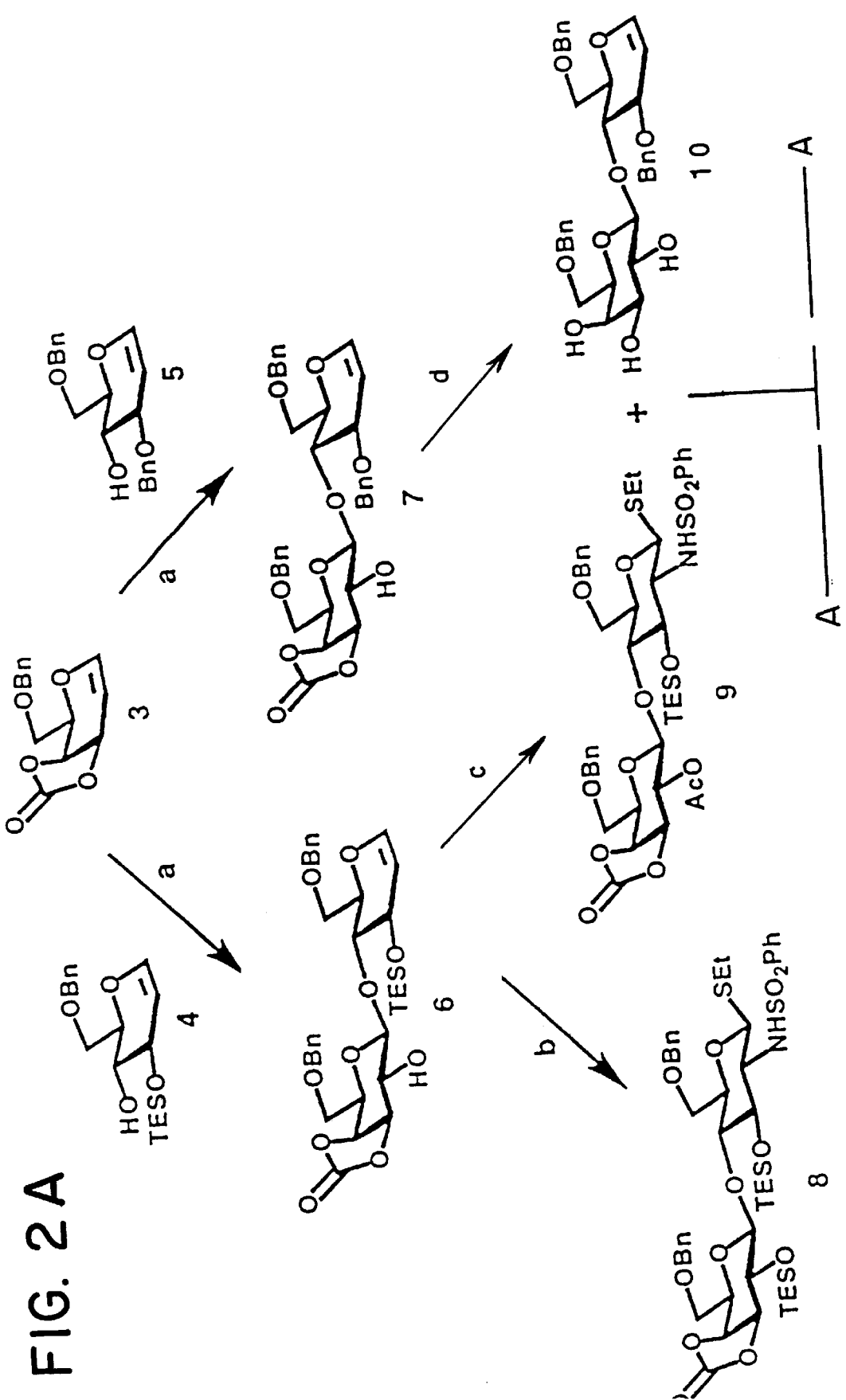
FIGS. 2(A) and 2(B) provide synthetic Scheme 1. Reagents: (a) (i) 3,3-dimethyldioxirane, $CH_2Cl_2$; (ii) 4 or 5, $ZnCl_2$, THF 65% for 6 & 55% for 7; (b) (i) TESOTf, $Et_3N$, DMAP, $CH_2Cl_2$, 92%, (ii) $I(coll)_2ClO_4$, $PhSO_2NH_2$, 4 Å molecular sieves, $CH_2Cl_2$, >90%; (iii) LHMDS, EtSH, DMF>90%; (c) (i) $Ac_2O$, $Et_3N$, DMAP, $CH_2Cl_2$, 95%; (ii) $I(coll)_2ClO_4$, $PhSO_2NH_2$, 4 Å molec-ular sieves, $CH_2Cl_2$, >90%; (iii) LHMDS, EtSH, DMF (iv) $AC_2O$, $Et_3N$, DMAP, $CH_2Cl_2$, 85%; (d) $K_2CO_3$, MeOH 80%; (e) (i) MeOTf, di-t-butylpyridine, $Et_2O$:$CH_2Cl_2$ (2:1), 4 Å MS (55%), (ii) $K_2CO_3$, MeOH (85%); (f) (i) MeOTf, di-t-butylpyridine, $Et_2O$:$CH_2Cl_2$ (2:1), 4 Å MS (60%); (ii) $Ac_2O$, Py, DMAP, $CH_2Cl_2$ (95%); (g) TBAF:AcOH (93%).
Figure 2B:
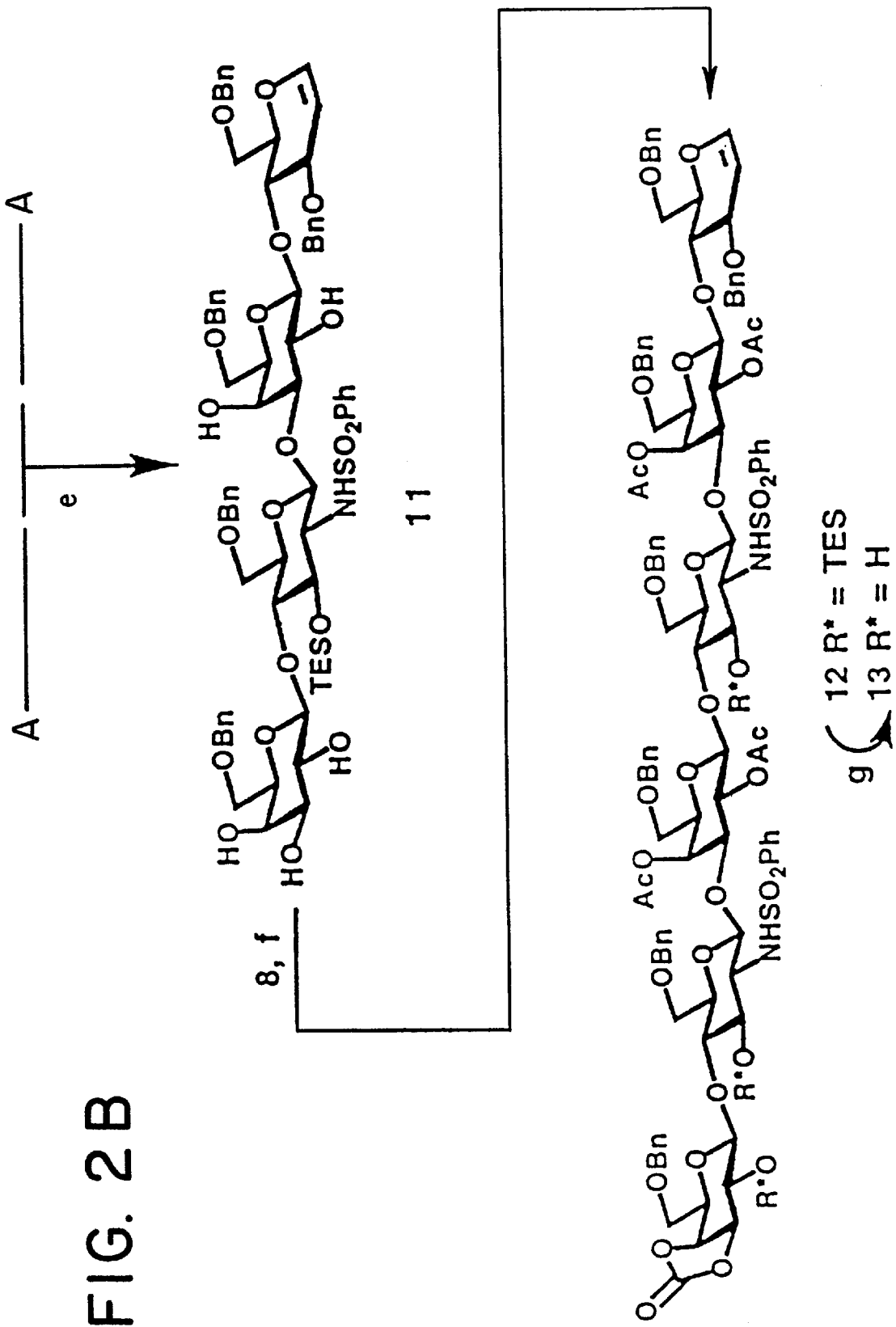
Figure 3A:
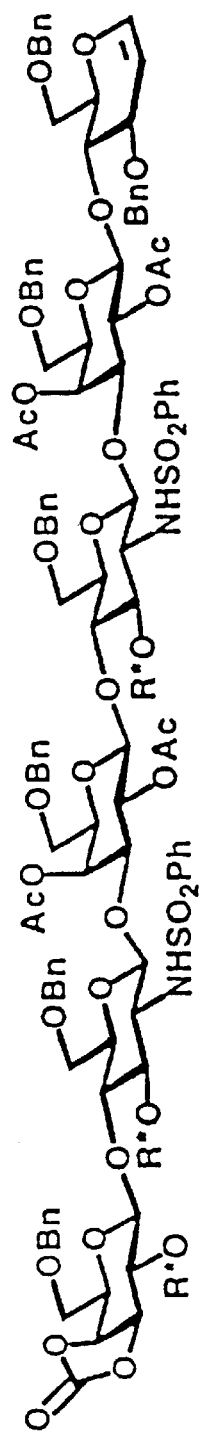
FIGS. 3(A) and 3(B) provide synthetic Scheme 2. Reagents: (a) 14, $Sn(OTf)_2$, Tol:THF(10:1), 4 A MS (60%); (b) (i) 3,3-dimethyldioxirane, $CH_2Cl_2$; (ii) EtSH, $CH_2Cl_2$, H$^+$ (cat); (iii) $Ac_2O$, Py, $CH_2Cl_2$ 60% (3 steps) (c) 17, MeOTf, $Et_2O$:$CH_2Cl_2$ (2:1), 4 Å MS (55%); (d) (i) Lindlar's catalyst, $H_2$, palmitic anhydride, EtOAc, 85% (ii) Na, $NH_3$, THF; (MeOH quench); (iii) $Ac_2O$, $Et_2N$, DMAP, $CH_2Cl_2$ (iv) MeONa, MeOH, 70% (3 steps); (e) (i) Na, $NH_3$, THF; (MeOH quench); (ii) $Ac_2O$, $Et_3N$, DMAP, $CH_2Cl_2$; (iii) 3,3-dimethyldioxirane, $CH_2Cl_2$; (iv) Allyl Alcohol (v) MeONa, MeOH, 60%.
Figure 3A:
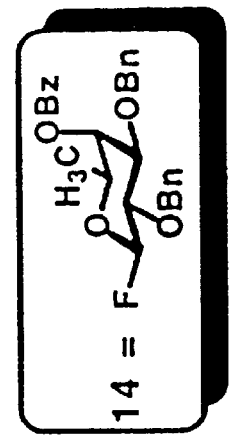
Figure 3A:
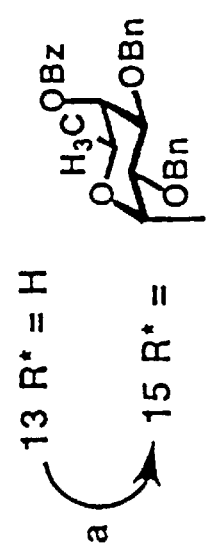
Figure 3B:
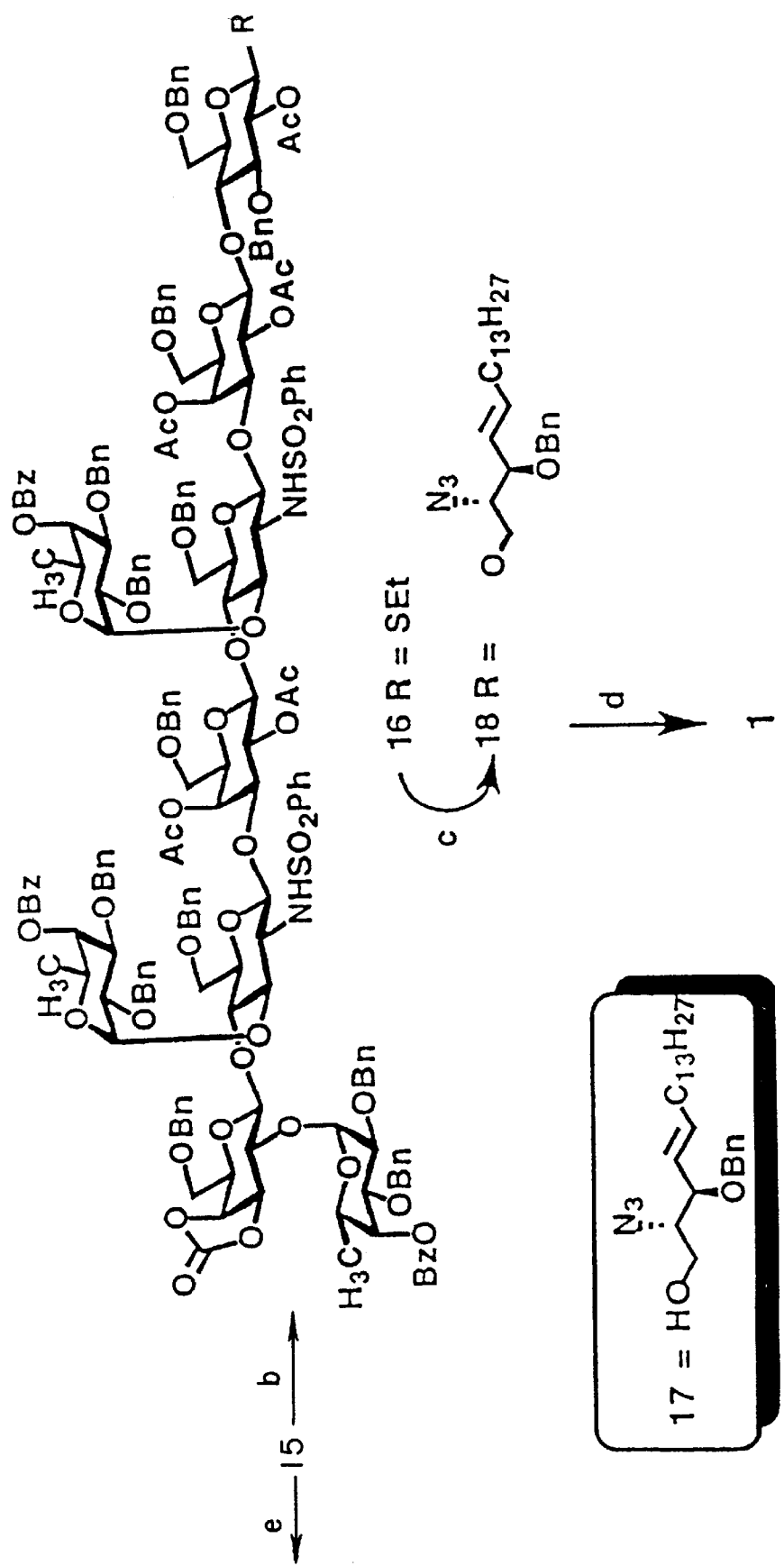
Figure 4:
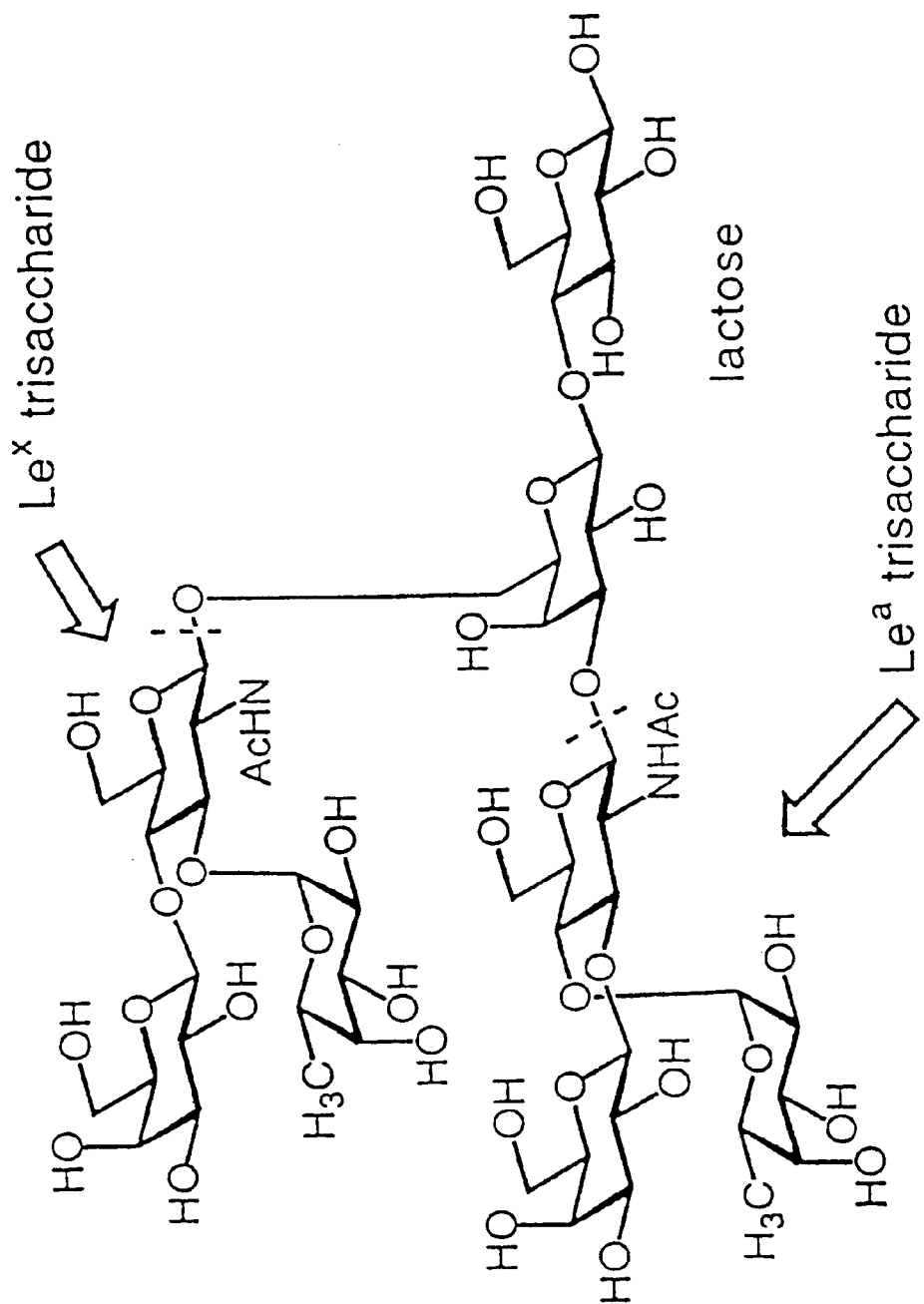
FIG. 4 provides a synthetic strategy for N3 antigen.
Figure 5C:
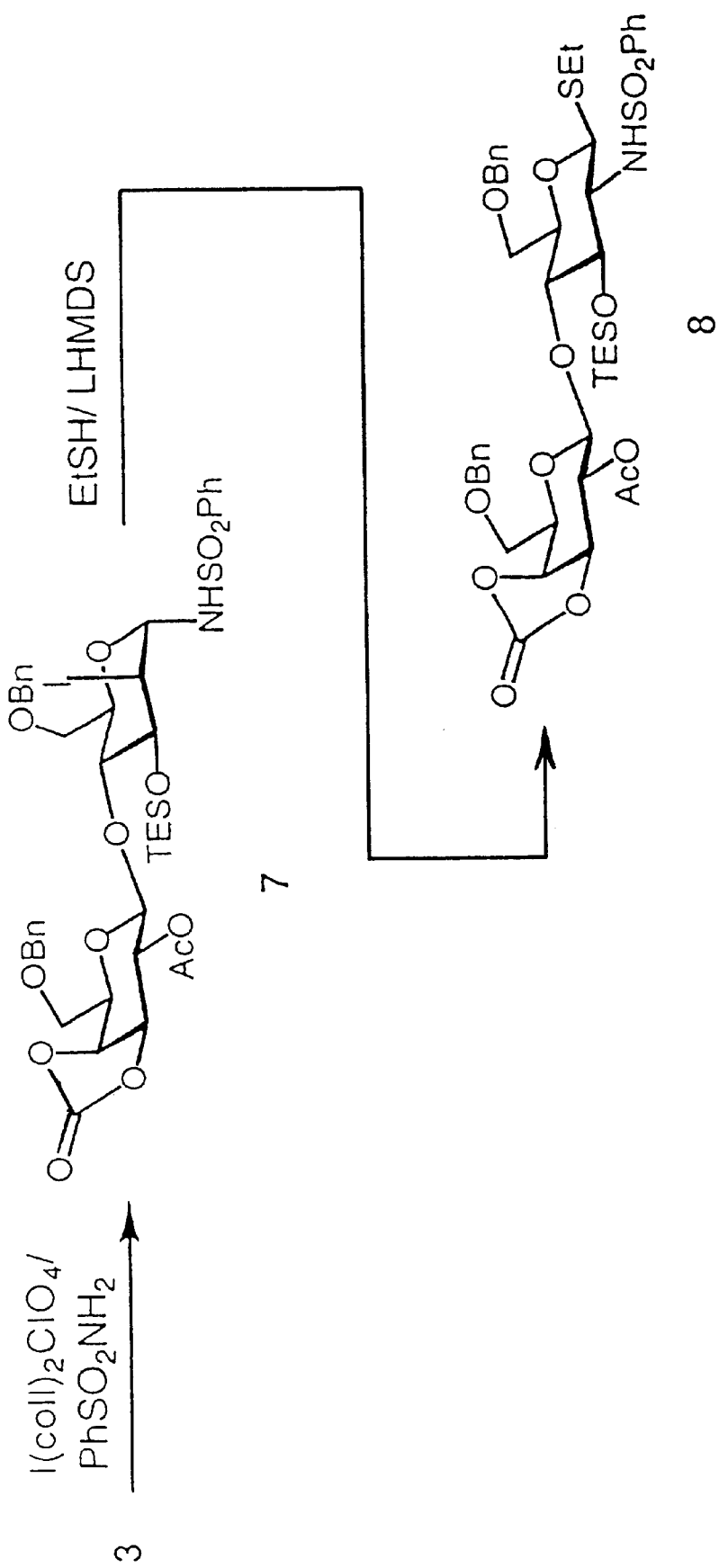
FIGS. 5(A), 5(B) and 5(B) provide a synthetic stratety for the Le x donor portion.
Figure 6C:
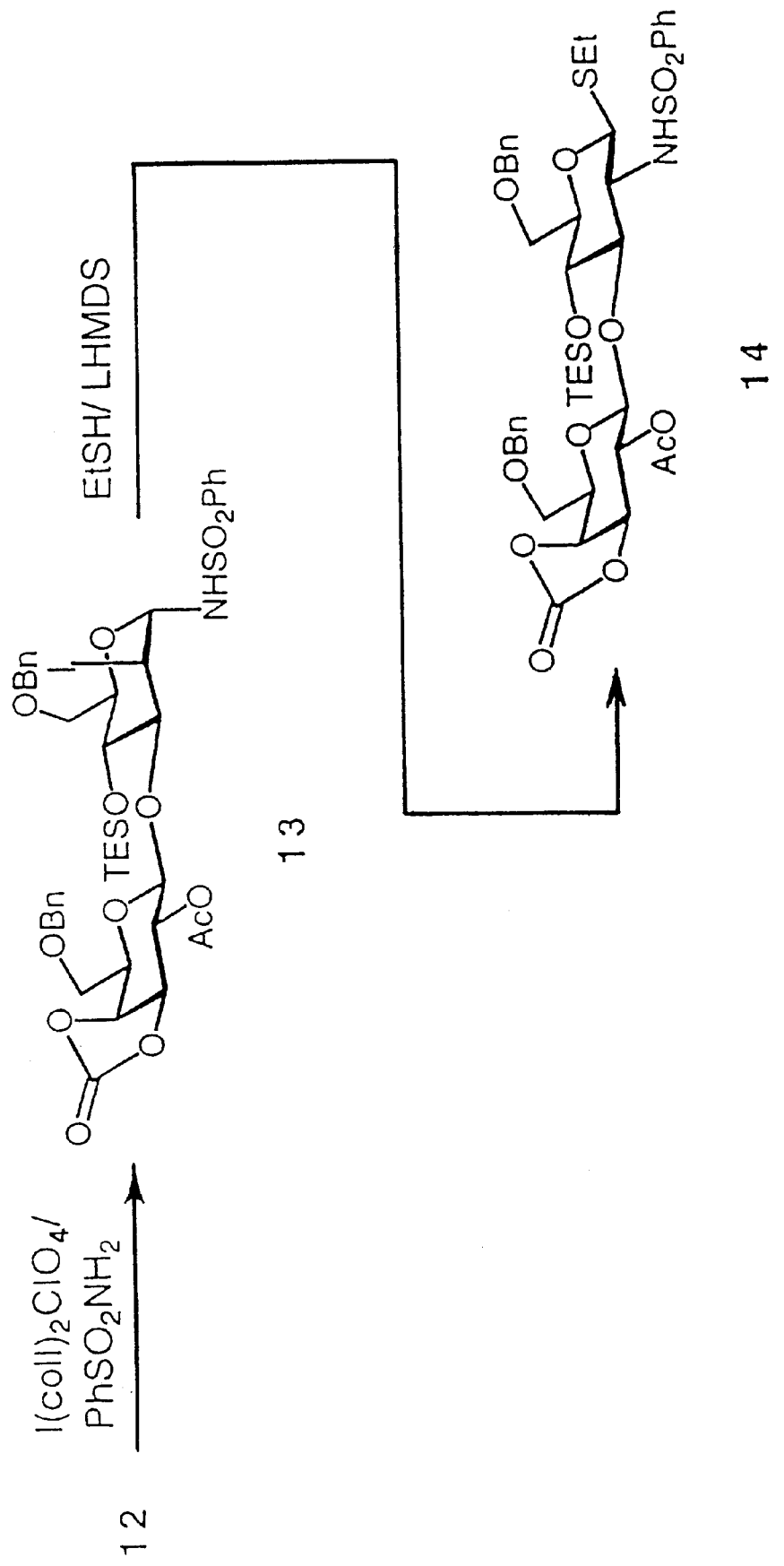
Figure 7A:
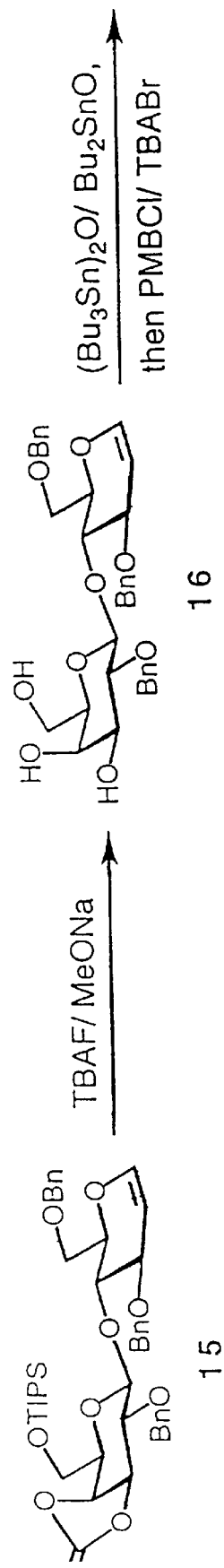
FIGS. 7(A) and 7(B) provide a synthetic stratety for the N3 acceptor portion.
Figure 7B:
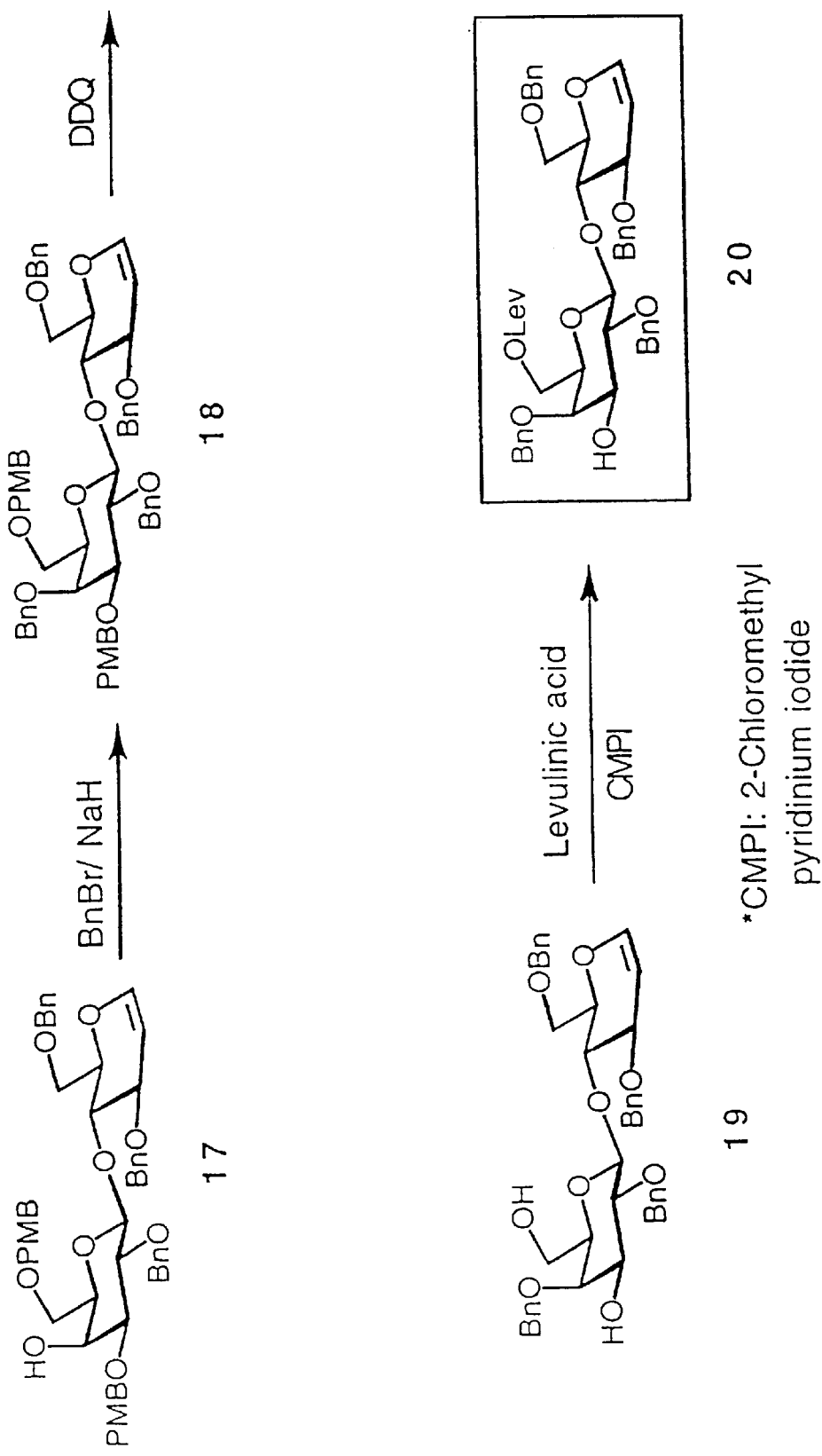
Figure 8:
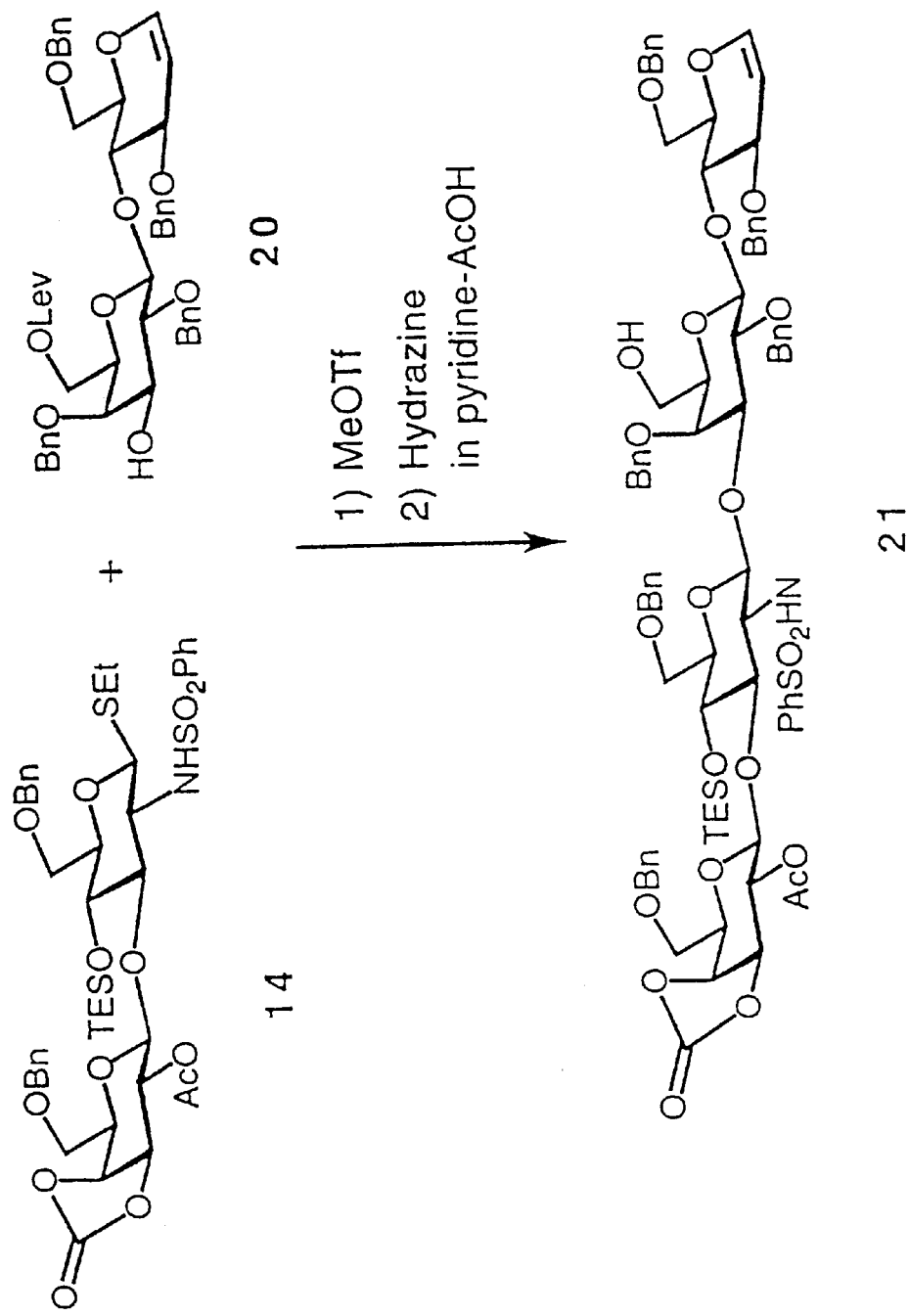
FIG. 8 provides a 2+2 coupling for the major N3 antigen.
Figure 9A:
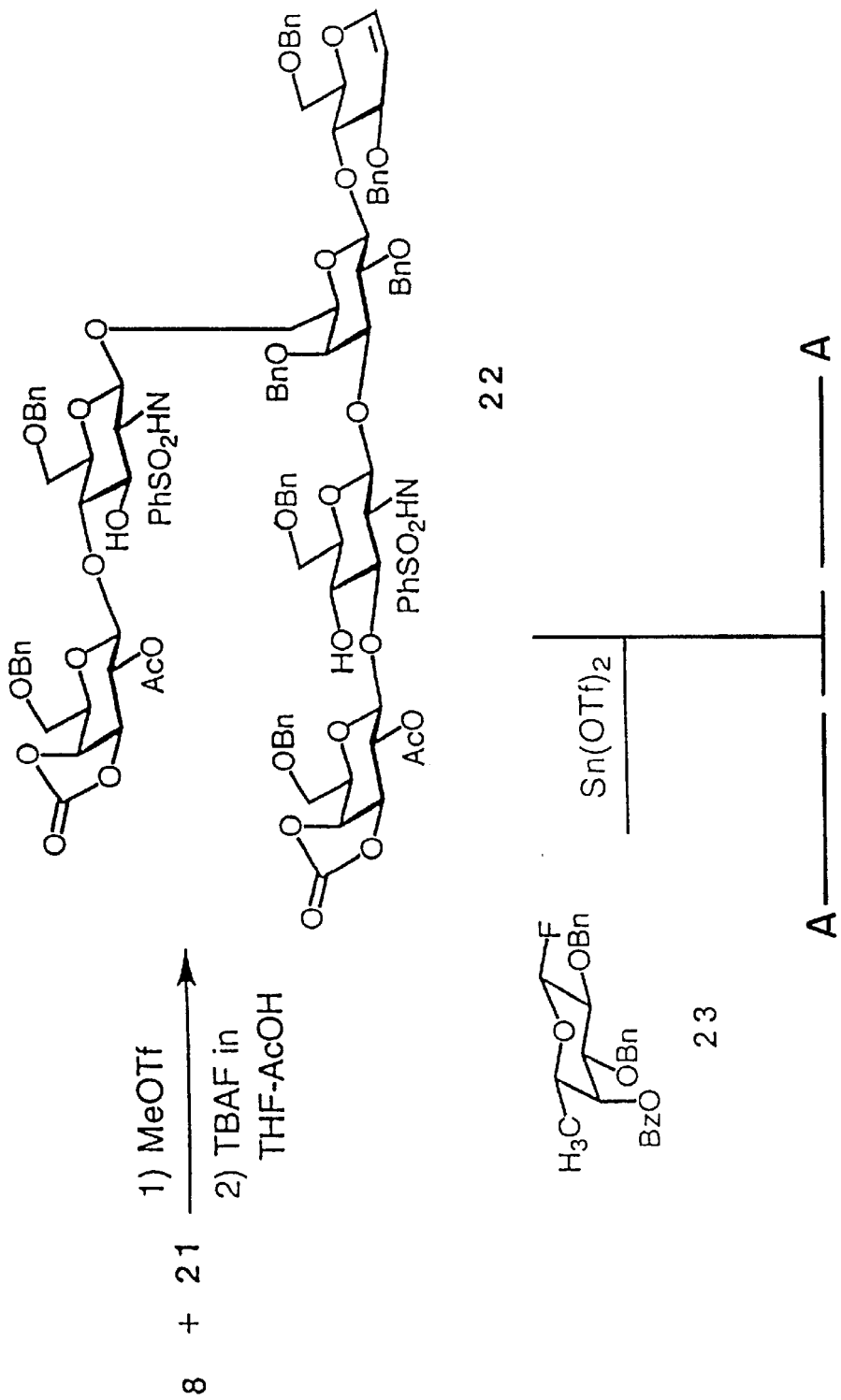
FIGS. 9(A) and 9(B) provide a 2+4 and 1+1 coupling for the N3 antigen.
Figure 9B:
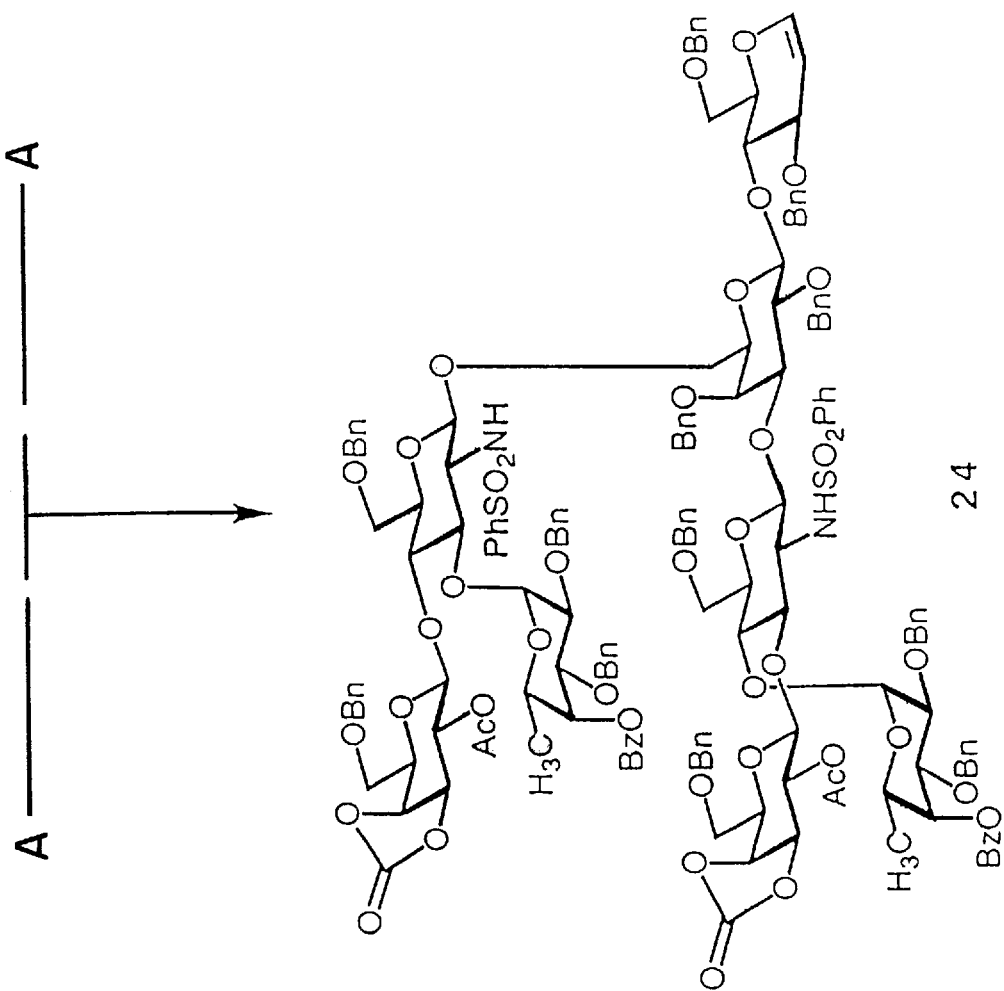
Figure 10A:
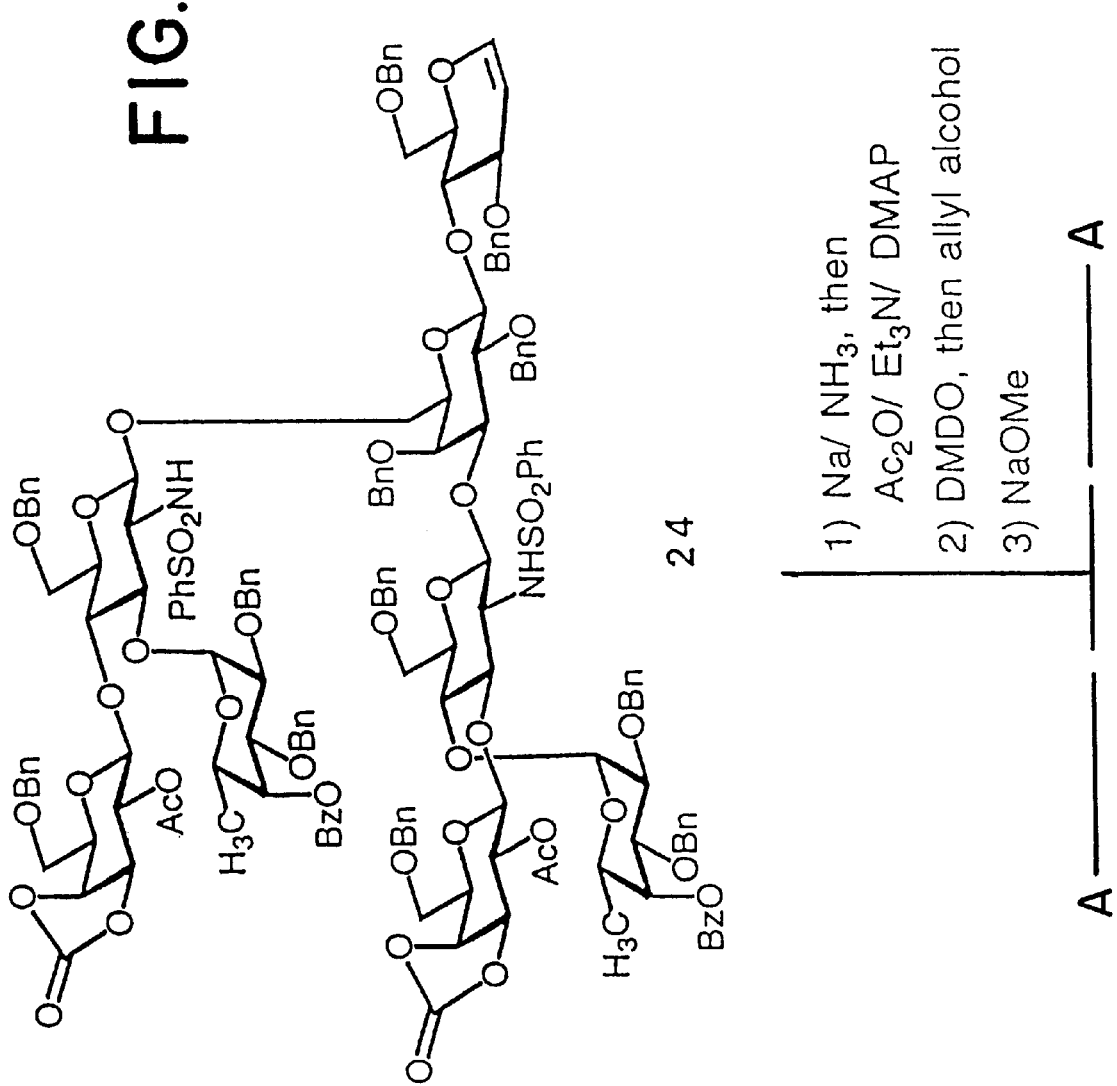
FIGS. 10(A) and 10(B) provide a pathway for deprotection of the major N3 epitope.
Figure 10B:
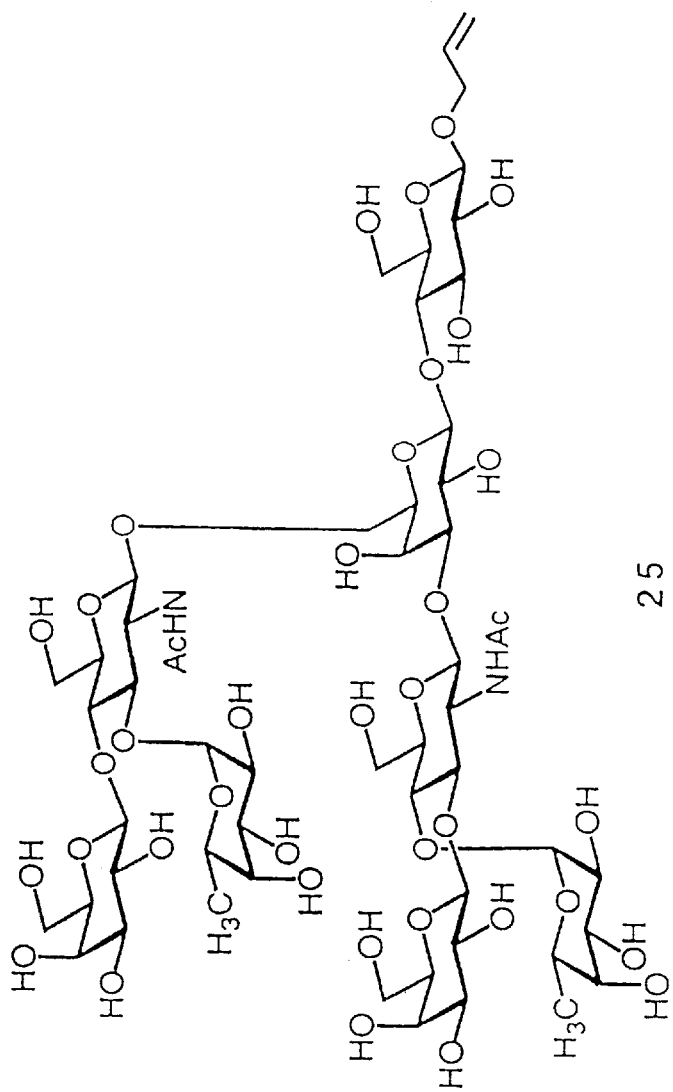

The subject invention provides a compound having the structure:

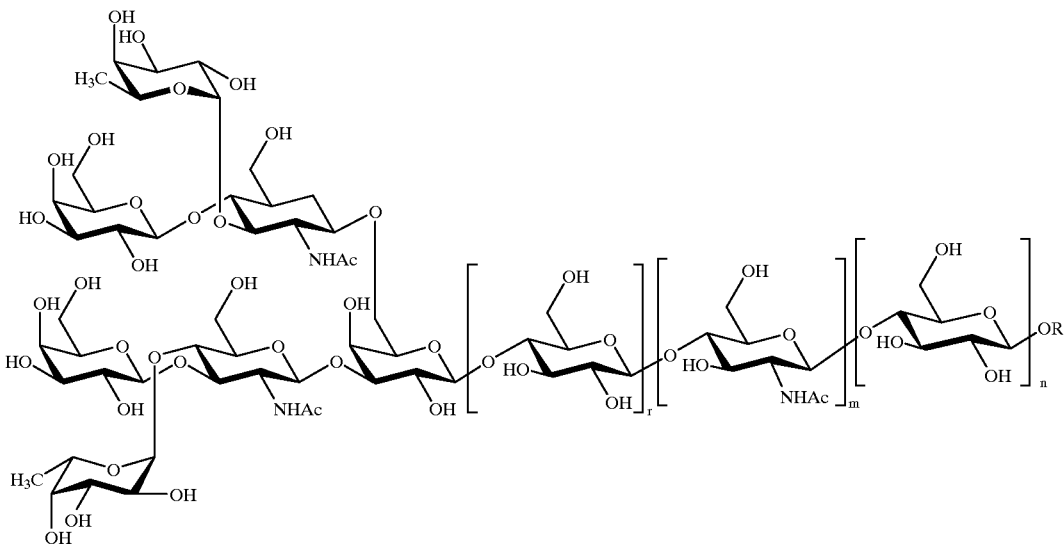

wherein R is H, substituted or unsubstituted alkyl, aryl or allyl, or an amino acyl moiety, an amino acyl residue of a peptide, an amino acyl residue of a protein, which amino acyl moiety or residue bears an ω-amino group or an ω-(=O)- group, which group is linked to O via a polymethylene chain having the structure —$(CH_2)_s$—, where s is an integer between about 1 and about 9, or a moiety having the structure:

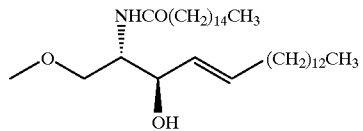

and wherein r, m and n are independently 0, 1, 2 or 3.

The present invention also provides a compound having the structure:

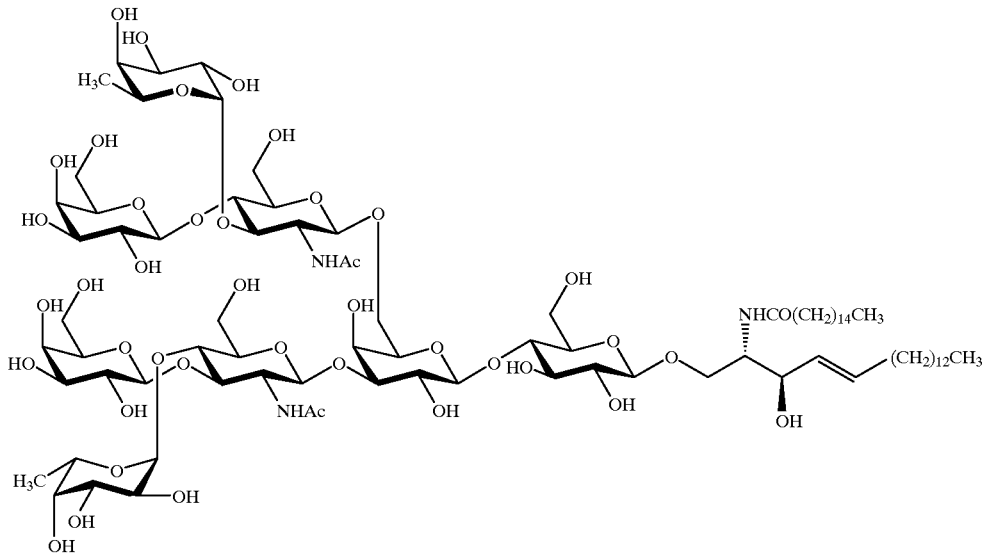

In one embodiment, the invention provides a compound wherein the protein is bovine serum albumin or KLH.

The invention also provides a compound having the structure:

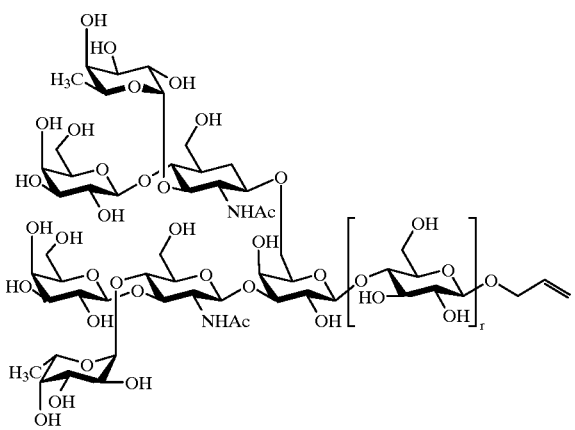

wherein r is 0, 1, 2, 3 or 4. In one embodiment, the invention provides the compound wherein r is 1.

The invention further provides a method of preparing a trisaccharide iodosulfonamide having the structure:

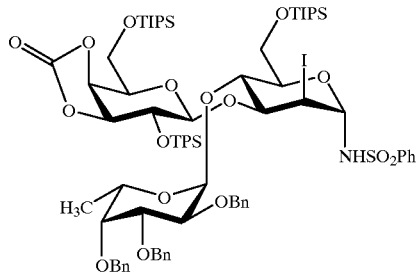

which comprises:

(a) (i) coupling a disaccharide glycal with an epoxide having the structure:

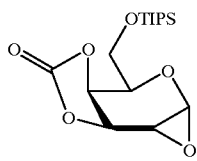

under suitable conditions to form a trisaccharide intermediate; and (ii) etherifying the trisaccharide intermediate with a suitable protecting agent to form a trisaccharide glycal having the structure:

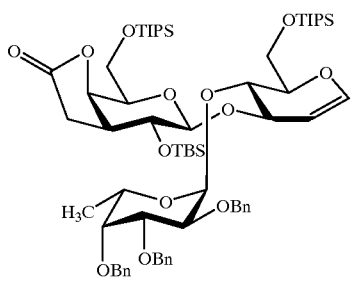

and (b) reacting the trisaccharide glycal formed in step (c) with an iodosulfonamidating agent under suitable conditions to form the trisaccharide iodosulfonamide. In one embodiment, the invention provides the method wherein the disaccharide glycal has the structure:

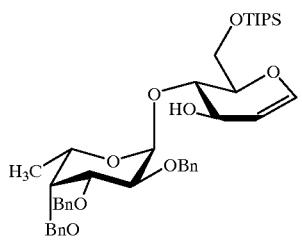

is prepared by a process which comprises:

(a) protecting a glucal having the structure:

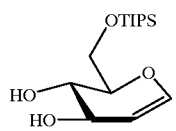

with a silylating agent under suitable conditions to form a protected glucal having the structure:

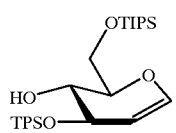

(b)(i) alkylating the protected glucal formed in step (a) with a fucosylfluoride having the structure:

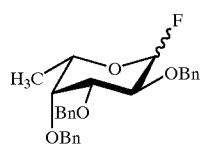

and (ii) deprotecting under suitable conditions to form the disaccharide glycal. In one embodiment, the invention provides the method wherein the silylating agent in step (a) is triphenylsilyl chloride. In another embodiment, the invention provides the method wherein the alkylating step is effected in the presence of an ionizing salt, and the ionizing salt is $AgClO_4$. In an additional embodiment, the invention provides the method wherein the conditions of the deprotecting step comprise a base. In yet another embodiment, the invention provides the method wherein the base is potassium carbonate. The method also encompasses the embodiment wherein the conditions of the coupling comprise an acid. The method further encompasses the embodiment wherein the acid is a Lewis acid. One example of the Lewis acid is zinc dichloride. One example of the silylating agent used is TBSOTf. The iodosulfonamidating agent of step (b) above may comprise $I(coll)_2ClO_4$ and and $PhSO_2NH_2$.

The present invention also provides a method of preparing a disaccharide stannane having the structure:

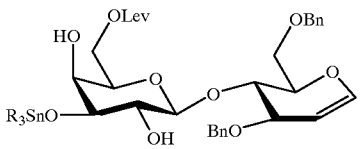

which comprises:

(a) (i) deprotecting a disaccharide glucal having the structure:

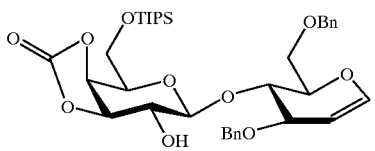

under suitable conditions to form a deprotected intermediate; and (ii) selectively reprotecting the deprotected intermediate with levulinic acid under suitable conditions to form a disaccharide levulinate having the structure:

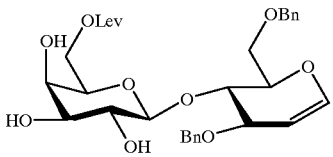

and (b) reacting the disaccharide levulinate formed in step (a) with a distannyl oxide having the formula $(R_3Sn)_2O$, wherein R is linear or branched chain alkyl or aryl, under suitable conditions to form the disaccharide stannane. The invention encompasses the method wherein the conditions of the deprotecting step comprise a fluoride salt. The invention further encompasses the method wherein the fluoride salt is a tetraalkylammonium fluoride. The method additionally encompasses the method wherein the tetraalkylammonium fluoride salt is tetra-n-butylammonium fluoride. The invention also encompasses the method wherein the conditions of the reprotecting step comprise 2-chloro-1-methylpyridinium iodide. In one embodiment, the invention provides the method wherein R is n-Bu.

The present invention further provides a method of preparing a disaccharide ethylthioglycoside having the structure:

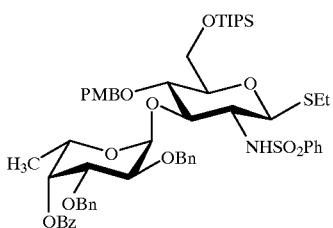

which comprises:

(a)(i) protecting a disaccharide glucal having the structure:

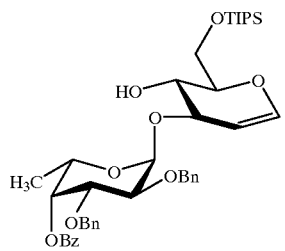

with a suitable protecting agent to form a protected disaccharide glucal; and (ii) reacting the protected disaccharide glucal under suitable conditions with an iodosulfonamidating agent to form a disaccharide iodosulfonamide having the structure:

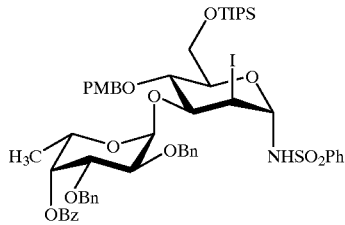

and (b) treating the disaccharide iodosulfonamide formed in step (a)(ii) with ethanethiol under suitable conditions to form the disaccharide ethylthioglycoside. The method encompasses the embodiment wherein the disaccharide glucal is prepared by a process which comprises:

(a) alkylating a protected glucal having the structure:

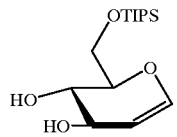

with a fucosyl fluoride having the structure:

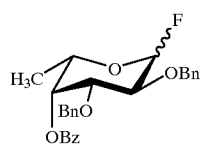

under suitable conditions to form the disaccharide glucal

The method encompasses the embodiment wherein the conditions of the alkylating step comprise an ionizing salt. In addition, the method encompasses the example wherein the ionizing salt is $AgClO_4$. The method also includes the example wherein the protecting agent is PMBCl. The method further encompasses the embodiment wherein the iodosulfonamidating agent in step (b) (ii) comprises I(coll)$_2ClO_4$ and $PhSO_2NH_2$. The method also encompasses the embodiment wherein the conditions of the treating step comprise a base. The method also includes the instance wherein the base is LHMDS.

The invention also provides a method of preparing an N3 allyl glycoside having the structure:

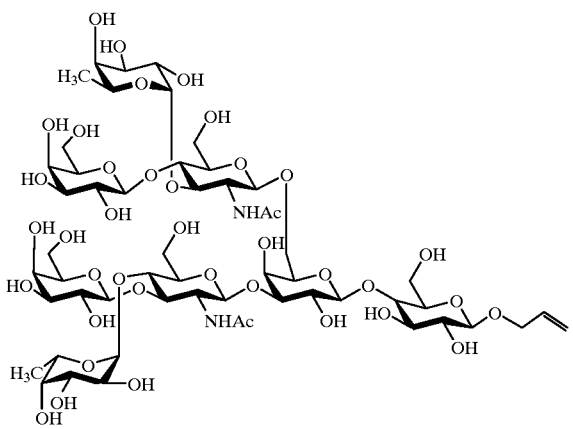

which comprises:

(a) desilylating a protected N3 glycal having the structure:

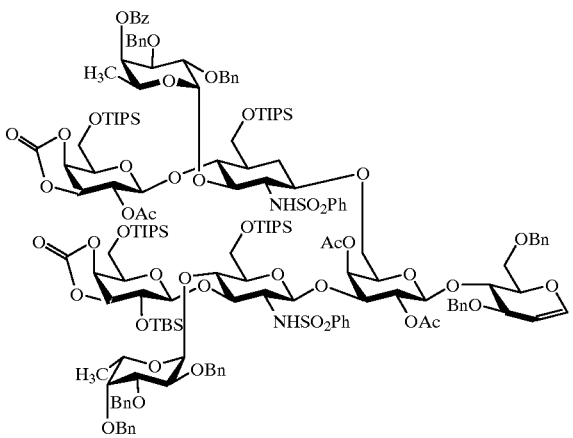

under suitable conditions to form a desilylated N3 glycal;

(b) deprotecting the desilylated N3 glycal formed in step (a) under suitable conditions to form a deprotected N3 glycal;

(c) treating the deprotected N3 glycal formed in step (b) with acetic anhydride in the presence of a suitable catalyst to form an N3 glycal acetate;

(d) epoxidizing the N3 glycal acetate formed in step (c) with an oxygen transfer agent under suitable conditions to form an N3 glycal epoxyacetate;

(e) cleaving the N3 glycal epoxyacetate formed in step (d) with allyl alcohol under suitable conditions to form an N3 glycal allyl ether; and (f) saponifying the N3 glycal allyl ether under suitable conditions to form the N3 allyl glycoside.

The invention also encompasses the method wherein the protected N3 glycal is prepared by a process which comprises coupling an ethylthioglycoside having the structure:

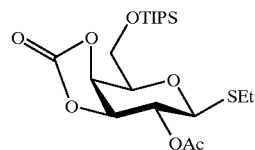

heptasaccharide glycal having the structure:

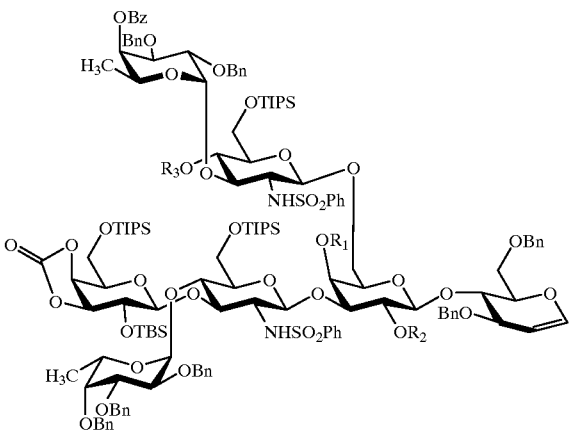

wherein $R_1$ and $R_2$ are Ac and $R_3$ is H, in the presence of an alkylating agent under suitable conditions to form the protected N3 glycal. The invention encompasses the method wherein the alkylating agent is MeOTf. The invention also encompasses the method wherein the conditions of the desilylating step comprise a fluoride salt. The invention also encompasses the method wherein the fluoride salt is a tetraalkylammonium fluoride. The invention also encompasses the method wherein the tetraalkylammonium fluoride is tetra-n-butylammonium fluoride. The invention further includes the method wherein the catalyst in the treating step is 2-N,N-dimethylaminopyridine. The invention also encompasses the method wherein the oxygen transfer agent is 3,3-dimethyldioxirane.

The present invention encompasses a method of preparing a heptasaccharide glycal diacetate intermediate having the structure:

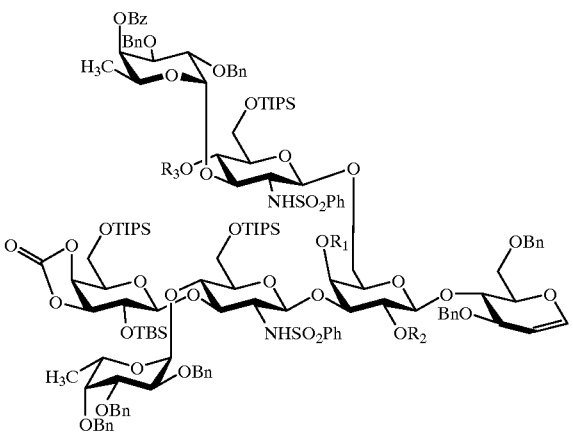

wherein $R_1$ and $R_2$ are Ac and $R_3$ is H, which comprises:

(a)(i) monoacylating a heptasaccharide glycal having the structure:

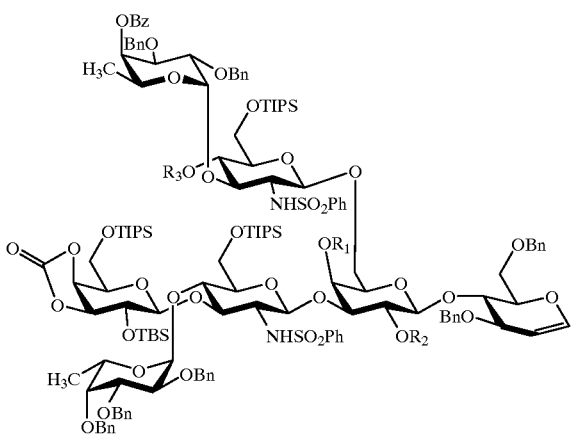

wherein $R_1$ and $R_2$ are H and R is PMB; with acyl anhydride in the presence of a catalyst under suitable conditions to form a heptasaccharide glycal monoacetate; (ii) treating the heptasaccharide glycal monoacetate formed in step (a) (i) with an acyl anhydride in the presence of a catalyst under conditions suitable to form a heptasaccharide glycal diacetate;

(iii) deprotecting the heptasaccharide glycal diacetate under suitable conditions to form the heptasaccharide glycal diacetate intermediate.

The invention encompasses the method wherein the heptasaccharide glycal is prepared by a process which comprises:

(a) (i) reacting a trisaccharide iodosulfonamide having the structure:

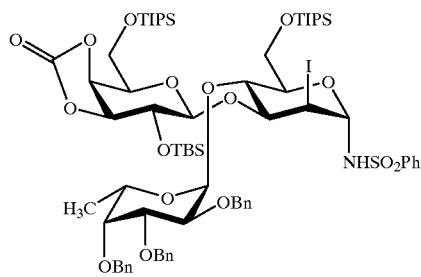

with a disaccharide stannane having the structure:

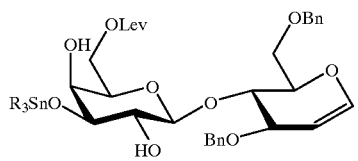

under suitable conditions; and (ii) deprotecting under suitable conditions to form a pentasaccharide glycal having the structure:

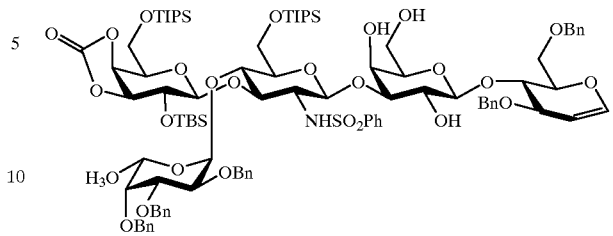

(b) coupling the pentasaccharide glycal formed in step (a) with an ethylthioglycoside having the structure:

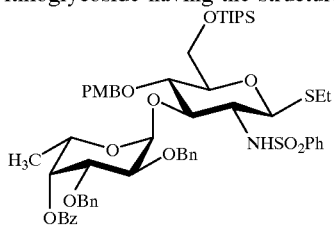

under suitable conditions to form the heptasaccharide glycal. The invention encompasses the method wherein the conditions of the reacting step comprise an ionizing agent.

The invention also encompasses the method wherein the ionizing agent is $AgBF_4$.

The invention further encompassses a method of preparing a protected disaccharide having the structure:

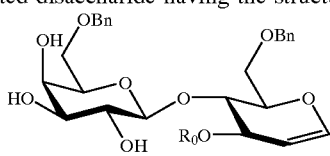

wherein $R_0$ is $C_{1-9}$ linear or branched chain alkyl, arylalkyl, trialkylsilyl, aryldialkylsilyl, diarylalkylsilyl, and triarylsilyl, which comprises:

(a)(i) epoxidizing a galactal carbonate having the structure:

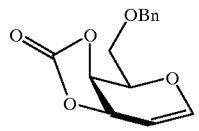

with an oxygen transfer agent under suitable conditions to form an epoxide galactal; and (ii) coupling the epoxide galactal formed in step (a) (i) with a doubly protected galactal having the structure:

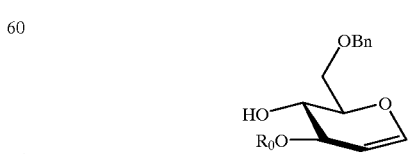

under suitable conditions to form a disaccharide carbonate having the structure:

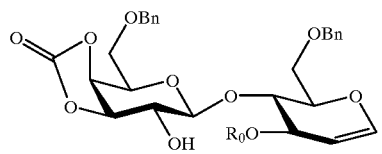

and (b) saponifying the disaccharide carbonate formed in step (a) (ii) under suitable conditions to form the protected disaccharide.

The invention encompasses the method wherein the galactal carbonate is prepared by a process which comprises:

(a) protecting a galactal having the structure:

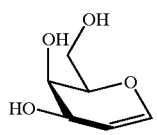

with an alkylating agent under suitable conditions to form a first protected galactal; and (b) treating the first protected galactal formed in step (a) with a carbonate-forming reagent under conditions suitable to form the galactal carbonate. The invention further provides the method wherein the carbonate-forming reagent is $(Im)_2CO/DMAP$.

The invention also provides a method wherein the doubly protected galactal is prepared by a process which comprises:

(a) protecting a second galactal having the structure:

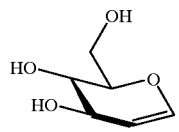

with an alkylating agent under conditions suitable to form a second protected galactal; and (b) protecting the second protected galactal formed in step (a) with an alkylating agent which may be the same or different from that of step (a) under conditions suitable to form the doubly protected galactal. The invention encompasses the method wherein each alkylating agent is independently an alkyl, arylalkyl, trialkylsilyl, aryldialkylsilyl, diarylalkylsilyl or triarylsilyl halide or triflate. The invention further encompasses the method wherein the alkylating agent is benzyl bromide. In one example, the alkylating agent is TES-Cl. The method also encompasses the method wherein the oxygen transfer agent is DMDO. The method further encompasses conditions for the coupling step comprising $ZnCl_2$ in THF. The additionally encompasses conditions for the saponifying step comprising $K_2CO_3$ in methanol.

The present invention further provides a method of preparing an ethylthioglycoside having the structure:

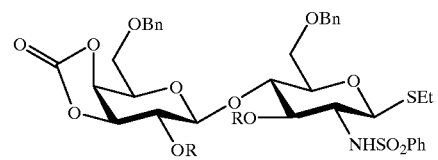

wherein R is $C_{1-9}$ linear or branched chain alkyl, arylalkyl, trialkylsilyl, aryldialkylsilyl, diarylalkylsilyl, and triarylsilyl, which comprises:

(a) treating a protected disaccharide carbonate having the structure:

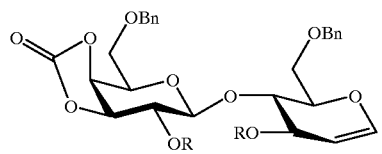

with an iodosulfonamidating agent under suitable conditions to form a disaccharide iodosulfonamidate having the structure:

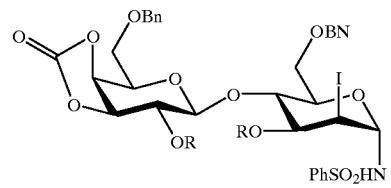

and (b) reacting the disaccharide iodosulfonamidate formed in step (a) with ethylthiol under suitable conditions to form the ethylthioglycoside.

The invention also provides a method wherein the protected disaccharide carbonate is prepared by a process which comprises alkylating a disaccharide carbonate having the structure:

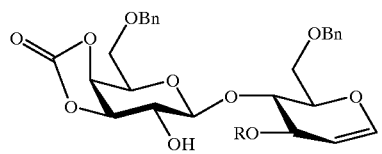

with an alkylating agent under suitable conditions to form the protected disaccharide carbonate. The method encompasses within the scope of the method any alkylating agent selected from the group including an alkyl, arylalkyl, trialkylsilyl, aryldialkylsilyl, diarylalkylsilyl or triarylsilyl halide or triflate. An example of the alkylating agent is TES-Cl. An example of the the iodosulfonamidating agent is $I(coll)_2ClO_4$ and $PhSO_2NH_2$.

The present invention provides a method of preparing an ethylthioglycoside having the structure:

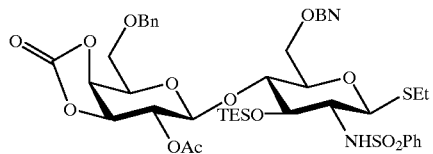

which comprises:
(a) acylating a disaccharide carbonate having the structure:

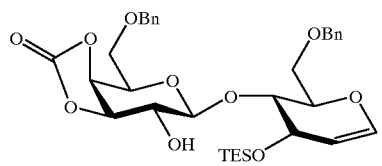

under suitable conditions to form an acylated disaccharide carbonate having the structure:

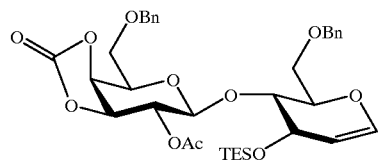

(b) treating the acylated disaccharide carbonate formed in step (a) with an iodosulfonamidating agent under suitable conditions to form a disaccharide iodosulfonamidate having the structure:

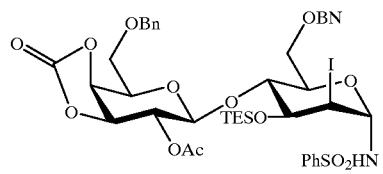

and
(c) reacting the iodosulfonamidate formed in the step (b) with ethyl thiol under suitable conditions to form the ethylthioglycoside. The invention encompasses the method wherein the conditions of the acylating step comprise acetic anhydride/pyridine. An example of the iodosulfonamidating agent is $I(coll)_2ClO_4$ and $PhSO_2NH_2$.

The present invention also provides a method of preparing a protected hexasaccharide having the structure:

which comprises:
(a) reacting a protected tetrasaccharide having the structure:

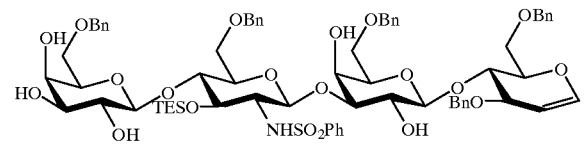

with an ethylglycoside having the structure:

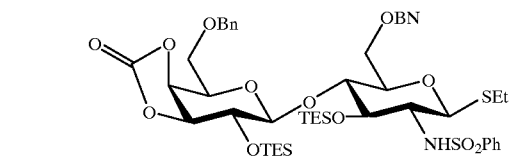

under suitable conditions to form a hexasaccharide intermediate; and
(b) acetylating the hexasaccharide intermediate formed in step (a) under suitable conditions to form the protected hexasaccharide.

The invention provides a method wherein the protected tetrasaccharide is prepared by a process which comprises:
(a) coupling an ethythioglycoside having the structure:

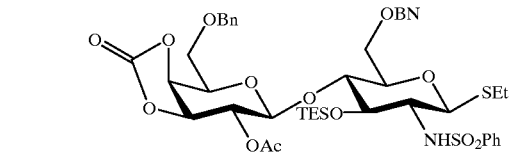

with a protected disaccharide having the structure:

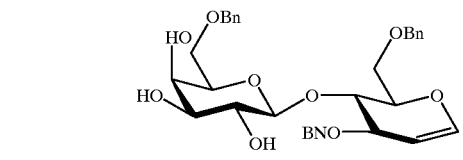

under suitable conditions to form a protected tetrasaccharide carbonate; and
(b) saponifying the protected tetrasaccharide carbonate formed in step (a) under suitable conditions to form the protected tetrasaccharide. The invention encompasses the method wherein the conditions of the coupling step comprise MeOTf/MS. The invention also encompasses the method wherein the conditions of the saponifying step comprise $K_2CO_3$ in methanol.

The present invention provides a method of preparing a protected nonasaccharide having the structure:

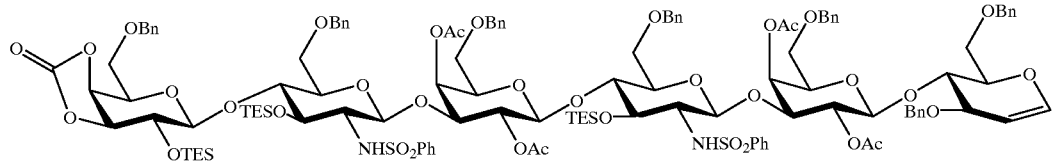

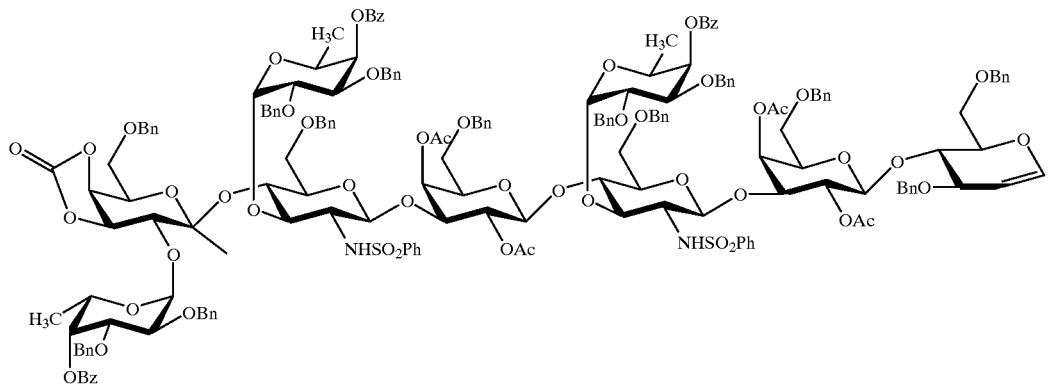

which comprises:

(a) deprotecting a protected hexasaccharide having the structure:

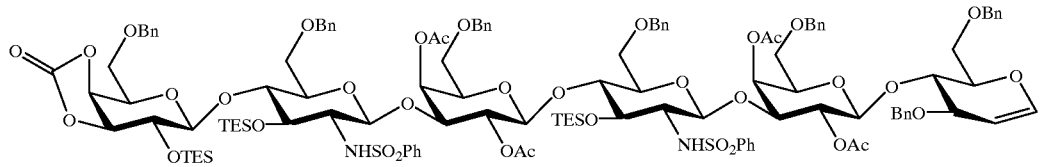

under suitable conditions to form a partially deprotected hexasaccharide; and (b) coupling the partially deprotected hexasaccharide formed in step (a) with a fucosylfluoride having the structure:

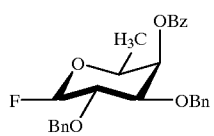

in the presence of an organometallic reagent under suitable conditions to form the protected nonasaccharide. The method encompasses conditions of the deprotecting step comprising a fluoride salt. The fluoride salt may be a tetraalkylammonium fluoride. Specifically, the fluoride salt may be TBAF. The invention encompasses the method wherein the organometallic reagent is Sn(OTf)$_2$/DTBP.

The present invention also provides a method of preparing a protected nonasaccharide ceramide having the structure:

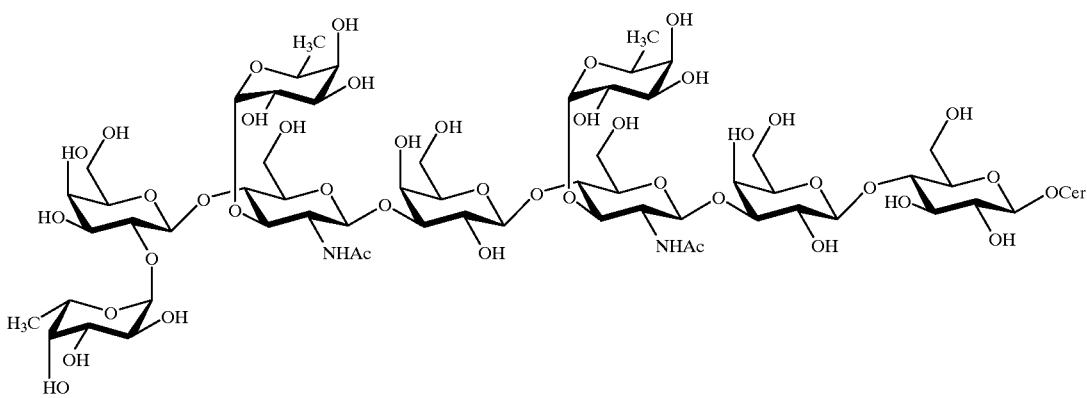

which comprises:

(a) epoxidizing a protected nonasaccharide having the structure:

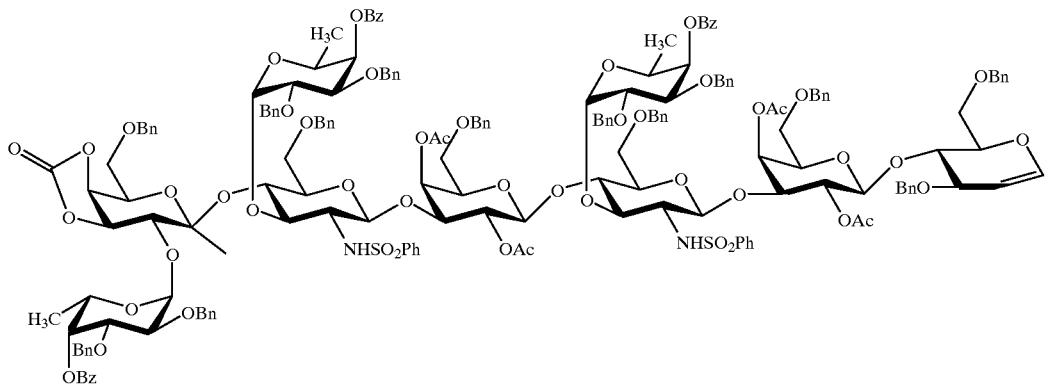

with an oxygen transfer agent under suitable conditions to form a protected nonasaccharide epoxide;

(b) coupling the protected nonasaccharide epoxide formed in step (a) with an azide having the structure:

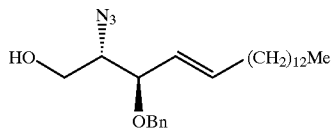

under suitable conditions to form a nonasaccharide azide intermediate;

(c) reductively acylating the azide intermediate with palmitic anhydride under suitable conditions to form a protected nonasaccharide ceramide;

(d) reducing the protected nonasaccharide ceramide formed in step (c) under suitable conditions to form a deprotected nonasaccharide ceramide;

(e) acylating the deprotected nonasaccharide ceramide under suitable conditions to form an acylated nonasaccharide ceramide; and (f) saponifying the acylated nonasaccharide ceramide under suitable conditions to form the nonasaccharide ceramide. The invention encompasses the method wherein the oxygen transfer agent is DMDO. The invention also encompasses the method wherein the conditions of the coupling step comprise $ZnCl_2$. The method further encompasses use of an azide intermediate which is reductively acylated in step (c) in the presence of Lindlar's catalyst. The invention further encompasses the method wherein conditions of the saponifying step comprise MeONa in methanol.

The present invention provides a method of inducing antibodies in a subject, wherein the antibodies are capable of specifically binding with epithelial tumor cells cells, which comprises administering to the subject an amount of a compound which contains a determinant having a structure selected from the group consisting of:

which amount is effective to induce antibodies. In one embodiment, the invention encompasses a method wherein the compound is bound to a suitable carrier protein, said compound being bound either directly or by a cross-linker selected from the group consisting of a succinimide and an $M_2$ linker. Preferably, the compound contains a KH-1 or N3 epitope. The method specifically encompasses use of the carrier protein selected from the group consisting of bovine serum albumin, polylysine or KLH. The method also encompassses the method disclosed which further comprises co-administering an immunological adjuvant. In particular, the adjuvant may include bacteria or liposomes. Specifically, the adjuvant may be *Salmonella minnesota* cells, bacille Calmette-Guerin or QS21. In a certain embodiment, the method includes use of the compound having the structure:
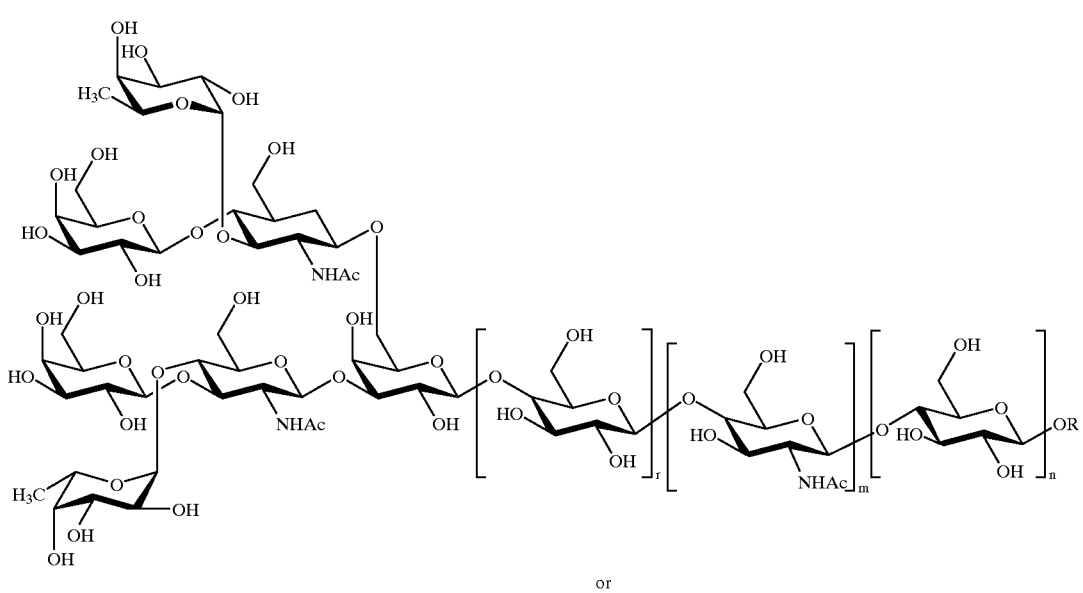
(a)
or
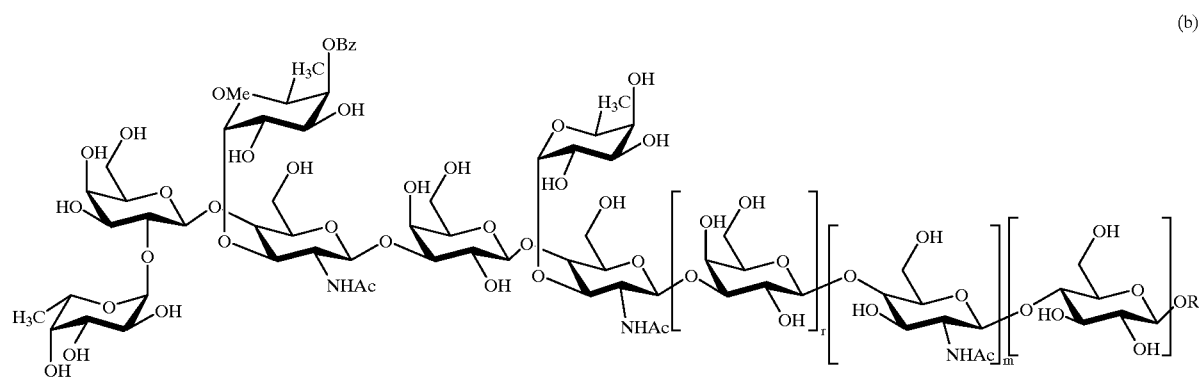
(b)
or
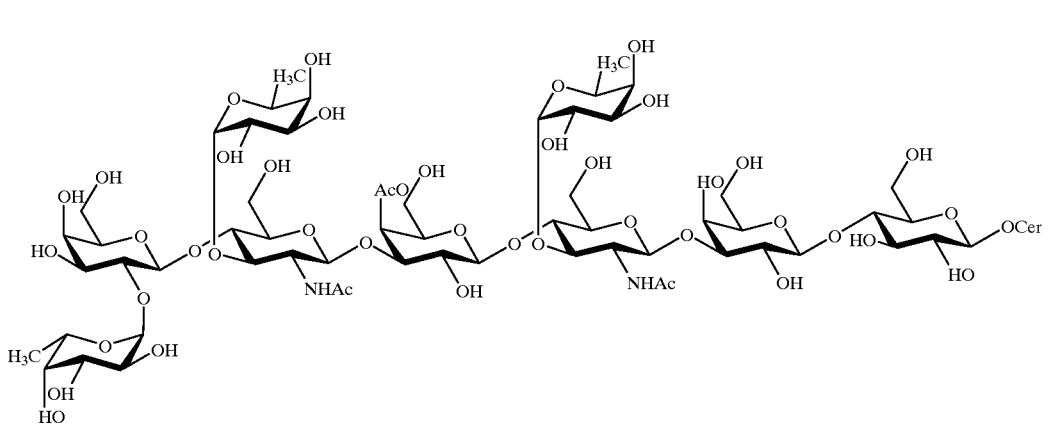
(c)

wherein R is H, substituted or unsubstituted alkyl, aryl or allyl, or an amino acyl moiety, an amino acyl residue of a peptide, an amino acyl residue of a protein, which amino acyl moiety or residue bears an ω-amino group or an ω-(C=O)— group, which group is linked to O via a polymethylene chain having the structure —(CH$_2$)$_s$—, where s is an integer between about 1 and about 9, or a moiety having the structure:

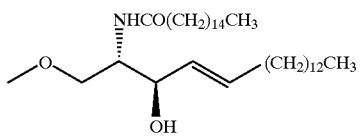

and wherein r, m and n are independently 0, 1, 2 or 3. The invention encompasses the method wherein the subject is in clinical remission or, where the subject has been treated by surgery, has limited unresected disease.

In the practice of the invention, the method encompasses the induction of antibodies capable of specifically binding with gastrointestinal tumor cells, colon tumor cells, lung tumor cells, prostate tumor cells.

In addition, the invention provides a method of treating a subject suffering from an epithelial cell cancer, which comprises administering to the subject an amount of a compound which contains a determinant having a structure selected from the group consisting of:

(a)

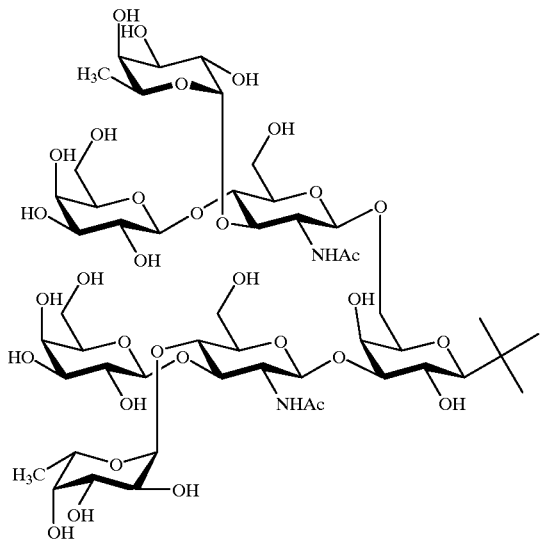

and which amount is effective to treat the cancer. The method may be practiced wherein the compound is bound to a suitable carrier protein, said compound being bound either directly or by a cross-linker selected from the group consisting of a succinimide and an M$_2$ linker. Faborably, the carrier protein is bovine serum albumin, polylysine or KLH, and the compound contains a KH-1 or N3 epitope. The method may further comprise co-administering an immunological adjuvant. The adjuvant is bacteria or liposomes. In particular, the adjuvant is *Salmonella minnesota* cells, bacille Calmette-Guerin or QS21.

The invention further provides a method of preventing recurrence of epithelial cell cancer in a subject which comprises vaccinating the subject with a compound which contains a determinant having the structure:

(b)

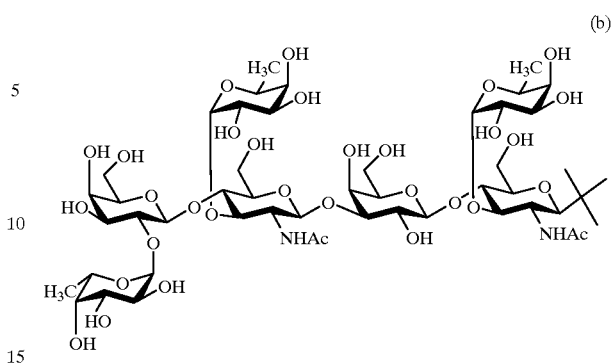

(a)

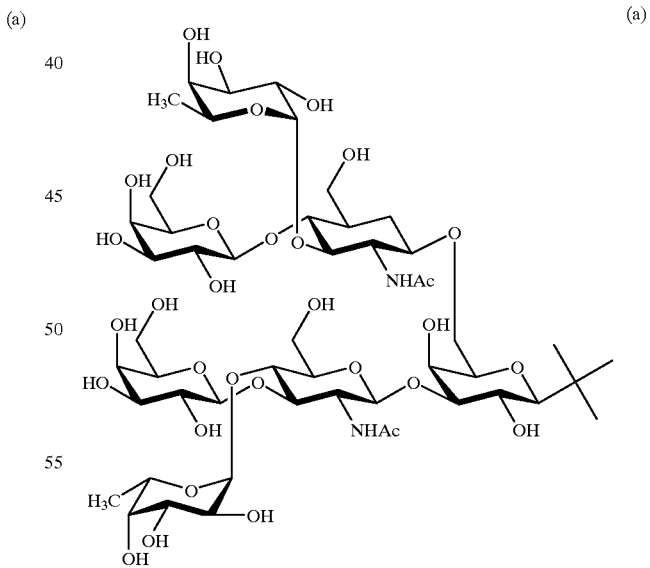

and

-continued

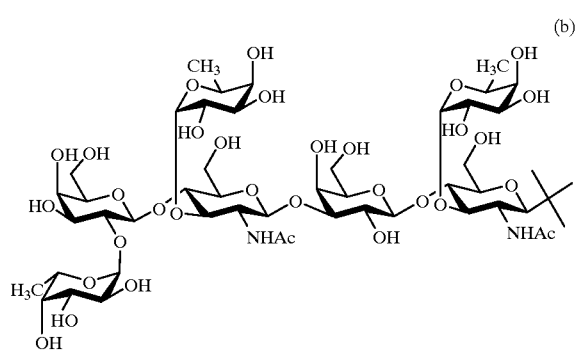

(b)

which amount is effective to induce the antibodies. The invention encompasses the method wherein the compound is bound to a suitable carrier protein. The method specifically encompasses use of any effective carrier protein including bovine serum albumin, polylysine or KLH. In addition, the method may further comprises co-administering an immunological adjuvant. The adjuvant may be bacteria or liposomes. In particular, the adjuvant may be *Salmonella minnesota* cells, bacille Calmette-Guerin or QS21.

The method may carried out using a compound selected from the group consisting of:

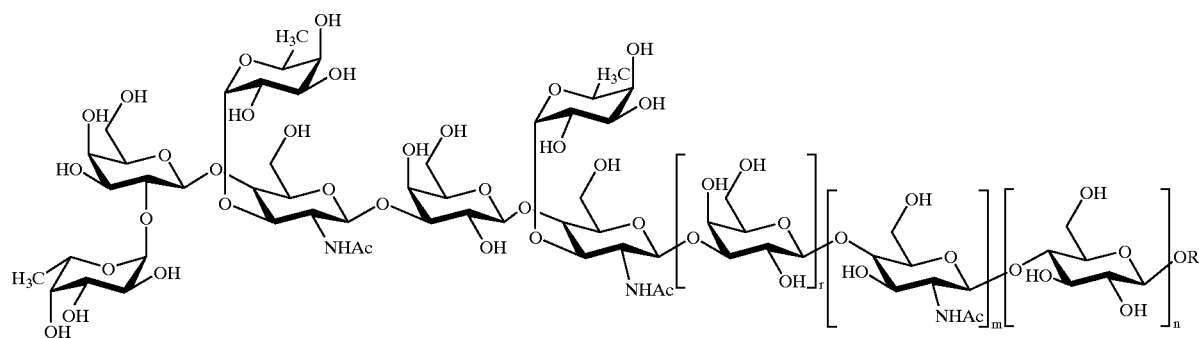

(a)

and

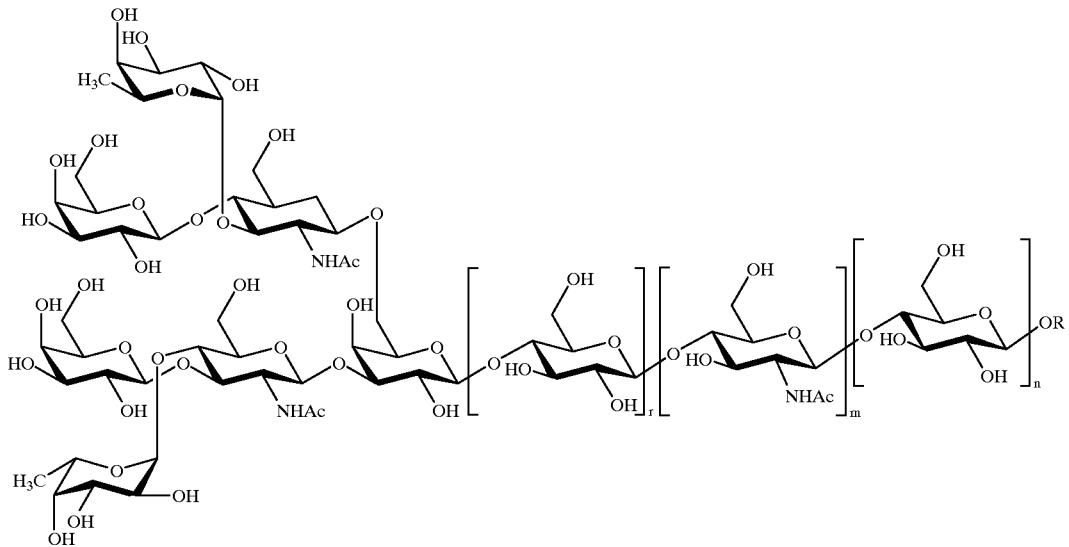

(b)

wherein R is H, substituted or unsubstituted alkyl, aryl or allyl, or an amino acyl moiety, an amino acyl residue of a peptide, an amino acyl residue of a protein, which amino acyl moiety or residue bears an ω-amino group or an ω-(C=O)— group, which group is linked to O via a polymethylene chain having the structure —(CH$_2$)$_s$—, where s is an integer between about 1 and about 9, or a moiety having the structure:

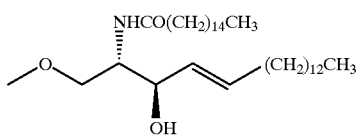

and wherein r, m and n are independently 0, 1, 2 or 3.

The processes of the present invention for preparing KH-1 and N3 anitgens and analogues thereof and intermediates thereto encompass the use of various alternate protecting groups known in the art. Those protecting groups used in the disclosure including the Examples below are merely illustrative. One of ordinary skill would understand how to substitute equivalent protecting groups for those illustrated.

The subject invention also provides pharmaceutical compositions for treating cancer comprising any of the analogues of KH-1 or N3 antigens as disclosed herein, optionally in combination with a pharmaceutically suitable carrier.

The subject invention further provides a method of treating cancer in a subject suffering therefrom comprising administering to the subject a therapeutically effective amount of any of the analogues of KH-1 or N3 antigens disclosed herein and a pharmaceutically suitable carrier.

The invention provides a method of preventing recurrence of an epithelial cell cancer in a subject which comprises vaccinating the subject with a compound which contains a determinant having the structure:

(a)

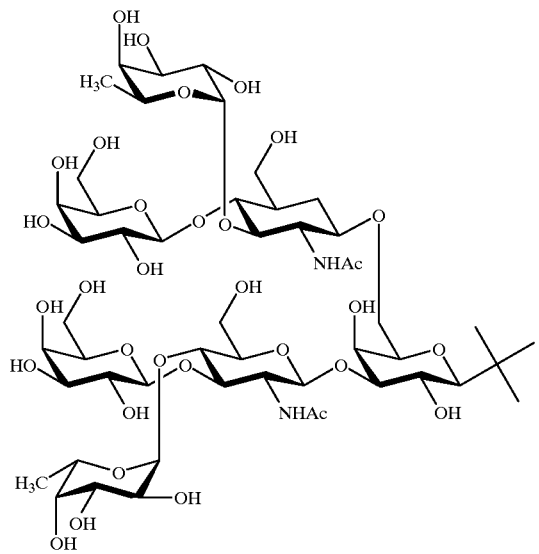

and which amount is effective to prevent recurrence of an epithelial cell cancer.

The invention provides a composition comprising a compound which contains a determinant having a structure selected from the group consisting of:

(a)

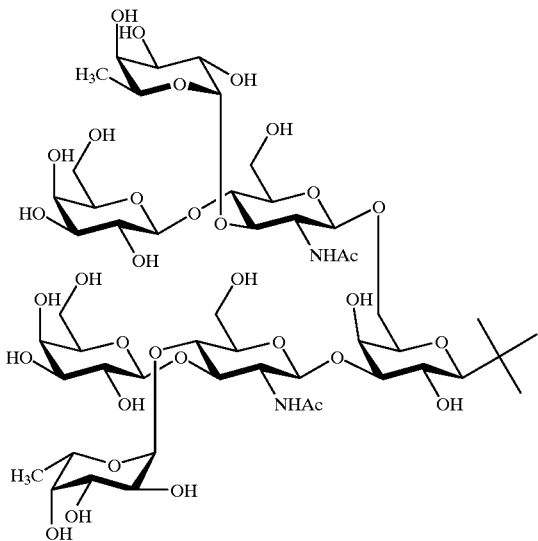

and (b)

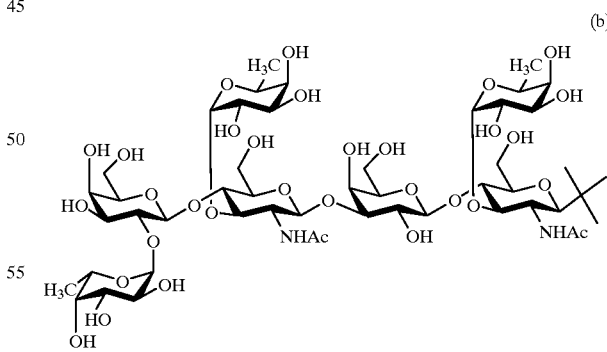

and optionally an immunological adjuvant and/or a pharmaceutically acceptable carrier.

The invention also provides the composition wherein the compound is bound to a suitable carrier protein, said compound being bound either directly or by a cross-linker selected from the group consisting of a succinimide and an M$_2$ linker. The composition is also provided wherein the carrier protein is bovine serum albumin, polylysine or KLH.

(b)

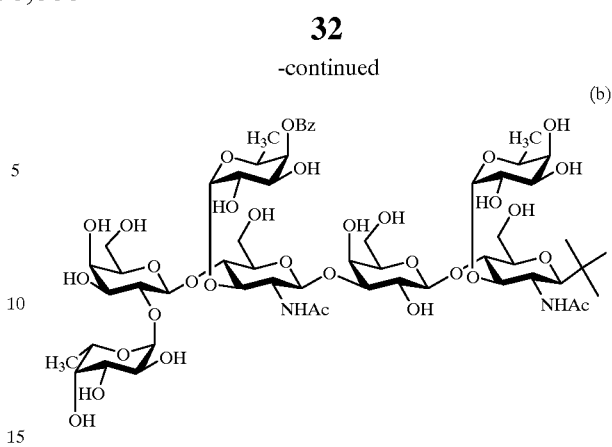

In particular, the composition is characterized wherein the compound contains a KH-1 or N3 epitope.

Additionally, the composition is provided wherein the immunological adjuvant is bacteria or liposomes. The adjuvant may be *Salmonella minnesota* cells, bacille Calmette-Guerin or QS21.

Favorably, the composition is provided wherein the compound has the structure:

wherein R is H, substituted or unsubstituted alkyl, aryl or allyl, or an amino acyl moiety, an amino acyl residue of a peptide, an amino acyl residue of a protein, which amino acyl moiety or residue bears an ω-amino group or an ω-(C=O)— group, which group is linked to O via a polymethylene chain having the structure —(CH$_2$)$_s$—, where s is an integer between about 1 and about 9, or a moiety having the structure:

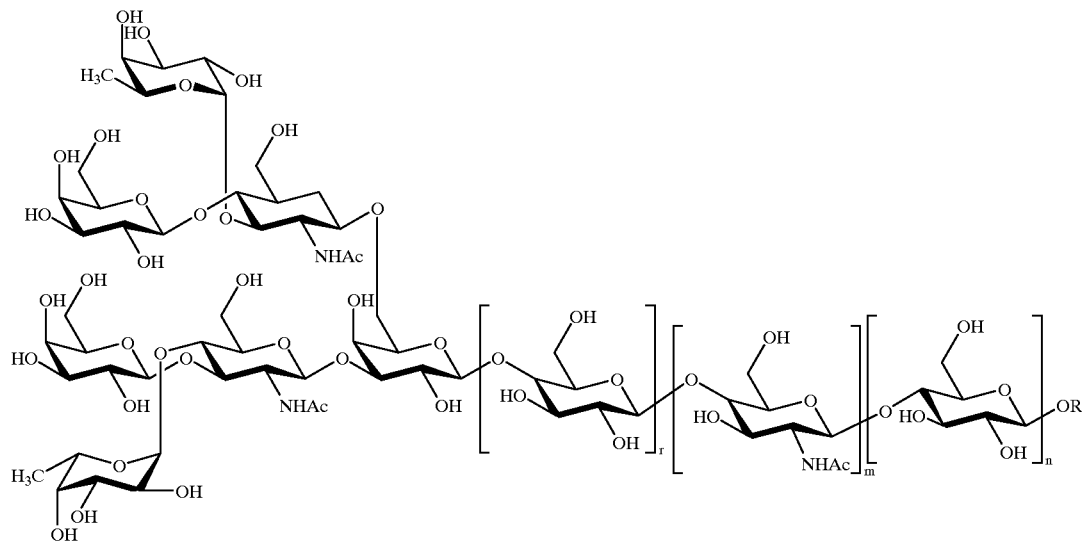

(a)

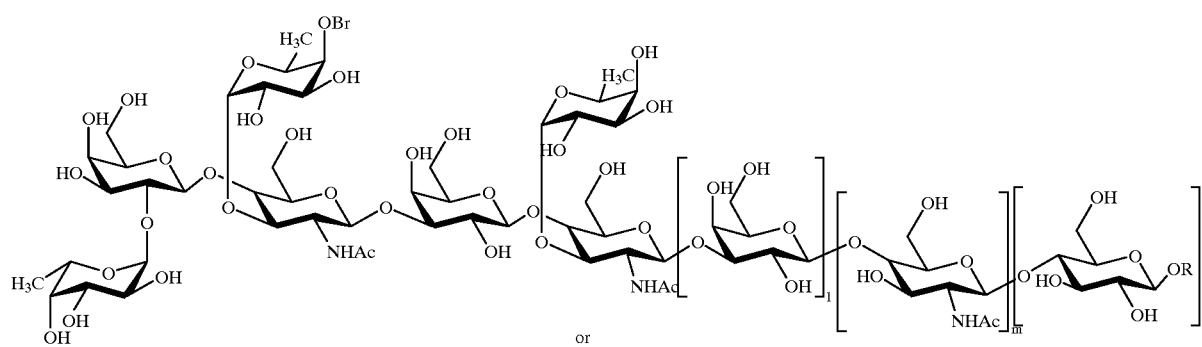

(b)

or

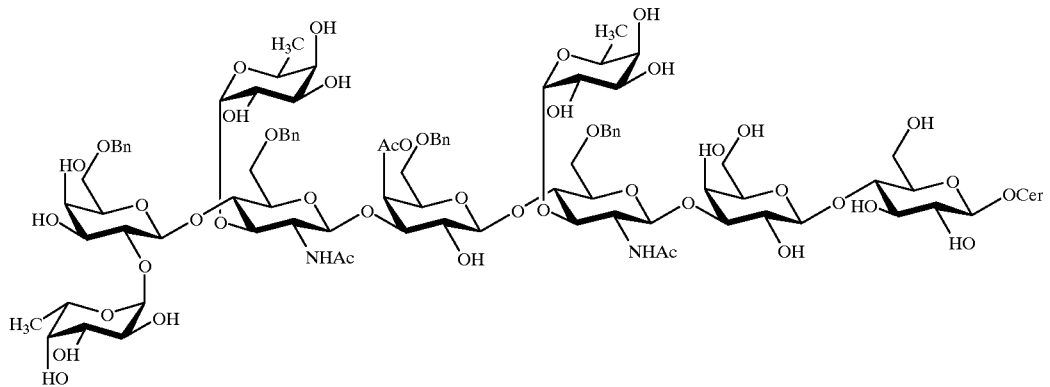

(c)

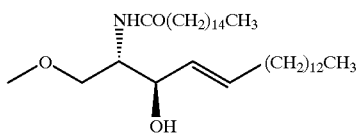

and wherein r, m and n are independently 0, 1, 2 or 3.

Utilities

The compounds taught above which are related to KH-1 and N3 cell-surface antigens are capable of preventing recurrence of various types of epithelial cancer in a subject, including lung, gastrointestinal, prostate and colon cancers, and inducing antibodies useful as a vaccine in the treatment of such types of cancer, both in vivo and in vitro. Thus, these antigens and analogues thereof are useful to treat, prevent or ameliorate such cancers in subjects suffering therefrom.

The magnitude of the therapeutic dose of the compounds of the invention will vary with the nature and severity of the condition to be treated and with the particular compound and its route of administration. In general, the daily dose range for anticancer activity or antibody induction lies in the range of 0.001 to 25 mg/kg of body weight in a mammal, preferably 0.001 to 10 mg/kg, and most preferably 0.001 to 1.0 mg/kg, in single or multiple doses. In unusual cases, it may be necessary to administer doses above 25 mg/kg.

Any suitable route of administration may be employed for providing a mammal, especially a human, with an effective dosage of a compound disclosed herein. For example, oral, rectal, topical, parenteral, ocular, pulmonary, nasal, etc., routes may be employed. Dosage forms include tablets, troches, dispersions, suspensions, solutions, capsules, creams, ointments, aerosols, etc.

The pharmaceutical compositions of the present invention comprise a compound containing any of the KH-1 and N3 antigens of the subject invention, as an active ingredient, and may also contain a pharmaceutically acceptable carrier and, optionally, other therapeutically active ingredients.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixers and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques. In addition to the dosage forms described above, the compounds of the invention may be administered by controlled release means and devices.

Pharmaceutical compositions of the present invention suitable for oral administration may be prepared as discrete units such as capsules, cachets or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent or surface active or dispersing agent. Molded tablets may be made by molding in a suitable machine, a mixture of the powdered compound moistened with an inert liquid diluent.

The present invention will be better understood from the Experimental Details which follow. However, one skilled in the art will readily appreciate that the specific methods and results discussed are merely illustrative of the invention as described in the claims which follow thereafter.

EXAMPLE 1

6-o-Benzyl-3,4-O-carbonate-galactal (3): To a solution of 3,4-carbonate-galactal (5.36 g, 34.37 mmol) in dry DMF (50 mL) at 0° C. was added benzyl bromide (12.26 mL, 103.0 mmol), followed by NaH (60% oil dispersion, 1.5 gm. 1.1 eq). The reaction was stirred for 1 hr, diluted with $CHCl_3$ (50 mL) and then brine solution (20 mL) was added and stirred for 5 min. The organic layer was separated, dried ($MgSO_4$), concentrated, and subjected to chromatographic purification (1:1, Hex:EA) to obtain compound 3 (85%) as a syrup: $[\alpha]^{23}_D$=-92.0 (c 1.0, $CHCl_3$); FTIR (thin film) 3030,2875, 1797, 1647, 1496, 1453, 1371, 1244, 1164, 1110, 1010, 837, 699 $cm^{-1}$; $^1$H NMR (400 MHz, $CDCl_3$ δ 3.7–3.9 (m, 2H, H-6), 4.08 (bt, 1H, J=7.36 Hz, H-5), 4.58 (s, 2H, —$CH_2Ar$), 4.90 (d, 1H, J=7.76 Hz, H-4), 4.93 (bm, 1H, H-3), 5.14 (dd, 1H, J=3.16 Hz, J=7.72 Hz, H-2), 6.66 (d, 1H, J=6.24 Hz, H-1), 7.28–7.45 (m, 5H, Ar—H); C NMR (400 MHz, $CDCl_3$ δ 67.97, 68.74, 72.41, 73.14, 73.66, 97.97, 127.77, 127.93, 128.44, 137.18, 149.06, 153.98.

EXAMPLE 2

6-O-Benzylglucal (3'): To a solution of a glucal (10 g, 68.42 mmol) in a dry DMF (200 mL) was added at -40° C. LHMDS (1.0 M soln in THF, 75.26 mL, 1.1 eq) dropwise, followed by BnBr (8.18 mL, 68.42 mmol). The solution was stirred mechanically for 6 hrs allowing the temperature to rise to 0° C. At room temperature, a sat'd solution of ammonium chloride (50 mL) was added, followed by EtOAc (200 mL). The organic layer was separated; the aqueous layer was extracted with EtOAc (3×50 mL). Combined organic layers were washed with brine (50 mL), water (50 mL), dried with ($MgSO_4$), filtered, concentrated and purified by column chromatgraphy (1:1 Hex: EtOAc) to obtain compound 3' as a syrup: $[\alpha]^{23}_D$=+11.0 (c 1.0, $CHCl_3$); FTIR (thin film): 3342, 2871, 1642, 1656, 1231, 1101, 1027, 851, 738 $cm^{-1}$; $^1$H NMR (400 MHz, $CDCl_3$) δ 3.6–3.85 (m, 5H,), 4.06 (d, 1H, J=4.0 Hz, —OH), 4.11 (bt, 1H, H-3), 4.46 (d, 1H, J=12.0 Hz, —$CH_2Ar$), 4.52 (d, 1H, J=12.0 Hz, —$CH_2Ar$), 4.57 (dd, 1H, J=1.84 Hz, J=5.96 Hz, H-2). 6.21 (d, 1H, J=5.96 Hz, H-1), 7.15–7.35 (m, 5H, Ar—H); C NMR (400 MHz, $CDCl_3$) δ 69.06, 69.63, 70.28, 73.427, 76.95, 102.72, 127.29, 127.55, 128.21, 128.24, 137.60, 137.75, 143.86.

EXAMPLE 3

6-O-Benzyl-3-O-triethylsilylglucal (4): To a solution of compound 3 (5 g, 21.16 mmol) in dry $CH_2Cl_2$ (50 mL) was added imidazole (1.72 g, 25.39 mmol), DMAP (10 mg). At 0° C. TESCl (3.90 mL, 23.27 mmol) was added dropwise. The reaction mixture was stirred for 9 hrs, washed with water (2×10 mL) and brine (10 mL). The organic layer was separated and dried (MgSO$_4$), concentrated and purified by column chromatography (20% EA in hexane) to obtain 4 (5.47 mg ,73%) as a syrup: $[\alpha]^{22}{}_D$+44.0 (c 1.0, CHCl$_3$); FTIR (thin film) 3468, 3030, 2953, 2875, 1644, 1453, 1237, 1086, 871, 737 cm$^{-1}$; $^1$H NMR (400 MHz, CDCl$_3$) δ 0.55 (q, 6H, J=7.90 Hz, —SiCH$_2$CH3), 0.88 (t, 9H, J=7.90 Hz, —SiCH2CH$_3$), 2.47 (d, 1H, J=4.12 Hz, —OH), 3.6–3.75 (m, 3H, 2H-6, H-4), 4.13 (bd, 1H, J=6.4 Hz, H-3), 4.47 & 4.52 (2d, 2H, J=12.00 Hz, —CH$_2$Ar), 4.55 (dd, 1H, J=2.24 Hz, J=6.16 Hz, H-2), 6.21 (d, 1H, J 5.96 Hz, H-1), 7.10–7.40 (m, 5H, Ar-H); $^{13}$C NMR (400 MHz, CDCl$_3$) δ 4.84, 6.66, 69.05, 69.64, 70.56, 73.47, 76.97, 103.44, 127.59, 127.64, 128.27, 137.78, 143.33.

EXAMPLE 4

3,6,6'-Tri-O-benzyl-4',5'-carbonate-lactal (7): To a solution of compound 3 (3.00 gm, 11.43 mmol) in a dry CH$_2$Cl$_2$ (20 mL) at 0° C. was added 3,3-dimethyldioxirine (300 mL, 0.08 M solution in acetone). The reaction was stirred at 0° C. for 1 h. The organic solvent was evaporated in a stream of N$_2$ gas. The residue was dried in vacuum for 10 minutes. The resulting anhydro sugar was dissolved in a solution of the compound 3,6-dibenzylglucal (5.29 gm, 17.15 mmol) in a dry THF (30 mL). At 0° C. a 1.0 M solution of ZnCl$_2$ in ether (5.71 mL, 0.5 eq) was added. The reaction was stirred at room temperature for 24 h, diluted with EtOAc (50 mL), washed with a sat'd solution of NaHCO$_3$ (2×10 mL). The organic layer was separated, dried (MgSO$_4$) and purified by chromatography using EA:Hexane (1:1) to obtain compound 7, 3.3 g (48%) (60% wrt recovered SM) as a syrup: $[\alpha]^{22}{}_D$-38.0 (c 1.0, CHCl$_3$); FTIR (thin film) 3437, 3029, 2871, 1804, 1648, 1453, 1367, 1166, 1097, 1027, 739, 697 cm$^{-1}$; $^1$H NMR (400 Mhz, CDCl$_3$) δ 3.55–3.62 (m, 2H), 3.62–3.70 (m, 2H), 3.70–3.78 (m, 2H), 3.95–4.11 (m, 2H), 3.95–4.11 (m, 2H), 4.17 (dd, 1H, J=5.36 Hz, J=7.04), 4.27 (ddd, 1H, J=1.12 Hz, J=1.73 Hz, J=5.29 Hz), 4.44 (s, 2H, —CH2Ar), 4.77 (dd, 1H, J=2.48 Hz, J=6.12 Hz, H-2), 6.28 (d, 1H, J=6.04 Hz, H-1), 7.10–7.40 (m, 15H, Ar—H); $^{13}$C NMR (400 MHz, CDCl$_3$) 68.00, 68.09, 70.55, 70.63, 72.20, 73.58, 73.81, 74.58, 74.82, 75.26, 76.18, 78.47, 100.17, 101.32, 127.43 (2C), 127.56, 127.72 (2C), 127.83, 127.90, 128.00 (2C), 128.31(2C), 128.37 (2C), 128.44 (2C), 137.28, 137.43, 138.29, 144.59, 153.97.

EXAMPLE 5

3,6,6'-Tri-O-benzyl-lactal (10): To a solution of compound 7 (3.00 g, 4.96 mmol) in MeOH (100 mL) was added dropwise a solution of sodium methoxide (1 mL, 25% by wt in MeOH). The reaction was stirred for 1 h, and the solvent was evaporated. The syrup obtained was rapidly purified by column chromatography (2.5% MeOH in EtOAc) to obtain 2.68 g (91%) of 10 as syrup: $[\alpha]^{22}{}_D$-14.0 (c 1.0, CHCl3); FTIR (thin film) 3415, 3029, 2867, 1647, 1453, 1246, 1068, 735 cm ; H NMR (500 MHz, CDCl$_3$) δ 3.48–3.56 (m, 2H), 3.62 (dd, 1H, J=4.80 Hz, J=8.0 Hz), 3.66–3.78 (m, 3H), 3.91 (d, 1H, J=4.4 Hz), 3.97 (dd, 1H, J=4.0 Hz, J=8.8 Hz), 4.18–4.28 (m, 4H), 4.47 (s, 2H, —CH2Ar), 4.52 (d, 1H, J=8.0 Hz), 5.59 (s, 1H, —CH2Ar), 4.57–4.65 (m, 2H, —CH2Ar), 4.85 (dd, 1H, J=2.4 Hz, H-2), 6.41 (d, 1H, J=4.8 Hz, H-1), 7.20–7.45 (m, 15H, Ar—H); $^{13}$C NMR (400 MHz, CDCl$_3$) δ 67.92, 68.86, 69.19, 69.82, 71.53, 73.35(2C), 73.39, 73.42, 73.87, 76.26, 99.82, 103.30, 127.35, 127.42, 127.59, 127.74, 128.19, 128.29, 137.72, 137.81, 138.52, 144.57.

EXAMPLE 6

Monosilylated lactal (6): To a solution of compound 3 (3.00 gm, 11.43 mmol) in a dry CH$_2$Cl$_2$ (20 mL) at 0° C. was added 3,3-dimethyldioxirine (300 mL, 0.08 M solution in acetone). The reaction was stirred at 0° C. for 1 h, and the organic solvents were evaporated in a N$_2$ gas stream. The residue was dried in vacuum for 10 minutes. The resulting anhydro sugar was dissoved in a solution of compound 4 (6 gm, 9.2 mmol) in a dry THF (30 mL), at 0° C. was added a 1.0 M solution of ZnCl$_2$ in ether (6 g, 0.5 eq). Reaction was stirred at room temperature for 24 h. Diluted with EtOAc (50 mL) , washed with sat. solution of NaHCO$_3$ (2×10 mL), organic olayer was separated, dried (MgSO$_4$) submitted for chromatography EA: Hexane (2:3) to obtain compound 6 (4.8 g 66%) (81% wrt recovered 7) as a syrup: $[\alpha]^{22}{}_D$-25.0 (c 1.0, CHCl3) ; IR (thin film) 3439, 3030, 2910, 1804, 1725, 1647, 1453, 1371, 1243, 1074, 847, 741 cm$^{-1}$; 1H NMR (CDCl3, 400 MHz) δ 0.58 (q, 6H, J=8.0 Hz, —SiCH2CH3), 0.92 (t, 9H, J 8.0 Hz, —SiCH2CH3), 3.51 (d, 1H, J=2.8 Hz, —OH), 3.62 (ddd, 1H, J=2.8 Hz, J=7.2 Hz, J=7.2 Hz, H-2'), 3.65.3.75 (bm, 3H), 3.85 (m, 1H), 3.93 (dd, 1H, J=4.92 Hz, J=11.24 Hz), 3.99 (bt, 1H, J=5.32 Hz, J=6.48 Hz), 4.09 (bm, 1H), 4.27(bt, 1H, J=4.16 Hz), 4.48–4.68 (m, 6H, —CH2Ar), 4.70 (dd, 1H, J=3.36 Hz, J=6.16 Hz, H-2), 4.74 (dd, 1H, J=1.8 Hz, J=7.16 Hz, H-4), 6.32 (d, 1H, J=6.04, H-1), 7.2–7.4 (m, 10H, Ar—H); C (500 MHz, CDCl$_3$) δ 4.75, 6.67, 65.65, 67.79, 67.93, 70.42, 71.49, 73.43, 73.58, 74.46, 75.27, 75.42, 78.05, 99.94, 102.61, 127.79, 127.85, 128.14, 128.33, 137.36, 137.53, 143.00, 153.96.

EXAMPLE 7

Acetylated silyl lactal: To a solutiuon of compound 6 (3.5 g, 5.50 mmol) in CH$_2$Cl$_2$ (30 mL) was added pyridine (3 mL), Ac$_2$O (3 mL) and DMAP (cat). The reaction was stirred overnight, and then diluted with EtOAc (50 mL), washed with a sat'd solution of CuSO$_4$ (3×10 mL), water (1×10 mL), NaHCO$_3$ (2×10 mL), and brine (1×10 mL). The organic layer was separated, dried, and concentrated. The residue was purified by chromatography (1:1, Hex:EA) to obtain 6' in quantitative yield; $[\alpha]^{23}{}_D$-42.0 (c 1.0, CHCl$_3$); IR (film) 2954, 2875, 1809, 1755, 1646, 1454, 1222, 1060, 743 cm$^{-1}$; $^1$H NMR (CDCl$_3$) δ 0.58 (q, 6H, J=7.92 Hz, —SiCH$_2$CH$_3$), 0.92 (t, 9H, J=7.92 Hz, —SiCH$_2$CH$_3$), 2.06 (s, 3H, —COCH$_3$), 3.63 (dd, 1H, J=2.92 Hz, J=10.92 Hz, H-5), 3.70 (bd, 2H, J=10.52 Hz, 2H-6), 3.85 (dd, 1H, J=6.08 Hz, J=10.92, H-5'), 3.9–4.0 (m, 2H, 2H-6'), 4.10–4.2 (m, 2H), 4.5–4.6 (m, 4H, 2-CH$_2$Ar), 4.64 (dd, 1H, J=3.96 Hz, 8.0 Hz, H-3'), 4.71 (dd, 1H, J=4.24 Hz, J=5.84 Hz, H-2), 4.84 (dd, 1H, J=1.04 Hz, J=8.08 Hz, H-4'), 4.90 (d, 1H, J=4.60 Hz, H-1'), 4.99 (t, 1H, J=4.20 Hz, H-4'), 6.30 (d, 1H, J=6.16 Hz, H-1), 7.15–7.40 (m, 10H, Ar—H); $^{13}$C NMR (CDCl$_3$) δ 4.78, 6.73, 20.58, 64.78, 67.94, 67.99, 69.38, 69.50, 73.19, 73.35, 73.79, 73.92, 74.56, 74.86, 96.82, 102.27, 127.60, 127.75, 127.78, 127.93, 128.29, 128.44, 137.35, 138.01, 142.99, 153.27, 168.54.

EXAMPLE 8

Iodosulfonamide (6"): To a solution of compound 6' (2.5 gm, 3.72 mmol) (suspended with 4 A MS (3.00 g)) and benzenesulfonamide (2.92 g, 18.57 mmol) at 0° C., was added (via cannula) a solution of I$^+$ (coll)$_2$ClO$_4$$^-$ (freshly prepared from Ag(coll)ClO$_4$ (8.36 g, 18.59 mmol) and I$_2$ (4.53 g, 18.53 mmol)) in CH$_2$Cl$_2$ (40 mL). The reaction mixture was allowed to warm to r.t. and stirred for 1 hr. The mixiture was filtered through a pad of silica gel. The filtrate was washed with a sat'd solution of $Na_2S_2O_3$ (3×25 mL), followed by a sat'd solution of $CuSO_4$ (5×25 mL), and $H_2O$ (2×10 mL). The organic layer was separated and dried ($MgSO_4$), concentrated and purified by column chromatogrphy (5% EA in $CH_2Cl_2$, in a gradient elution) to obtain 6", 2.9 g (81%) as a syrup; $[\alpha]^{23}{}_D$ –30.0 (c 1.0, $CHCl_3$); IR (film) 3267, 2954, 1806, 1755, 1495, 1458, 1370, 1342, 1090, 813, 750 cm$^{-1}$; $^1H$ NMR ($CDCl_3$) δ 0.66 (m, 6H, J=7.8 Hz, —$SiCH_2$ $CH_3$) 0.95 (t, 9H, J=7.8 Hz, —$SiCH_2CH_3$), 2.04 (s, 3H, —$COCH_3$), 3.44 (dd, 1H, J=5.56 Hz, J=10.16 Hz, H-5), 3.55–3.72 (m, 4H), 3.86 (bs, 1H), 4.11 (t, 1H, J=6.96 Hz), 4.23 (bs, 1H), 4.35 (dd, 1H, J=2.28 Hz, J=9.98 Hz), 4.44 & 4.50 (2d, 2H, 11.88 Hz, —$CH_2Ar$), 4.57 (s, 2H, —$CH_2Ar$), 4.70 (bd, 1H, J=8.32Hz), 4.89 (bs, 1H), 4.95–5.0 (m, 2H), 5.25 (t, 1H, J=9.64 Hz), 5.60 (d, 1H, J=9.92 Hz), 7.2–7.5 (m, 13H, Ar—H), 7.88 (d, 2H, J=7.72 Hz, Ar—H); $^{13}C$ NMR ($CDCl_3$) δ 4.93, 6.95, 20.64, 67.49, 67.86, 68.40, 68.46, 71.91, 72.57, 73.33, 73.94, 75.20, 79.30, 126.39, 127.35, 127.67, 127.85, 127.98, 128.09, 128.36, 128.54, 128.58, 129.10, 132.35, 132.68, 137.14, 137.91, 141.36, 153.60, 168.69.

EXAMPLE 9

Thiodonor (9): To a solution of iodosulfonamide 6" (2.8 g, 2.93 mmol) in dry DMF (40 mL) at –40° C. was added EtSH (1.08 mL, 14.65 mmol), followed by dropwise addition of a solution of LHMDS (1.0 M solution in THF, 8.80 mL). The reaction mixture was stirred for 1 hr while allowing it to warm up to r.t., and then neutralized with a saturated solution of $NH_4Cl$ (10 mL), and extracted with EtOAc (5×20 mL). The organic layer was washed with brine (15 mL), separated, dried ($MgSO_4$), and concentrated. The resulting residue was acetylated in $CH_2Cl_2$ (50 mL) with pyridine (1.0 mL), $_2$AcO (1.0 mL) overnight. The organic layer was washed with a sat'd solution of $CuSO_4$ (3×15 mL), water (1×10 mL), a and sat'd solution of $NaHCO_3$ (2×15 mL). The organic layer was separated, dried ($MgSO_4$) and concentrated. The residue was purified by chromatography (1:1, Hex: EA) to obtain 9 (2.38 g, 91%) as syrup; $[\alpha]^{23}{}_D$– 4.0 (c 1.0, $CHCl_3$); IR (film) 3316, 2955, 2875, 1815, 1745, 1448, 1371, 1330, 1227, 1092, 897, 740 cm$^{-1}$; $^1H$ NMR ($CDCl_3$) δ 0.51 (q, 6H, J=8.0 Hz, —$SiCH_2CH_3$), 0.88 (t, 9H, J=7.92 Hz, —$SiCH_2CH_3$), 1.09 (t, 3H, 7.20 Hz, —$SCH_2CH_3$), 2.09 (s, 3H, —$COCH_3$), 2.44 (m, 2H, —$SCH_2CH_3$), 3.48 (bm, 1H, H-2), 3.83–3.70 (m, 7H), 3.89 (bt, 1H), 3.95 (bs, 1H), 4.43 (d, 1H, J=5.44 Hz, H-1), 4.48 (bd, 2H, —$CH_2Ar$), 4.53 (d, 1H, J 6.32 Hz, H-1'), 4.57 (s, 2H, —$CH_2Ar$), 4.75 (bt, 1H, J=5.72 Hz, H-2'), 4.84 (bd, 1H, 9.88 Hz, —$NHSO_2Ph$), 7.20–7.40 & 7.40–7.60 ( m, 13H, Ar—H), 7.97 (d, 2H, J=7.16 Hz, Ar—H); 3C NMR ($CDCl_3$) δ 4.28, 6.65, 14.56, 20.64, 20.89, 56.96, 67.64, 70.49, 70.52, 70.57, 71.14, 73.26, 73.72, 73.96, 74.99, 75.02, 76.88, 82.48, 97.83, 126.21, 127.30, 127.61, 127.78, 127.87, 128.29, 128.38, 128.62, 128.94, 132.17, 137.32, 137.94, 141.38, 153.27, 170.99.

EXAMPLE 10

Disilylated lactal (6'''): To a solution of lactal 6 (3 gm, 4.77 mmol) in dry $CH_2Cl_2$ (50 mL) at 0° C., was added $Et_3N$ (3.34 mL), followed by the dropwise addition of TESOTf (1.61 mL, 7.15 mL). The reaction mixture was stirred for 3 h, and washed with a sat'd solution of $NaHCO_3$ (2×15 mL). The organic layer was separated, dried ($MgSO_4$), and concentrated. The residue was purified by chromatography (4:1, Hex:EA) to obtain 6''' (3.27 g, 92%) as a syrup; $[\alpha]_{23}D$ –38.0 (c 1.0, CHCl3); IR (thin film) δ 3087, 2953, 2875, 1819, 1647, 1647, 1454, 1365, 1240, 1101, 854, 739 cm$^{-1}$; 1H NMR (CDCl3, 400 MHZ) 0.57 & 0.617 (2q, 12H, J=8.0 Hz, —SiCH2CH3), 0.92 & 0.94 (2t, 18H, J=8.0 Hz, —SiCH2CH3), 3.5–3.75 (m, 4H), 3.8–4.0 (m, 3H), 4.05–4.20 (m, 2H), 4.49 (dd, 1H, J=4.36 Hz, J=7.24 Hz), 4.50–4.62 (m, 4H, —CH2Ar), 4.64 (d, 1H, J=5.2 Hz, H-1'), 4.70 (dd, 1H, J=4.0 Hz, J=5.60 Hz, H-4'), 4.76 (bd, 1H, J=7.5 Hz, H-2), 6.32 (d, 1H, J=6.0 Hz, H-1); 13C NMR (CDCl3, 400 MHz) δ 4.56, 4.79, 6.58, 6.76, 65.24, 67.99, 68.02, 69.48, 71.06, 73.37, 73.76, 74.24, 74.37, 75.10, 78.21, 99.21, 99.34, 102.56, 127.63, 127.77, 127.79, 127.88, 128.32, 128.43, 137.53, 138.09, 143.08, 153.87.

EXAMPLE 11

Disilylated Iodosulfonamide (6''''): To a solution of lactal 6''' (2.5 g, 3.36 mmol) (suspended with 4 Å MS (3 g)) and benzenesulfonamide (2.64 g, 3.36 mmol) at 0° C., was added a freshly prepared solution of $I(sym-coll)_2ClO_4$ (5eq) in $CH_2Cl_2$ The reaction mixture was stirred at r.t. for 1 hr, filtered through a pad of silica gel, washed with a sat'd solution of $Na_2S_2O_3$ (3×25 mL), $CuSO_4$ (5×25 mL), and water (2×10 mL). The organic layer was separated, dried ($MgSO_4$), and concentrated. The resulting residue was purified by chromatography (5% EA in $CH_2Cl_2$) to obtain 6'''' (3.20 g, 92%) as a syrup; $[\alpha]^{23}{}_D$ –19.0 (c 1.0, $CHCl_3$); IR (thin film) 3258, 2953, 2875, 1806, 1788, 1453, 1331, 1105, 849, 745 cm$^{-1}$; $^1H$ NMR ($CDCl_3$, 400 MHz) δ –0.57 & 0.64 (2q, 12H, J=8.0 Hz, —$SiCH_2CH_3$), 0.90 & 0.95 (2t, 18H, J=8.0 Hz, —$SiCH_2CH_3$), 3.39 (bm, 1H, H-2), 3.60–3.70 (m, 4H), 3.78–3.83 (bm, 2H), 4.05–4.17 (m, 3H), 4.34 (dd, 1H, J=2.40 Hz, J=8.68 Hz), 4.45 & 4.52 (2d, 2H, J=12.0 Hz, —$CH_2Ar$), 4.55 (s, 2H, —$CH_2Ar$), 4.68 (d, 1H, J=2.96 Hz), 4.89 (d, 1H, J=8.56 Hz), 5.29 (t, 1H, J=8.36 Hz), 5.47 (d, 1H, J=9.64 Hz, —$NHSO_2Ph$), 7.2–7.5 (m, 13H, Ar—H), 7.89 (d, 2H, J=7.6 Hz, Ar—H); 13H NMR ($CDCl_3$, 400 MHz) δ 4.54, 4.94, 6.59, 6.95, 67.94, 68.12, 68.39, 68.63, 73.12, 73.31, 73.36, 73.90, 75.26, 75.33, 76.86, 79.66, 100.04, 127.40, 127.67, 127.76, 127.93, 128.01, 128.36, 128.51, 128.60, 132.39, 137.34, 138.02, 141.31, 154.01.

EXAMPLE 12

Disilylated thiodoner (8): To a solution of iodosulfonamide 6'''' (2.7 g, 2.63 mmol) in dry DMF (40 mL) at –40° C., was added EtSH (0.584 mL, 7.89 mmol), followed by the dropwise addition of a solution of LHMDS (1.0 M solution in THF, 7.89 mL). The reaction mixture was stirred for 1 hr while allowing it to warm up to r.t., and then neutralized with a saturated solution of $NH_4Cl$ (10 mL). EtOAc was added (50 mL). The organic layer was washed with brine (5 mL), separated, dried ($MgSO_4$), and concentrated. The residue was purified by chromatography (7:3, Hex:EA) to obtain 8 (2.3 g, 91%) as syrup; $[\alpha]^{23}{}_D$ –64.0 (c 1.0, $CHCl_3$); IR (thin film) 3314, 2954, 2875, 1807, 1453, 1330, 1181, 1104, 739 cm$^{-1}$; $^1H$ NMR ($CDCl_3$, 400 MHz) δ 0.50 (q, 6H, J=7.88 Hz, —$SiCH_2CH_3$), 0.624 (q, 6H, J 7.6 Hz, —$SiCH_2CH_3$), 0.87 (t, 9H, J=7.88 Hz, —$SiCH_2CH_3$), 0.94 (t, 9H, J=7.96 Hz, —$SiCH_2CH_3$), 1.11 (t, 3H, J=7.44 Hz, —$SCH_2CH_3$), 2.48 (m, 2H, —$SCH_2CH_3$), 3.35(m, 1H, H-2), 3.85–3.68(m, 6H), 3.86 (bm, 1H), 3.97 (bt, 1H), 4.06 (bt, 1H, J=6.56 Hz), 4.49 (s, 2H, —$CH_2Ar$), 4.57 (s, 2H, —$CH_2Ar$), 4.55 (m, 1H), 4.61 (d, 1H, J=6.28 Hz, H-1), 4.67 (d, 1H, J=4.0 Hz, H'-4), 4.87(d, 1H, J=8.84 Hz, H-1), 5.50 (d, 1H, J=8.84 Hz, —$NHSO_2Ph$), 7.2–7.4 (m, 10H, Ar—H), 7.45–7.S5 (m, 3H, Ar—H), 7.94 (d, 2H, J=7.2 Hz, Ar—H); $^{13}C$ NMR ($CDCl_3$)

δ 4.28, 4.45, 6.56, 6.71, 14.58, 25.64, 57.42, 67.82, 69.05, 69.68, 70.37, 71.80, 73.13, 73.66, 73.75, 76.45, 76.64, 77.05, 82.68, 100.94, 127.52, 127.57, 127.79, 127.83, 128.22, 128.35, 128.84, 132.25, 137.49, 138.01, 140.70.

EXAMPLE 13

Tetrasaccharide diol (9'): To a solution of disaccharide 10 (100 mg, 0.173 mmol) and thiodonor 9 (308 mg, 0.34 mmol) in dry $CH_2Cl_2$ (8 mL), suspended with 4 Å MS (1.0 g) was added di-t-butylpyridine (0.311 mL, 1.36 mmol), cooled to −10° C. Then, MeOTf (0.156 mL, 1.36 mmol) was added. The reaction mixture was stirred for 2 h, then at 0° C. for 24 h. After neutralizing with $Et_3N$ (0.1 ml), the mixture was diluted with EtOAc (25 mL), and filtered through a pad of silica gel. The filtrate was washed with a sat'd solution of $NaHCO_3$ (2×10 mL). The organic layer was separated, dried ($MgSO_4$), and concentrated. The residue was purified by chromatography to obtain tetrasaccharide 9' in 55% as syrup; $[\alpha]^{23}_D$ −28.0 (c 1.0, $CHCl_3$); I.R. (film) 3491, 3029, 3874, 1815, 1753, 1647, 1453, 1370, 1221, 1160, 1064, 738 $cm^{-1}$; $^1H$ NMR ($CDCl_3$) δ 0.38 (q, 6H, J=7.96 Hz, —$SiCH_2CH_3$), 0.76 (t, 9H, J=7.96 Hz, —$SiCH_2CH_3$), 1.97 (s, 3H, —$COCH_3$), 3.2–3.32 (m, 2H), 3.35–3.55 (m, 5H), 3.55–3.7 (m, 7H), 3.7–3.8 (m, 4H), 3.95 (dd, 1H, J=4.64 Hz, J=11.28 Hz), 4.0–4.12 (m, 2H), 4.18 (bs, 1H), 4.3–4.65 (m, 15H), 4.7–4.8 (m, 2H), 4.89 (t, 1H, J=5.24 Hz), 5.31 (d, 1H, J=8.4 Hz), 6.32 (d, 1H, J=6.04 Hz, H-1), 7.1–7.5 (m, 28H, Ar—H), 7.85 (d, 2H, J=7.4 Hz, Ar—H); C NMR ($CDCl_3$) δ 4.47, 6.74, 20.62, 58.45, 67.89, 68.16, 68.91, 69.63, 70.01, 70.23, 70.70, 70.74, 72.95, 73.26, 73.32, 73.40, 73.43, 73.79, 74.38, 74.75, 74.81, 75.34, 76.60, 77.19, 82.21, 97.41, 100.41, 102.53, 102.84, 127.30, 127.44, 127.50, 127.56, 127.59, 127.62, 127.76, 127.82, 127.84, 127.96, 128.18, 128.24, 128.33, 128.38, 128.46, 128.83, 132.49, 137.32, 137.89, 138.70, 140.76, 144.51, 153.43, 168.94.

EXAMPLE 14

Tetrasaccharide pentaol (11): To a solution of tetrasaccharide 9' (370 mg, 0.26 mmol) in MeOH (5 mL) was added $K_2CO_3$ (370 mg). The reaction mixture was stirred for 15 min, diluted with $CH_2Cl_2$ (100 mL), and filtered through a pad of silica gel, followed by washing with EtOAc (100 mL). The filtrates were combined, and concentrated to obtain 11 (295 mg, 85%) as a syrup; $[\alpha]^{23}_D$ −18.0 (c 1.0, $CHCl_3$); IR (film) 3469, 3030, 2873, 1648, 1496, 1452, 1328, 1092, 909, 737 $cm^{-1}$; $^1H$ NMR ($CDCl_3$) δ 0.31 (q, 6H, J=6.38 Hz, —$SiCH_2CH_3$), 0.70 (t, 9H, J=6.38 Hz, —$SiCH_2CH_3$), 2.49 (bs, 1H, —OH) , 2.82 (bs, 1H, —OH), 3.16 (m, 1H, —$CHNHSO_2Ph$), 3.3–3.6 (m, 12H), 3.6–3.78 (m, 6H), 3.79 (bs, 2H), 3.8–3.85 (m, 3H), 3.92 (bd, 1H, J=4.23 Hz), 4.0 (bt, 1H), 4.05–4.10 (m, 2H), 4.10–4.25 (m, 3H), 4.30–4.40 (m, 6H), 4.4–4.55 (m, 7H), 4.75 (dd, 1H, J 2.73 Hz, J=4.94 Hz), 4.9 (d, 1H, J=4.20 Hz), 6.17 (d, 1H, 6.63 Hz, —$HNSO_2Ph$), 6.31 (d, 1H, J=4.9 Hz, H-1), 7.0–7.4 (m, 23H, Ar—H), 7.80 (d, 2H, J=6.00 Hz, Ar—H); $^{13}C$ NMR ($CDCl_3$) δ 4.30, 6.72, 57.88, 68.00, 68.78, 68.84, 69.20, 70.46, 70.86, 71.39, 71.99, 73.04, 73.14, 73.31, 73.40, 73.54, 73.79, 75.72, 76.01, 76.16, 81.44, 100.15, 101.85, 102.32, 102.60, 127.30, 127.45, 127.58, 127.62, 127.65, 127.73, 128.17, 128.21, 128.30, 128.33, 128.90, 132.52, 137.71, 137.87, 137.91, 138.10, 138.62, 140.18, 144.27.

EXAMPLE 15

Hexasaccharide tetrol (15'): To a solution of disaccharide 8 (197 mg, 0.20 mmol) and tetrasaccharide 15 (275 mg, 0.20 mmol) in $CH_2Cl_2:Et_2O$ (1:2, 15 mL) (suspended with 4 A molecular sieves (1.20 g)) and di-t-butylpyridine (0.184 mL, 0.80 mmol) at −10° C. was added MeOTf (0.092 mL, 0.80 mmol. The reaction mixture was stirred for 2 h, allowed to warm up to 0° C. After stirring for 24 h, the mixture was diluted with EtOAc (15 mL), filtered through a pad of silica gel, and washed with a sat'd solution of $NaHCO_3$ (2×10 mL). The organic layer was separated, dried ($MgSO_4$), and concentreted. The resdidue was purified by chromatography (1:1, Hex:EA) to obtain 15' (276 mg, 60%) as a syrup; $[\alpha]^{23}_D$ −23.0 (c, 1.0, $CHCl_3$); I.R. (film) 3490, 3030, 2875, 1807, 1649, 1453, 1330, 1093, 909, 743 $cm^{-1}$; $^1H$ NMR ($CDCl_3$) δ 0.25 (m, 6H, —$SiCH_2CH_3$), 0.37 (q, 6H, J=7.92 Hz, —$SiCH_2CH_3$), 0.71 (t, 9H, J=7.88 Hz, —$SiCH_2CH_3$), 0.76 (t, 9H, J=7.92 Hz, —$SiCH_2CH_3$), 0.86 (t, 9H, J=7.88 Hz, —$SiCH_2CH_3$), 2.46 (s, 1H, —OH), 2.52 (s, 1H, —OH), 3.15 (m, 1H, —$CHNHSO_2Ph$), 3.21 (m, 1H, —$CHNHSO_2Ph$), 3.28 (dd, 1H, J=3.04, J=9.24 Hz), 3.37–3.55 (m, 7H), 3.55–3.79 (m, 14H), 3.82 (bs, 2H), 3.89 (bs, 1H), 3.94–4.11 (m, 4H), 4.18 (bs, 1H), 4.28 (m, 1H), 4.33–4.40 (m, 3H), 4.41 (s, 2H, —$CH_2Ar$), 4.44–4.47 (m, 3H), 4.49 (s, 2H, —$CH_2Ar$), 4.52 (m, 1H), 4.54 (s, 2H, —$CH_2Ar$), 4.55–4.63 (m, 2H), 4.66 (dd, 2H, J=3.88 Hz, J=6.04 Hz), 4.74 (dd, 1H, J=2.76 Hz, J=6.08 Hz), 5.28 (d, 1H, J=7.52 Hz, —$NHSO_2Ph$), 5.51 (d, 1H, J=8.32 Hz, —$NHSO_2Ph$), 6.32 (d, 1H, J=6.04 Hz, H-1), 7.10–7.55 (m, 41H, Ar—H), 7.83 (d, 2H, J=7.36 Hz, Ar—H), 7.89 (d, 2H, J=7.48 Hz, Ar—H); $^{13}C$ NMR ($CDCl_3$) δ 4.36, 4.44 (2C), 6.55, 6.67, 6.87, 58.52, 58.82, 67.61, 67.76, 67.82, 68.11, 68.71, 68.94, 69.07, 69.49, 69.75, 69.78, 69.92, 70.47, 70.73, 72.51, 72.92, 73.26, 73.31, 73.34, 73.37, 73.68, 73.85, 74.26, 74.61, 75.21, 75.27, 75.75, 75.90, 76.40, 77.10, 82.97, 83.60, 99.93, 100.49, 101.64, 102.74, 102.82, 103.08, 127.20, 127.38, 127.42, 127.49, 127.54, 127.62, 127.72, 127.76, 127.88, 128.10, 128.17, 128.26, 128.30, 128.40, 128.84, 128.97, 132.38, 132.71, 137.37, 137.57, 137.87, 137.90, 138.12, 138.18, 138.76, 139.9, 140.62, 144.45, 154.16.

EXAMPLE 16

Fully protected Hexasaccharide (12): To a solution of hexasaccharide 15' (175 mg, 0.078 mmol) in dry $CH_2Cl_2$ (20 mL) was added pyridine (2 mL) , $Ac_2O$ (2 mL) and DMAP (cat). The reaction mixture was stirred for 24 h, washed with $CuSO_4$ solution (3×10 mL), and sat'd $NaHCO_3$ (3×10 mL). The organic layer was separated, dried ($MgSO_4$), and concentrated. The residue was purified by chromatography to obtain 12 (175 mg, 95%) as a syrup; $[\alpha]^{23}_D$; I.R. ($cm^{-1}$) $^1H$ NMR ( $CDCl_3$) δ −0.24 (m, 12H, —$SiCH_2CH_3$), 0.54 (q, 6H, J=8.08 Hz, —$SiCH_2CH_3$), 0.68 (bt, 9H, J=7.70 Hz, —$SiCH_2CH_3$), 0.70 (bt, 9H, J=7.8 Hz, —$SiCH_2H_3$), 0.87 (t, 9H, J=7.9 Hz, —$SiCH_2CH_3$), 1.86 (s, 3H, —$COCH_3$) 1.90 (s, 3H, —$COCH_3$), 2.08 (s, 2H, —$COCH_3$), 2.15 (s, 3H, —$COCH_3$), 3.03 (bd, 1H, J=7.68 Hz, —$CHNHSO_2Ph$), 3.2–3.4 (m, 8H), 3.4–3.85 (m, 30H), 3.85–4.2 (m, 8H). 4.20–4.6 (m, 29H), 4.75 (q, 1H, J=3.12 Hz, 6.0 Hz), 4.8 (bd, 1H, J=8.2 Hz, 4.88 (d, 1H, J=3.48 Hz), 5.10 (m, 2H, J=8.76 Hz), 5.26 (d, 1H, J=2.52 Hz), 5.33 (d, 1H, J=8.68 Hz, —$NHSO_2Ph$), 5.42 (d, 1H, J=2.64 Hz), 5.90 (d, 1H, J=10.84 Hz, —$NHSO_2Ph$), 6.31 (d, 1H, 6.0 Hz, H-1), 7.1–7.5 (m, 41H, Ar—H), 7.82 & 7.89 (2bm, 4H, Ar—H); $^{13}H$ NMR ($CDCl_3$) δ 4.10, 4.14, 4.49, 6.52, 6.60, 6.64, 20.75, 20.81, 20.09, 21.46, 55.97, 56.73, 67.83, 68.41, 68.63, 68.80, 69.35, 69.82, 69.88, 70.12, 70.49, 71.09, 71.20, 71.71, 72.84, 72.95, 73.11, 73.38, 73.53, 73.60, 73.67, 73.74, 73.79, 74.10, 74.33, 74.40, 75.32, 75.78, 75.89, 76.18, 76.77, 77.20, 99.75, 100.15, 100.38, 100.53, 101.55, 102.17, 127.26, 127.34, 127.42, 127.47, 127.52, 127.58, 127.61, 127.62, 127.66, 127.73, 127.73, 127.80, 127.85, 128.14, 128.21, 128.26, 128.39, 128.41, 128.66, 128.99, 131.93, 132.60, 137.47, 137.66, 137.77, 137.92, 138.31, 138.43, 138.77, 139.96, 141.74, 144.48, 154.07, 169.44, 169.60, 169.64, 171.34.

EXAMPLE 17

Hexasaccharide triol (13): To a solution of hexasaccharide 12 (175 mg, 0.0725 mmol) in dry THF (5 mL) was added a solution of TBAF (1.0 M in THF): AcOH (0.725 mL, 10 eq). The reaction mixture was stirred at 35° C. for 24 h, diluted with EtOAc (10 mL), and washed with a saturated solution of $NaHCO_3$ (2×5 mL). The organic layer was separated, dried ($MgSO_4$), and concentrated. The residue was purified by chromatography (1:4, Hex:EA) to obtain 13 (143 mg, 93%) as a white glassy substance; $^1$H NMR ($CDCl_3$) δ 1.88, 1.92, 2.01, 2.02 (4s, 3H each, —$COCH_3$), 2.85 (bt, 1H, J=8.24 Hz, —$CHNHSO_2Ph$), 3.02 (bq, 1H, J=7.0 Hz, —$CHNHSO_2Ph$), 3.20 (dd, 1H, J=7.56 Hz, J=8.0 Hz), 3.27 (dd, 2H, J=4.72 Hz, J=10.00 Hz), 3.3–3.8 (m, 36H), 3.87 (bs, 2H), 4.03 (bd, 3H), 4.10 (bs, 1H), 4.2–4.65 (m, 33H), 4.66 (d, 1H, 5.1 Hz), 4.77 (q, 1H, J=3.2 Hz), 5.01 (dd, 1H, J=8.32 Hz, J=9.68 Hz), 5.12 (dd, 1H, J=8.2 Hz, J 9.84 Hz), 5.25 (d, 1H, J=3.16 Hz), 5.39 (d, 1H, J=3.08), 6.32 (d, 1H, J=6.12 Hz, H-1), 7.10–7.45 (m, 41H, Ar—H), 7.78 (m, 4H, Ar—H);

EXAMPLE 18

Nonasaccharide (15): To a solution of hexasaccharide 13 (140 mg, 0.067 mmol) and β-flourofucose 14 (241 mg, 0.53 mmol) in dry toluene (10 mL) (suspended with 4 Å molecular sieves) at 0° C., was added di-t-butylpyridine (0.152 mL, 0,67 mmol) followed by a solution of $Sn(OTf)_2$ (0.223 mg, 0.53 mmol) in THF (1 mL) . The reaction mixture was stirred for 36 h, and then diluted with EtOAc (25 mL), and filtered through a pad of silica gel. The organic layer was washed with a sat'd solution of $NaHCO_3$ (2×10 mL) . The organic layer was separated, dried ($MgSO_4$), and concentrated. The residue was purified by chromatography (1:1, Hex:EA) to obtain 15 (135 mg, 60%) as a syrup; $^1$H NMR ($CDCl_3$) δ 0.87 (d, 3H,J=6.24, —$CH_3$), ), 0.93 (d, 3H, J=6.32 Hz, —$CH_3$), 1.07 9d, 3H, J=6.36 Hz, —$CH_3$), 1.61 9s, 3H, —$COCH_3$), 1.80 (s, 3H, —$COCH_3$), 1.93 (s, 3H, —$COCH_3$), 1.98 (s, 3H, —$COCH_3$), 3.2–3.4 (m, 6H), 3.4–3.9 (m, 27H), 3.9–4.0 (m, 2H), 4.0–4.2 (m, 8H), 4.2–4.65 (m, 34H), 4.65–4.8 (m, 7H), 4.84 (d, 1H, J=5.3 Hz), 4.89 (bt, 1H, J=8.4 Hz), 5.05–5.15 (m, 2H), 5.28 (bs, 1H), 5.35 (d, 1H, J=2.76 Hz), 5.40 (bs, 1H), 5.53 (bs, 3H), 5.65 (d, 1H, J=5.60 Hz), 6.33 (d, 1H, J=6.04 Hz, H-1), 7.)-7.3 (m, 68H, Ar—H), 7.3–7.45 (m, 9H, Ar—H), 7.45–7.57 (m, 3H), 7.65 (d, 2H, J=7.56 Hz, Ar—H), 7.75 (d, 2H, J=7.48 Hz, Ar—H), 7.99, 7.96, 7.94 (3d, 6H, J=7.52 Hz, Ar—H.

EXAMPLE 19

Thioglycoside of Nonasaccharide (16): To a solution of a nonasaccharide 15 (50 mg, 0.0149 mmol) in dry $CH_2Cl_2$ (1 mL) (suspended with 4 Å molecular sieves (100 mg)), was added a solution of dimethyldioxirane in acetone (ca 0.08 M, 3 mL). The reaction mixture was stirred for 45 min, and then solvents were evaporated under a stream of $N_2$ gas. The residue was dried in vacuum (10 min), and then dissolved in $CH_2Cl_2$ (1 mL), and after cooling to –78° C., was reacted with EtSH (1 mL) and TFAA (5 μL) . After 30 min, the mixture was evaporated under a stream of $N_2$ gas, and the residue was dried in vaccume. The crude product was dissolved in $CH_2Cl_2$ (1 mL) and then reacted with acetic anhydride (0.5 mL) and pyridine (0.5 mL). After drying for 24 hrs under reduced presure, the residue was chromatographed (3:2, Hex:EA) to obtain thioglycoside 16 (60%) as a syrup; $^1$H NMR ($CDCl_3$) δ 0.94 (d, 3H, —$CH_3$), 1.02 (d, 3H, —$CH_3$), 1.16 (d, 3H, —$CH_3$), 1.28 (t, 3H, —$CH_3$), 1.93 (s, 3H, —$COCH_3$), 2.0 (s, 3H, —$COCH_3$), 2.04 (s, 3H, —$COCH_3$), 2.07 (s, 3H, —$COCH_3$), 2.14 (s, 3H, —$COCH_3$), 2.71 (m, 2H, —$SCH_2CH_3$), 3.1–4.0 (m, several protons), 4.1–5.0 (m, several protons), 4.82 (d, 1H), 4.89 (t, 1H), 5.20 (d&m, 2H), 5.35 (d, 1H), 5.45 (d, 1H), 5.50 (bs, 1H), 5.63 (bs, 2H), 5.74 (m, 1H), 7.0–8.2 (m, 90H, Ar—H);

EXAMPLE 20

Sphingosine glycoside (18): To a solution of thioglycoside 16 (30 mg, 0.0086 mmol) and azidohydrin 17 at 0° C. in dry $CH_2Cl_2$: Ether (1:2, 1.5 mL) (suspended with 4 Å molecular sieves (100 mg)) was added MeOTf (0.0038 mL, 4 eq). The reaction mixture was allowed to warm up to room temperature. After 24 hrs, the mixture was diluted with EtOAc (5 mL), filtered through a pad of silica gel, and washed with a sat'd solution of $NaHCO_3$ (2×5 mL). The organic layer was separated, dried ($MgSO_4$), and concentrated. The residue was purified by column chromatogrphy (1:1 Hex:EA) to obtain Sphingosine glycoside 18 (55%) as a syrup; $^1$H NMR ($CDCl_3$) δ 0.80 (m, 9H, 0.85(d, 3H, —$CH_3$), 0.93 (d, 3H, —$CH_3$), 1.07 (d, 3H, —CH3), 1.18 (bm, 23H, aliphatic —$CH_2$), 1.33 (bs, 2H) 1.5 (bd, 4H), 1.81 (s, 3H, —$COCH_3$), 1.94 (s, 3H, —$COCH_3$), 1.97 (s, 3H, —$COCH_3$), 2.0 (s, 6H, —$COCH_3$), 3.1–3.7 (m, several protons), 3.7–4.1 (m, several protons), 4.2–4.8 (m, several protons), 4.82 (d, 1H), 4.89 (t, 1H), 4.97 (d, 1H), 5.1 (m, 2H), 5.37 (m, 4H), 5.47 (d, 1H), 5.53 (bs, 2H), 5.60 (d,1 H), 5.7 (m, 1H), 7.0–8.1 (m, 95H, Ar—H).

EXAMPLE 21

Amide (protected KH-1 antigen) (18'): To a solution of azide 18 (15 mg, 0.0039 mmol) in EtOAc (3 mL) was added Lindlar's catalyst (50 mg) and Palmitic anhydride (10 mg, 0.020 mmol). The reaction mixture was stirred at room temperature under a $H_2$ atmosphere for 24 h, and then filtered through a pad of silica gel, rinsed with EtOAc (20 mL), and concentrated. The residue was purified by chromatography (1:1 EA:Hex) to give amide 18' (85%) as a syrup: $^1$H NMR ($CDCl_3$) δ 0.79 (m, 9H, 0.84 (d, 3H, —$CH_3$), 0.92 (d, 3H, —$CH_3$), 1.06 (d, 3H, —$CH_3$), 1.17 (bm, 45H, aliphatic —$CH_2$), 1.48 (bs, 9H), 1.77 (s, 3H, —$COCH_3$), 1.90 (s, 3H, —$COCH_3$), 1.95 (s, 3H, —$COCH_3$), 1.97 (s, 6H, —$COCH_3$), 3.0–3.9 (m, several protons), 4.0–5.0 (m, several protons) 5.51 (bs, 1H), 5.2–5.4 (m, 3H), 5.5 (bs, 1H), 5.6–5.8 (m, 2H); 7.0–8.1 (m, 95H, Ar—H).

EXAMPLE 22

KH-1 antigen (1): To a solution of liquid ammonia (5 mL) under $N_2$ at –78° C. was added sodium (18 mg). To the resulting blue solution was added a solution of protected KH-1 derivative 18' (20 mg, 0.005 mmol) in dry THF (1 mL). After 45 min at –78° C., the reaction mixture was quenched with absolute MeOH (5 mL). Most of the ammonia was removed in a stream of nitrogen gas. The resulting solution was diluted with MeOH (5 mL) and stirred overnight, and then neutralized with $Et_3N$-HCl. After stirring for 15 min, the mixture was dried under nitrogen. The crude product was then suspended in DMF (1.0 mL), THF (1.0 mL), and $Et_3N$ (1.0 mL) and treated with $Ac_2O$ (1 mL) and DMAP (cat). After stirring overnight, the reaction mixture was concentrated, passed through a plug of silica gel using EtOAc as an elutant and concentrated. The syrup obtained was dissolved in MeOH (5 mL) and treated with MeONa (5 mg) for 24 h, and then neutralized with Dowex 50-X8. Filtration and concentration gave the KH-1 antigen (70%). An analytical sample was prepared by RP column chromatography, eluting with water-5% methanolic water, followed by lyophilization to obtain 1 as a white powder; $^1$H NMR (DMSO) δ 0.95 (m, 3H), 1.1–1.35 (3d, 9H, —CH$_3$), 1.38 (bm, multipleple protons, alphatic —CH$_2$), 1.5 (m, 9H), 1.85 (s, 6H, NHCOCH$_3$), 1.9 (m, 2H), 2.0–2.20 (m, 6 H), 3.0–4.0 (m, Multiple protons), 4.1 (q, 1H), 4.17 (d, 1H, H-1), 4.27 (m, 1H), 4.34 (bm, 1H), 4.41 (d, 1H), 4.6 (q, 1H), 4.67 (m), 4.75 (t, 2H), 4.88 (d, 2-3H), 4.97 (d, 1H), 5.36 (m, 1H), 5.56 (m, 1H).

EXAMPLE 23

Allyl glycoside (2): To a solution of liquid ammonia (5 mL) under N$_2$ at −78° C. was added sodium (94 mg). To the resulting blue solution was added a solution of nonasacchride glycal 15 (75 mg, 0.022 mmol) in a dry THF (3 mL). After 45 min at −78° C., the reaction was quenched with absolute MeOH (5 mL). Most of the ammonia was removed with a stream of nitrogen. The solution was diluted with MeOH (5 mL), stirred overnight, and neutralized with Dowex 50-X8 (846 mg). The resulting mixture was stirred for 15 min, and filtered. The resins were washed with NH$_3$—MeOH sloution (3×20 ml). The filtrates were combined, and dried under a stream of nitrogen gas. The crude product was then suspended in DMF (1.0 mL), THF (1.0 mL), and Et$_3$N (1.0 mL) and then treated with Ac$_2$O (1 mL) and DMAP (cat). The reaction mixture was stirred for 24 h, concentrated, passed through a plug of silica gel in EtOAc, and again concentrated. The syrup obtained was dissolved in CH$_2$Cl$_2$, then treated with dimethyldioxirane solution in acetone (ca. 0.08 M, 5 mL) at 0° C. under N$_2$. The mixture was stirred for 45 min, and concentrated under a stream of N$_2$ gas. The syrup obtained was reacted with allyl alcohol (5 mL). After 24 h, excess allyl alcohol was evaporated and the crude syrup was dissolved in MeOH and treated with MeONa (25% in MeOH, 60 μL). After 24 h, the mixture was neutralized with Dowex 50-X8, filtered and concentrated to give allylated nonasaccharide 2 (60%). An analytical sample was prepared by RP column chromatography, eluting with water-5% methanolic water, followed by lyophilization to obtain white powder; $^1$H NMR (D$_2$O) δ 1.0–1.35 (3d, 9H, —CH$_3$), 2.0 (s, 6H, —COCH$_3$), 3.3 (bm, 1H, —CHNHAc), 3.4–4.0 (m, multiple protons), 4.08 (bs, 1H), 4.12 (bs, 1H), 4.22 (m, 1H), 4.42 (t, 2H), 4.5 (t, 2H), 4.7 (d, 2H), 4.86 (d, 1H), 5.1(bs, 2H), 5.26 (bs, 1H), 5.39 (d, 1H) 5.95 (m, 1H, —CHCH=CH$_2$).

PREPARATION OF HEPTA AND KH-1 -KLH CONJUGATES BY DIRECT AND CROSS-LINKER METHOD

The allyl glycoside of KH-1 was conjugated to KLH (Keyhole Lympet Hemocyanin) protein via two different methods. The first was the direct coupling method which utilized the reductive amination reaction between the lysines of KLH protein and the aldehyde moiety obtained by ozonolysis of KH-1 allyl glycoside. This method typically provides the glycoprotein with around 141 carbohydrate units (KH-1) per KLH.

Figure 12A:
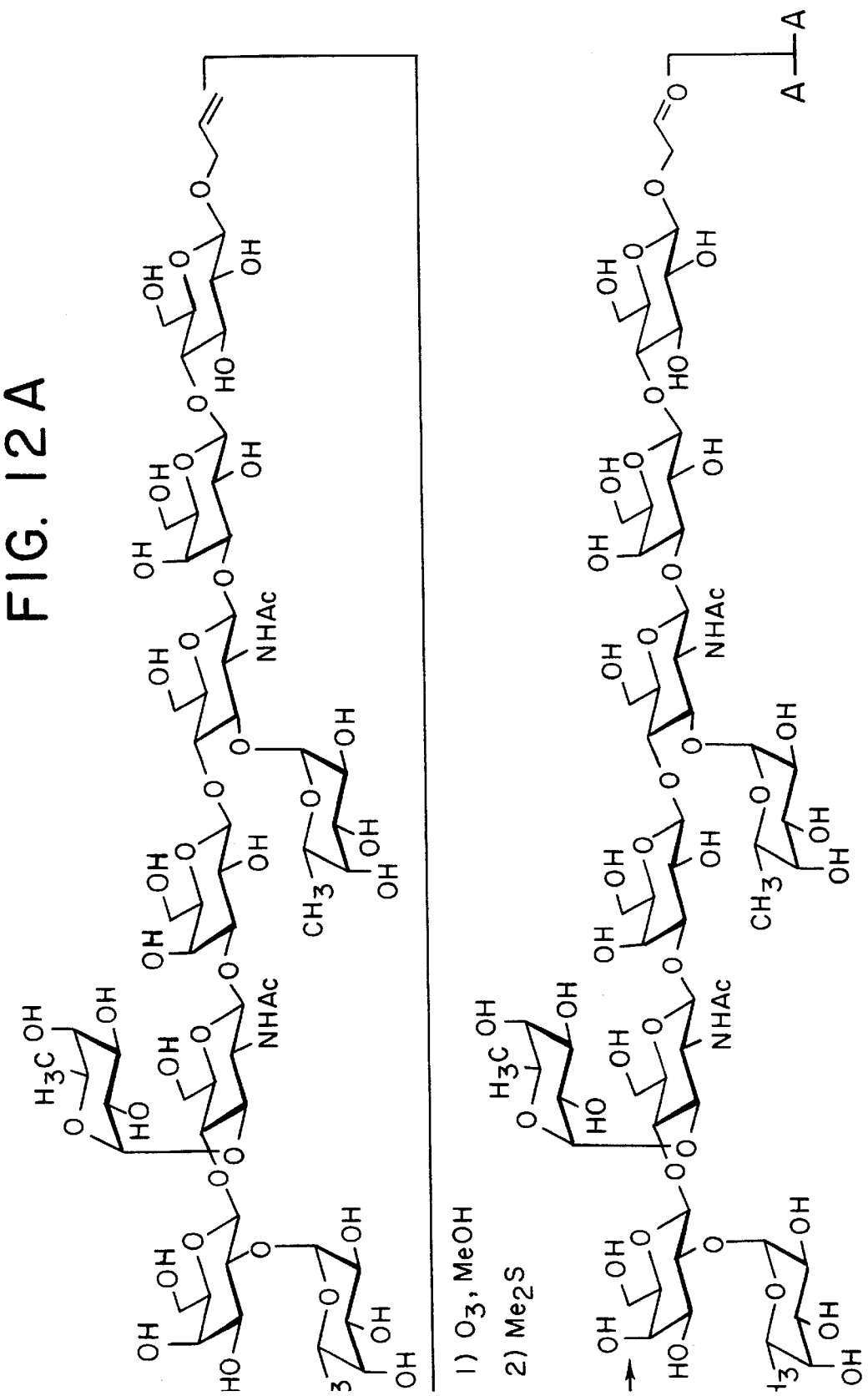
FIGS. 12(A) and 12(B) illustrate the direct coupling of KH-1 to KLH.
Figure 12B:
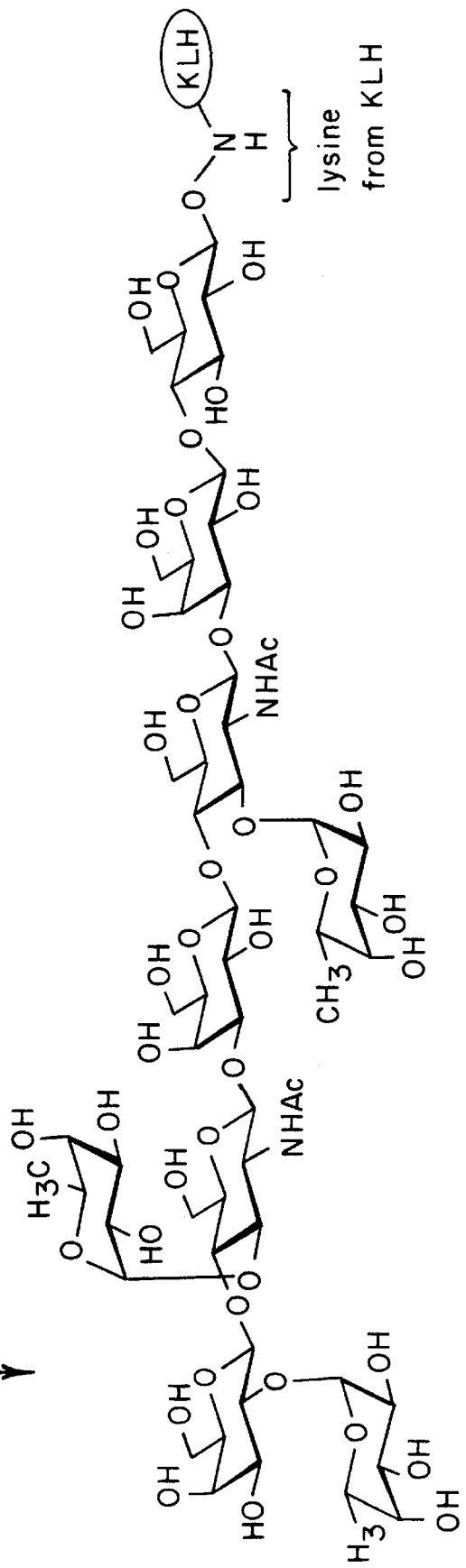
Figure 13A:
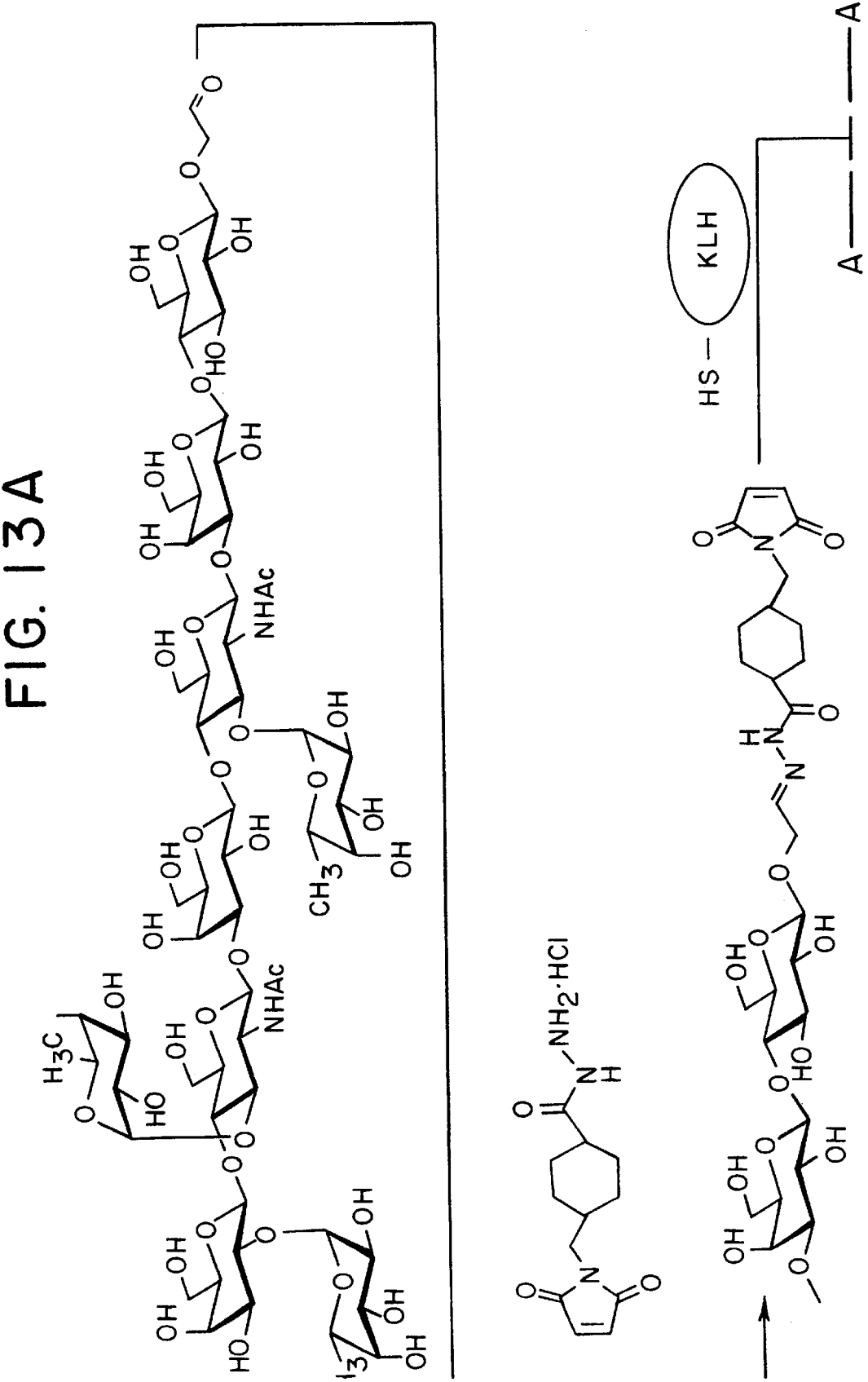
FIGS. 13(A) and 13(B) illustrate the coupling of KH-1 to KLH via a $M_2$ cross-linker.
Figure 13B:
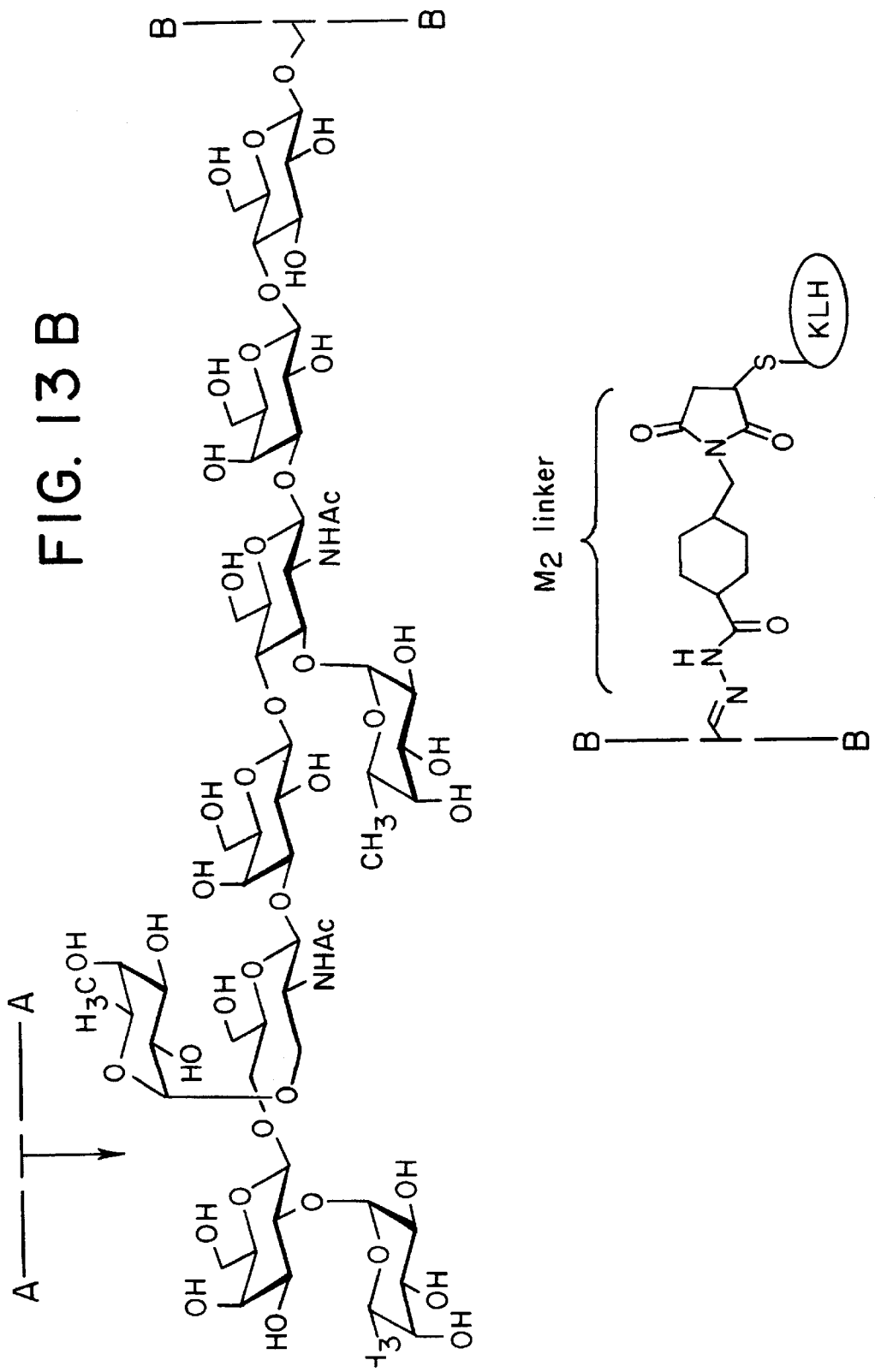

The other conjugation method utilized a cross linker known as M$_2$. The same aldehyde of KH-1 antigen utilized in direct coupling was further derivatized to a suitable conjugatable form containing M$_2$ linker. Then the resulting compound was coupled to thiolated KLH protein. This crosslinker method was highly efficient, providing the glycoprotein conjugate with around 492 carbohydrate units (KH-1) per KLH. FIGS. 12 and 13 describe two coupling methods.

Figure 11A:
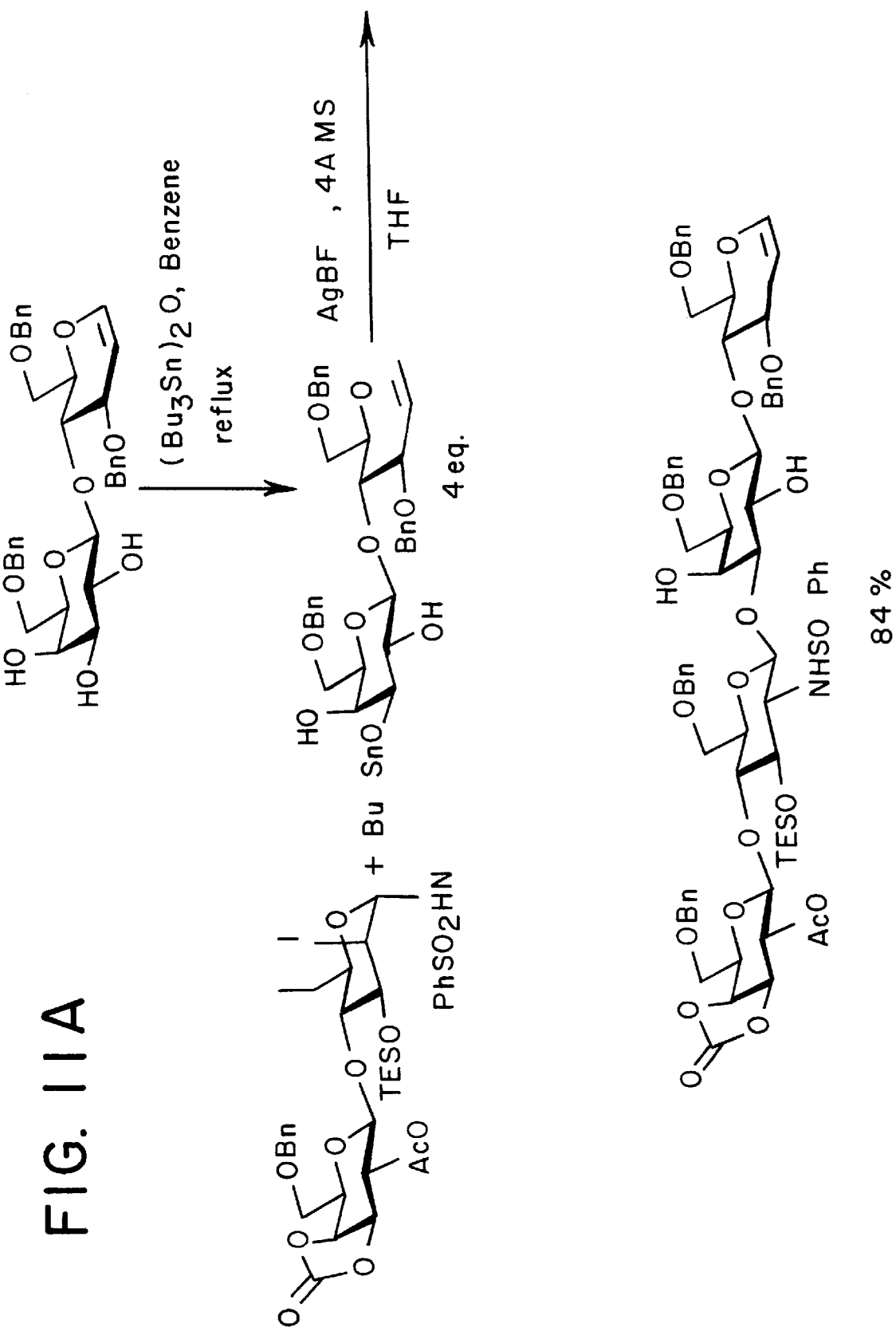
FIGS. 11(A) and 11(B) provide a synthetic stratety for the KH-1 tetrasaccharide and hexasaccharide intermediates.
Figure 11B:
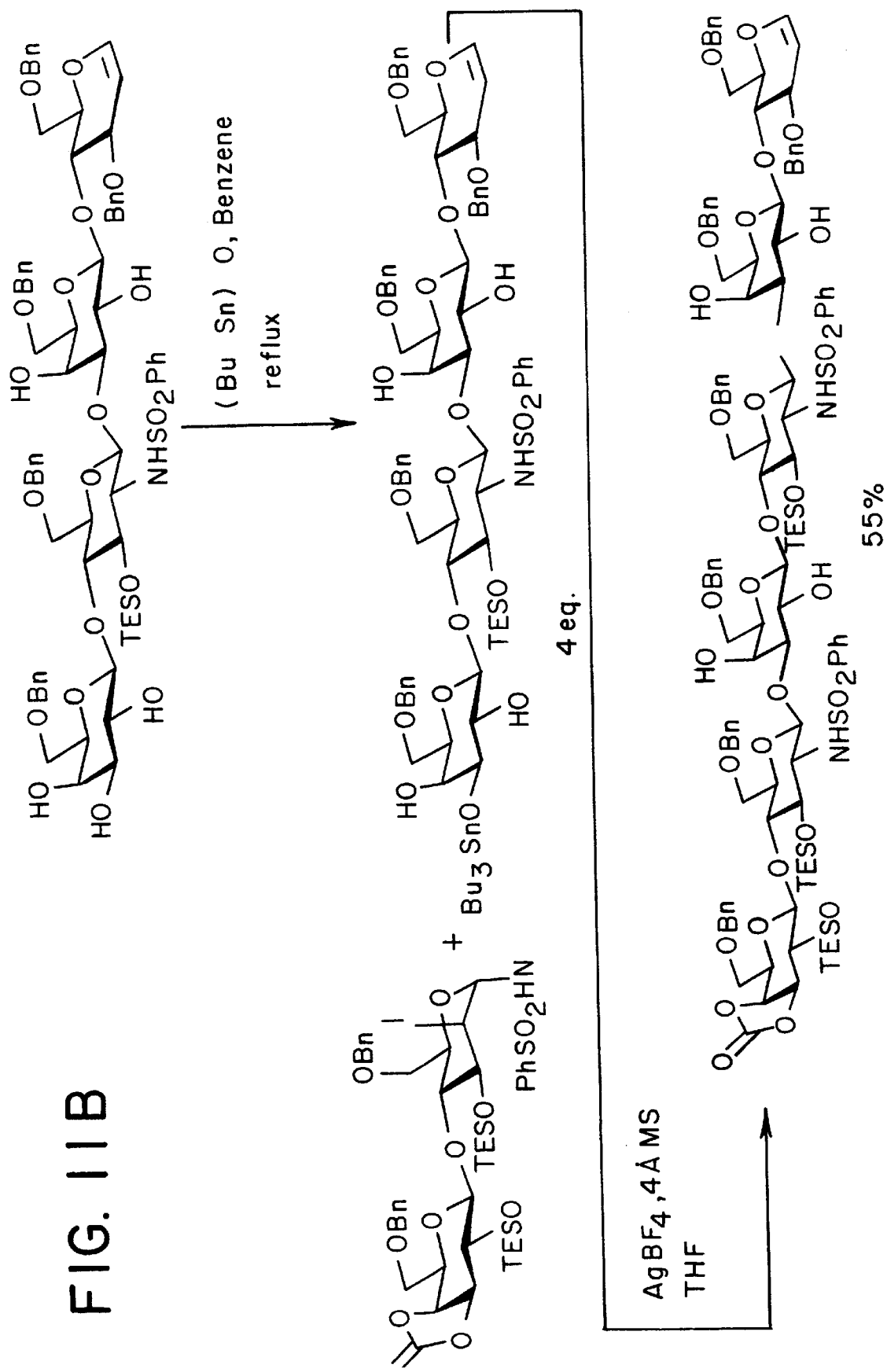

Groups of mice were immunized with both types of glycoprotein conjugates (KH1-KLH and KH1-M$_2$-KLH). An immunological adjuvant QS-21 was co-administered in the immunization. The antibodies thus elicited were assayed by ELISA and FACS method. The cross-linked conjugate (KH1-M$_2$-KLH) showed increased immune response from the mice, though both types of conjugate effectively elicited antibodies. FIG. 11 describes an alternative synthesis of KH-1 tetrasaccharide and hexasaccharide.

Accordingly, the allyl group in KH-1 or the heptasaccharide disclosed herein was converted to an aldehyde group by ozonolysis and linked to —NH$_2$ groups of KLH by reductive amination method in the presence of sodium cyanoborohydride as described for globo H. (Ragupathi G, et al., *Angew. Chem. Int. Ed. Engl.* 1997, 36, 125–128.) In the case of the cross-linker method, the aldehyde group obtained through ozonolysis was first reacted with hydrazide of M$_2$CH$_2$ (4-maleimidomethyl) cyclohexane-1-carboxyl hydrazide) and reacted with thiolated KLH as described in Ragupathi G., et al., "A novel and efficient method for synthetic carbohydrate conjugate vaccine preparation: Synthesis of sialyl Tn-KLH conjugate using an M$_2$C$_2$H linker arm" *Glycoconjugate J.*, in press. For example, 4 mg of KH-1 allyl glycoside in methanol was stirred at −78° C. in a dry-ice/ethanol bath and ozone gas was passed through the solution for 0 min under vigorous stirring. The excess of ozone was then displaced with nitrogen over a period of 5 min. Methyl sulfide (100 μl) was added and the reaction mixture stirred at room temperature for 2 hours and distributed equally in two vials. The solvent was removed under a stream of nitrogen. The resulting white solid was used directly in the subsequent conjugation steps. Direct Conjugation of KH-1-aldehyde with KLH:

Two mg KH-1 aldehyde was dissolved in 1 ml of 0.1M phosphate buffered saline (PBS) pH 7.2 and 4 mg of KLH in PBS. Two mg sodium cyanoborohydride was added and the mixture incubated under gentle agitation at 37° C. for 48 h. After 16 h, an additional 1.0 mg sodium cyanoborohydride was added and the incubation continued. The unreacted KH-1 aldehyde was removed completely with multiple washes using a Amicon Centriprep with molecular weight cut-off value 30000 dalton, with 6–7 changes of PBS at 4° C.

Conjugation of KH-1-aldehyde through M$_2$C$_2$H to thiolated KLH:

Preparation of KH-1-M$_2$C$_2$H

Two mg of KH-1-aldehyde was dissolved in 1 ml of 0.1M sodium acetate buffer pH 5.5, and 4 mg of M$_2$C$_2$H in 100 μl of dimethyl sulfoxide (DMSO) was added. The reaction mixture was incubated at room temperature for 15 min with gentle stirring. At the end of 15 min 2 mg of solid sodium cyanoborohydride was added and the incubation continued at room temperature for 2 h. Unreacted M$_2$C$_2$H was removed in a Sephadex G10 column equilibrated previously with 0.1 M sodium phosphate buffer pH 6.0 containing 5 mM EDTA and eluted with the same buffer. The fractions positive for KH-1 by TLC with orcinol were combined.

Addition of sulfhydryl groups to KLH

2-Iminothiolane (2 mg) dissolved in thiolation buffer (50 mM triethanolamine, 0.15 M NaCl, 5 mM EDTA, pH 8.0)

was added to 4 mg of KLH and incubated with stirring at room temperature for 2 h. Unreacted 2-iminothiolane was removed by Sephadex G15 column equilibrated previously with 0.1 M sodium phosphate buffer pH 7.2 containing 5 mM EDTA and eluted with the same buffer. Fractions positive for KLH with BioRad protein assay dye reagent, were combined. A small portion was used to estimate sulfhydryl groups in the thiolated KLH using Ellman's reagents and cysteine as standard. Riddles P. W., et al., *Anal. Biochem.* 1979, 94, 75–81. The KLH was estimated by a dye method using BioRad dye reagent according to the manufacture's instructions.

Conjugation of KH-1-$M_2C_2H$ product and thiolated KLH were mixed and adjusted to pH 7.2 with 0.1M sodium phosphate buffer pH 8.0. The reaction mixture was then incubated at room temperature overnight. The content of the KH-1-$M_2C_2H$-KLH reaction vial was transferred to a Centriprep concentrator 30 (Amicon: molecular cut-off 30000 Dalton) and unreacted KH-1-$M_2C_2H$ was removed completely with multiple washes. The conjugate was checked by HPTLC for the absence of unreacted KH-1 as mentioned above. The epitope ratios of two batches of conjugate were determined by estimating protein content by BioRad dye binding protein assay and carbohydrate by a HPAEC-PAD assay. The epitope ratio of hepta-KLH and hepta-$M_2$-KLH was 112/1 and 197/1 respectively. The epitope ratio of KH-1-KLH and KH-1-$M_2$-KLH was 141/1 and 492/1, respectively.

TABLE 1

Antibody Titers by ELISA against KH1-KLH

| Group | Pre-serum | | 10 days post 3rd | |
|---|---|---|---|---|
| | IgM | IgG | IgM | IgG |
| KH-1-KLH | | | | |
| 1.1 | 0 | 0 | 100 | 0 |
| 1.2 | 0 | 0 | 100 | 0 |
| 1.3 | 0 | 0 | 100 | 0 |
| 1.4 | 100 | 0 | 300 | 0 |
| 1.5 | 100 | 0 | 100 | 0 |
| KH-1-$M_2$-KLH | | | | |
| 2.1 | 0 | 0 | 0 | 0 |
| 2.2 | 0 | 0 | 900 | 300 |
| 2.3 | 0 | 0 | 300 | 300 |
| 2.4 | 0 | 0 | 900 | 900 |
| 2.5 | 0 | 0 | 100 | 0 |
| 3.1 | 0 | 0 | 2700 | 24,300 |
| 3.2 | 0 | 0 | 2700 | 8100 |
| 3.3 | 0 | 0 | 300 | 0 |
| 3.4 | 0 | 100 | 2700 | 2700 |
| 3.5 | 100 | 0 | 8100 | 900 |

(0.2 ug/well antigen plated)

TABLE 2

Cell Surface reactivity of KH-1 antibodies on MCF-7 cells by FACS.

| Group | % of cells positive | |
|---|---|---|
| | IgM | IgG |
| KH1-KLH | | |
| 1.1 | 28.4% | 14.1% |
| 1.2 | 16.9% | 18.8% |
| 1.3 | 12.9% | 11.0% |

TABLE 2-continued

Cell Surface reactivity of KH-1 antibodies on MCF-7 cells by FACS.

| Group | % of cells positive | |
|---|---|---|
| | IgM | IgG |
| 1.4 | 36% | 12.3% |
| 1.5 | 35.56% | 30.2% |
| KH1-M2-KLH | | |
| 2.1 | 30.18% | 88.1% |
| 2.2 | 36.59% | 76.2% |
| 2.3 | 18.16% | 93.1% |
| 2.4 | 47.9% | 91.9% |
| 2.5 | 20.03% | 97.9% |

Mouse presera IgM: 1.72%, Mouse preIgG 0.76%, Mab BR96.78.17%

Serological Analysis:

ELISA: Enzyme-linked immunosorbent assays (ELISAS) were performed as described by Livingston, P. O. et al., *Cancer Immunol. Immunother.*, 1989, 29, 179–184, 1989. Serially diluted antiserum was added to wells coated with antigen (0.1 μg) and incubated for 1 h at room temperature. Goat anti-mouse IgM or IgG conjugated with alkaline phosphatase served as secondary antibodies. Absorbance was measured at 414 nm. The antibody titer was defined as the highest serum dilution showing an absorbance 0.1 or greater above that of normal mouse sera.

Flow Cytometry:

Cells from the KH-1-positive breast cancer cell line MCF-7 served as target. Soule, H. D., et al., *J. Natl. Cancer Inst.*, 1973, 51, 1409–1416. Single cell suspensions of $2 \times 10^5$ cells/tube were washed in PBS with 3% fetal calf serum and 0.01 M $NaN_3$ and incubated with 20 μl of 1:20 diluted antisera or mAb BR-96 for 30 min on ice. After washing the cells twice with 3% FCS in PBS, 20 μl of 1:15 goat anti-mouse IgM or IgG-labeled with fluorescein-isothiocyanate (FITC) was added, mixed and incubated for 30 min. After wash, the positive population and mean fluorescence intensity of stained cells were analyzed by flow cytometry (EPICS Profile II, Coulter, Co., Hialeah, Fla.). Zhang, S. et al., *Cancer Immunol. Immunother.*, 1995, 40, 88–94.

Immune Adherence (IA) Assay:

The IA assay measures rosetting of human RBC (blood group O) with guinea pig complement on target cells mediated by IgM antibodies, and was performed as described previously. Shiku, H., et al., *J. Exp't Med.*, 1976, 144, 873–881. Individual target cells were scored as positive when 50% or more of the cell perimeter 3 was surrounded by indicator cells.

Complement Dependent Cytotoxicity (CDC):

Complement dependent cytotoxicity was assayed at a serum dilution of 1:10 with MCF-7 cells by a 4 h europium-release assay. Zhang, S., et al., *Cancer Immunol. Immunother.*, 1995, 40, 88–94. All assays were performed in triplicate. Controls included cells incubated only with culture medium, complement, antisera or mAb BR-96. Spontaneous release was the europium released by target cells incubated with complement alone. Percent cytolysis was calculated according to the formula:

$$\text{Specific Release (\%)} = \frac{\text{Experimental release} - \text{spontaneous release}}{\text{Maximum release} - \text{spontaneous release}} \times 100$$

Inhibition Assay:

Antisera at 1:1500 dilution or mAb BR-96 at 0.1 μg/ml were mixed with various concentrations of structurally related and unrelated carbohydrate antigens. The mixture was incubated at room temperature for 30 min, and transferred to an ELISA plate coated with KH-1-ceramide. ELISAs were performed as described above. Percentage inhibition was calculated as the difference in absorbance between the uninhibited and inhibited serum.

Immunization of Mice

Groups of mice (CB6F1 female; 6 weeks of age) obtained from Jackson Laboratory, Bar Harbor, Me., were immunized subcutaneously with KH-1-KLH or KH-1-$M_2C_2H$-KLH containing equivalent to 3 μg KH-1 only (the quantity of KLH varied depending on the epitope density) mixed with 10 μg of immunological adjuvant QS-21, a saponin derivative from the bark of the *Quillaja saponaria* Molina tree (Aquila,. Worcester, Mass.) at 0, 1 and 2 weeks and bled 10 days after the third immunization. The presence of antibody was assayed by an enzyme linked immunosorbent assay (ELISA) as described in Kensil C. R. et al., *J. Immunol.*, 1993, 146, 431–437, using KH-1 ceramide as target antigen. The cell surface reactivity of anti-KH-1 antibodies was tested on KH-1 positive MCF-7 cells by flow cytometry assays. The mice vaccinated with KH-1-$M_2C_2H$ are made the high titer antibody against the synthetic KH-1 and the antibodies were reacted strongly on the cell's surface that expressed KH-1 antigens.

Binding of Monoclonal Antibody BR 96 with synthetic KH-1 and other Carbohydrate by Dot-blot Immune Stain:

0.5 μg KH-1 ceramide and other $Le^y$ antigen and unrelated antigens were spotted on nitrocellulose strips. Dot blot Immune staining was performed monoclonal antibody BR 96 after blocked with 6% bovine serum albumin in PBS for 1 h and incubated with antibody BR 96 (diluted 1:500 in PBS) overnight at room temperature. The strips were washed with PBS containing 0.05% Tween 20 and incubated with anti-mouse IgG antibody conjugated with horseradish peroxidase at 1:200 dilution for 3 h at room temperature. Then the strips were washed with PBS-0.05% Tween 20 and developed with 4-chloro-1-naphtol-$H_2O_2$. The results are summarized in Table 1. The synthetic KH-1 reacted very strongly when compared with other Ley related antigens unrelated antigens were failed to react with BR 96 antibody.

TABLE 3

Binding of Monoclonal Antibody Br 96 with KH-1 and other Carbohydrates by Dot-blot.

| Carbohydrate | Monoclonal Antibody | |
| --- | --- | --- |
| | BR 96 ($Le^y$ related) | F12 (FucosylGM1) |
| KH-1 ceramide | very strong (+++) | negative |
| $Le^y$-ceramide | strong (++) | negative |
| $Le^y$-KLH | strong (++) | negative |
| Globo H ceramide | negative | negative |
| TF-ceramide | negative | negative |
| SSEA-ceramide | negative | negative |
| $Le^y/Le^b$(Ovarian cyst Mucins-Tighe)* | strong (++) | negative |
| $Le^a/Le^x$(Ovarian cyst mucins-N1)* | weak (+) | negative |
| Non fucosylated precursor of Lewis* | negative | negative |
| $Le^a$-PAA | negative | negative |
| $Le^x$-PAA | weak(+) | negative |
| FUcGMI | negative | very strong (+++) |
| GD3 | negative | negative |

*extracted from patient tissue

Discussion

Human tumors are often marked by the presence of unusual carbohydrate structural motifs. Hakomori, S., *Cancer Res.*, 1985, 45, 2405; Feizi, T., *Cancer Surveys*, 1985, 4, 245; Lloyd, K. O., *Am. J. Clin. Pathol.*, 1987, 87, 129; Lloyd, K. O., *Cancer Biol.*, 1991, 2, 421. These carbohydrate domains are encountered as cell-surface bound glycolipids or glycoproteins. Hakomori, S., *Cancer Cells*, 1991, 3, 461. It would be useful for cancer therapy to achieve some level of immune response by vaccinating cancer patients with such cell-free carbohydrate domains, obtained through total synthesis and suitably bioconjugated. Preliminary synthetic studies have been reported. M. T. Bildoeau, T. K. Park, S. Hu, J. T. Randolph, S. J. Danishefsky, P. O. Livingston, and S. Zhang, *J. Am. Chem. Soc.*, 1995, 117, 7840; T. K. Park, I. J. Park, I. J. Kim, S. Hu, M. T. Bilodeau, J. T. Randolph, O. Kwon and S. J. Danishefsky, *J. Am. Chem. Soc.*, 1996, 118, 11488. In addition, the utility of tumor-associated carbohydrate antigens is supported by the observed establishment of responses to the human cancer lines by sera of mice immunized with such antigens. G. Ragupathi, et al., *Angewandte Chemie*, In Press.

In conducting this project, the important issue of "strategy" in oligosacchcaride synthesis is addressed. Of course, in this field (as opposed to "conventional" natural product synthesis) the basic building blocks which are considered to be rather restricted and tend to bear obvious homology with readily recognized components of the target system.

From this perspective a plan was pursued which would build a hexasaccharide (cf. structure 13) so differentiated in terms of its protecting patterns (see asterisks) as to allow for the unveiling of the three free hydroxyls to serve as α-fucosylation acceptor sites (see structure 13) . In this way, the three immunologically defining α-fucose units might be introduced in one concurrent synthetic operation.

Assembling the hexasaccharide involved a potentially forbidding network of hydroxyl group functionality. Regarding this, advantages were observed in drawing from a few of the basic principles now well appreciated in the logic of glycal assembly. Bilodeau, M. T.; Danishefsky, S. J., *Angew. Chem. Int. Ed. Engl.*, 1996, 35, 1380.

Thus, differentiated glycals 4 and 5 are derived from D-glucal by exploiting the reliable reactivity preference of the $C_6$, $C_3$ and $C_4$ hydroxyls ($C_6 > C_3 > C_4$). Moreover, the fashioning of a clean α-epoxide from galactal derivative 3 is known. Also, known (Halcomb, R. L.; Danishefsky, S. J., *J. Am. Chem. Soc.*, 1989, 111, 6661), is the excellent β-galactosyl donating capacity of such an epoxide. Coupling of this epoxide to 4 and to 5, under mediation by a simple reagent (anhydrous zinc chloride), gave 6 and 7, respectively. The $C_3'$ hydroxyl of the lactal derivative 6 was protected as a triethylsilyl derivative. In the resultant structure 8, two of the three sites destined for eventual fucoyslation have been distinguished. In a parallel experiment, compound 6 could be converted by acetylation to its $C_3'$ acetate, and overall sulfonamido (2α) ethanethiylation (Griffith, D. A.; Danishefsky, S. J., *J. Am. Chem. Soc.,* 1990, 112, 5811), (1β) of its glycal linkage (leads to 9 which carries the third eventual fucosylation center at the site of its TES group) Cleavage of the carbonate linkage of 7 generated triol 10. Here, advantage is taken of another well appreciated preference wherein the glycosyl accepting site in such a triol tends to be at its $C_3'$ hydroxyl acetate (see asterisk). Kameyama, A; Ishida, H.; Kiso, M.; Haegawa, A. J., *Carb. Chem.,* 1991, 5, 337. Coupling of 10 and 9 afforded, after cleavage of its cyclic carbonate and acetate, a pentaol (see structure 11).

At this stage, the proposition was pursued in which the 1,2,3 in the terminal ring D, rather than the 1,3 diol in ring B would serve as the pre-lactosamine acceptor site with donor 8. This, in fact proved to be the case. The successful glycosylation was followed by acetylation of the four remaining hydroxyl groups. This sequence led to 12 and thence to 13 as shown.

Thus, it was possible to introduce the three α-L-fucose residues in one step via donor 14 (Danishefsky, S. J.; Gervay, J.; Peterson, J. M.; McDonald, F. E.; Koseki, K.; Oriyama, T.; Griffith, D. A.; Wong, C.- H.; Dumas, D. P., *J. Am. Chem. Soc.,* 1992, 114, 8331), thereby affording a 60% yield of the nonasaccharide. From 15, the sorts of protocols required to reach 1 and 2 were qualitatively well precedented. In the case of 2, the chemistry followed very closely from the methodology developed for the globo-H breast tumor, conjugatable allyl glycoside. M. T. Bildoeau, T. K. Park, S. Hu, J. T. Randolph, S. J. Danishefsky, P. O. Livingston, and S. Zhang, *J. Am. Chem. Soc.,* 1995, 117, 7840; T. K. Park, I. J. Park, I. J. Kim, S. Hu, M. T. Bilodeau, J. T. Randolph, O. Kwon and S. J. Danishefsky, *J. Am. Chem. Soc.,* 1996, 118, 11488. To reach the naturally occurring glycolipid antigen 1, a small but useful variant was introduced wherein the pre-ceramide acceptor 17 was coupled to an anomeric thioethyl donor derived from the glycal epoxide. For a review, see: Fugedi, P.; Garegg, P. J.; Lönn, H.; Norberg, T.; *Gycocnjugate J.,* 1987, 4, 97; Lönn,

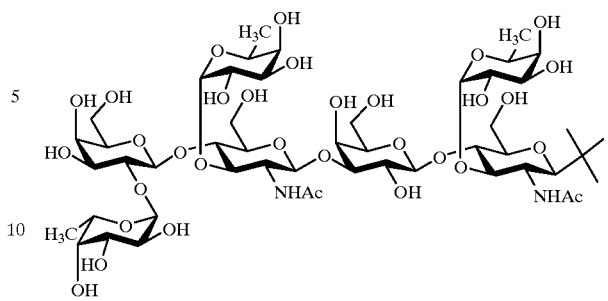

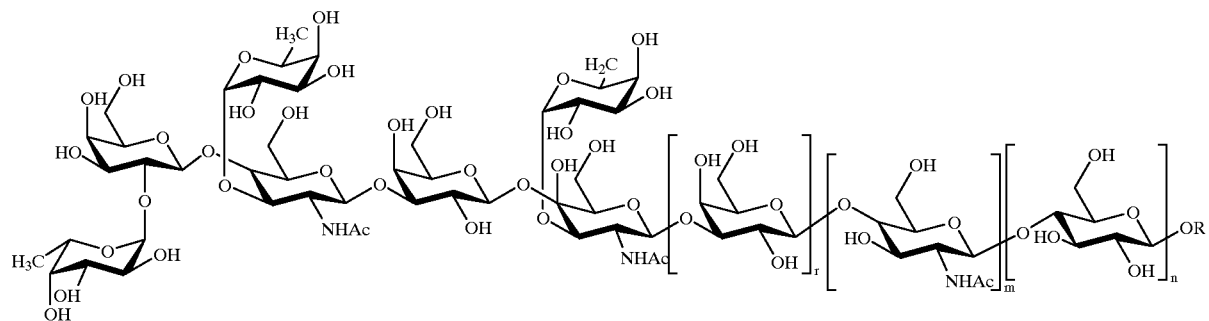

H., *Carbohydr. Res.,* 1985, 139, (105) 115; Lönn, H., *Carbohydr. Chem.,* 1987, 6, 301.

The structures of the final products 1 and 2 were fully substantiated by mass spectroscopy, self consistent nmr analysis, and in the case of 1, correspondence with the available published data. Nudelman *J. Biol. Chem.,* 1986, 261, 11247.

What is claimed is:

1. A method of inducing antibodies in a subject, wherein the antibodies arc capable of specifically binding with epithelial tumor cells, which comprises administering to the subject an amount of a compound which contains a determinant having a structure;

which amount is effective to induce antibodies, wherein the compound is bound to a suitable carrier protein, said compound being bound either directly or by a cross-linker, said method further comprising co-administering an immunological adjuvant.

2. The method of claim 1 wherein said cross-linker is selected from the group consisting of a succinimide and an $M_2$ linker.

3. The method of claim 1 wherein the compound contains a KH-1 epitope.

4. The method of claim 2 wherein the carrier protein is bovine serum albumin, polylysine or KLH.

5. The method of claim 2 wherein the compound is a KH-1 epitope.

6. The method of claim 1 wherein the adjuvant is bacteria or liposomes.

7. The method of claim 1 wherein the adjuvant is *Salmonella minnesota* cells, bacille Calmette-Guerin or QS21.

8. The method of claim 1 wherein the epithelial tumor cells are gastrointestinal tumor cells.

9. The method of claim 8 wherein the gastrointestinal tumor cells are are colon tumor cells.

10. The method of claim 1 wherein the compound has the structure wherein R is H, substituted or unsubstituted alkyl, aryl or allyl, or an amino acyl moiety, an amino acyl residue of a peptide, an amino acyl residue of a protein, which acyl amino moiety or residue bears a ω-amino group or a ω-(C=O)-group, which group is linked to O via a polymethylene chain having the structure —$(CH_2)_s$—, where s is an integer between about 1 and about 9, and wherein r, m and n are independently 0, 1, 2 or 3.

11. The method of claim 1 wherein the compound is a KH- 1 antigen.

12. The method of claim 2 wherein the compound is a KH-1 antigen.

* * * * *

UNITED STATES PATENT AND TRADEMARK OFFICE
CERTIFICATE OF CORRECTION

PATENT NO. : 6,238,668 B1
APPLICATION NO. : 09/042280
DATED : May 29, 2001
INVENTOR(S) : Samuel Danishefsky Page 1 of 1

It is certified that error appears in the above-identified patent and that said Letters Patent is hereby corrected as shown below:

In The Specification

In column 1, beginning at line 8 and ending at line 13, please delete:

"This invention was made with government support under grants CA-28824-18, GM-15240-02, GM-16291-01, HL-25848-14 and AI-16943 from the National Institutes of Health. Additionally, the present invention was supported in part by a fellowship from the United States Army to Hyun Jin Kim (DAMD 17-97-1-7119)."

and insert:

--This invention was made with government support under grant numbers: AI016943, CA028824, GM015240, GM016291, HL025848 awarded by National Institutes of Health. The government has certain rights in the invention.--

Signed and Sealed this
Twenty-ninth Day of March, 2016

Michelle K. Lee
*Director of the United States Patent and Trademark Office*